United States Patent
Aurora et al.

(10) Patent No.: US 6,638,750 B1
(45) Date of Patent: Oct. 28, 2003

(54) METHIONINE AMINOPEPTIDASE TYPE 3

(75) Inventors: Rajeev Aurora, Chesterfield, MO (US); Stanton B. Dotson, Fenton, MO (US)

(73) Assignee: Pharmacia Corporation, St. Louis, MO (US)

(*) Notice: Subject to any disclaimer, the term of this patent is extended or adjusted under 35 U.S.C. 154(b) by 0 days.

(21) Appl. No.: 09/523,263

(22) Filed: Mar. 10, 2000

Related U.S. Application Data

(60) Provisional application No. 60/125,139, filed on Mar. 11, 1999.

(51) Int. Cl.[7] ............... C12N 9/10; C12N 1/20; C12N 15/00; C07H 21/04; A61K 38/00
(52) U.S. Cl. ............... 435/212; 435/252.3; 435/320.1; 536/23.2; 536/23.6; 530/300; 530/350
(58) Field of Search ............... 435/212, 252.3, 435/320.1; 536/23.2; 530/300, 350

(56) References Cited

U.S. PATENT DOCUMENTS 6,329,188 B1   12/2001   Yan et al. ............... 435/212

OTHER PUBLICATIONS

Sequence Search alignments : Cross et al. Nat. Genet. 6 (3) : 236–244 (1994) or Kaneko et al.[DNA Res. 2 : 153–166 (1995)].*

Sequence Search Alignments [EST] —AI333643 [Feb. 13, 1999] or AI129521 [Oct. 27, 1998].*

* cited by examiner

*Primary Examiner*—Tekchand Saidha
(74) *Attorney, Agent, or Firm*—Verne A. Luckow

(57) ABSTRACT

The present invention relates to a human cDNA encoding a methionine aminopeptidase type-3 (MetAP-3) protein. The invention also relates to nucleic acid molecules associated with or derived from this cDNA including complements, homologues and fragments thereof, and methods of using these nucleic acid molecules, to generate, for example, polypeptides and fragments thereof. The invention also provides methods of using the nucleic acids, for example, to produce a protein and fragments thereof and to screen for compounds or compositions that preferentially or specifically effect the activity of a MetAP-3 protein.

7 Claims, 26 Drawing Sheets

```
map3gt  ------------------------------------------------------GCG
                                                              :::
GT      CGCCTGCAGGTACCGGTCCGGAATTCCCGGGTCGACCCACGCGTCCGCGCCAACATGGCG
                 10        20        30        40        50        60

10        20        30
map3gt  GCGCC-AGTGGCGTCCACCTGCTCGTCCGCAGAGGT------------------------
        ::::: :::::::::::::::::::::::::::::
GT      GCGCCCAGTGGCGTCCACCTGCTCGTCCGCAGAGGTAAGCGCGTGGAGGAGAGCCCCGTG
                 70        80        90       100       110       120

40        50        60        70
map3gt  ---------------------------TCTCATAGAATTTTCTCTTCACCACTCAATCATA
                                   ::::::::::::::::::::::::::::::::::
GT      AGGGTTCGCACGGTTGCTCACTAGGTTCTCATAGAATTTTCTCTTCACCACTCAATCATA
                130       140       150       160       170       180
                80        90       100       110       120       130
map3gt  TCTACTTACACAAGCAGTCAAGCAGTCAACAAAGAAGAAATTTCTTTTTTCGGAGACAAA
        ::::::::::::::::::::::::::::::::::::::::::::::::::::::::::::
GT      TCTACTTACACAAGCAGTCAAGCAGTCAACAAAGAAGAAATTTCTTTTTTCGGAGACAAA
                190       200       210       220       230       240
                140       150       160       170       180       190
map3gt  GAGATATTTCACACAGTATAGTTTTGCCGGCTGCAGTTTCTTCAGCTCATCCGGTTCCTA
        ::::::::::::::::::::::::::::::::::::::::::::::::::::::::::::
GT      GAGATATTTCACACAGTATAGTTTTGCCGGCTGCAGTTTCTTCAGCTCATCCGGTTCCTA
                250       260       270       280       290       300
                200       210       220       230       240       250
map3gt  AGCACATAAAGAAGCCAGACTATGTGACGACAGGCATTGTACCAGACTGGGGAGACAGCA
        ::::::::::::::::::::::::::::::::::::::::::::::::::::::::::::
GT      AGCACATAAAGAAGCCAGACTATGTGACGACAGGCATTGTACCAGACTGGGGAGACAGCA
                310       320       330       340       350       360
                260       270       280       290       300       310
map3gt  TAGAAGTTAAGAATGAAGATCAGATTCAAGGGCTTCATCAGGCTTGTCAGCTGGCCCGCC
        :::::::::::::::::::::::::::::::::::::::::::::::::::::::: :::
GT      TAGAAGTTAAGAATGAAGATCAGATTCAAGGGCTTCATCAGGCTTGTCAGCTGGCC-GCC
                370       380       390       400       410
                320       330       340       350       360       370
map3gt  ACGTCCTCCTCTTGGCTGGGAAGAGTTTAAAGGTTGACATGACAACTGAAGAGATAGATG
        ::::::::::::::::::::::::::::::::::::::::::::::::::::::::::::
GT      ACGTCCTCCTCTTGGCTGGGAAGAGTTTAAAGGTTGACATGACAACTGAAGAGATAGATG
           420       430       440       450       460       470
             380       390       400       410       420       430
```

*FIG. 2A*

```
map3gt  CTCTTGTTCATCGGGAAATCATCAGTCATAATGCCTATCCCTCACCTCTAGGCTATGGAG
        ::::::::::::::::::::::::::::::::::::::::::::::::::::::::::::
GT      CTCTTGTTCATCGGGAAATCATCAGTCATAATGCCTATCCCTCACCTCTAGGCTATGGAG
        480       490       500       510       520       530
            440       450       460       470       480       490
map3gt  GTTTTCCAAAATCTGTTTGTACCTCTGTAAACAACGTGCTCTGTCATGGTATTCCTGACA
        ::::::::::::::::::::::::::::::::::::::::::::::::::::::::::::
GT      GTTTTCCAAAATCTGTTTGTACCTCTGTAAACAACGTGCTCTGTCATGGTATTCCTGACA
        540       550       560       570       580       590
            500       510       520       530       540       550
map3gt  GTCGACCTCTTCAGGATGGAGATATTATCAACATTGATGTCACAGTCTATTACAATGGCT
        ::::::::::::::::::::::::::::::::::::::::::::::::::::::::::::
GT      GTCGACCTCTTCAGGATGGAGATATTATCAACATTGATGTCACAGTCTATTACAATGGCT
        600       610       620       630       640       650
            560       570       580       590       600       610
map3gt  ACCATGGAGACACCTCTGAAACATTTTGGTGGGCAATGTGGACGAATGTGGTAAAAAGT
        ::::::::::::::::::::::::::::::::::::::::: ::::::::::::::::::
GT      ACCATGGAGACACCTCTGAAACATTTTGGTGGGCAATGAGGACGAATGTGGTAAAAAGT
        660       670       680       690       700       710
            620       630       640       650       660       670
map3gt  TAGTGGAGGTTGCCAGGAGGTGTAGAGATGAAGCAATTGCAGCTTGCAGAGCAGGGGCTC
        ::::::::::::::::::::::::::::::::::::::::::::::::::::::::::::
GT      TAGTGGAGGTTGCCAGGAGGTGTAGAGATGAAGCAATTGCAGCTTGCAGAGCAGGGGCTC
        720       730       740       750       760       770
            680       690       700       710       720       730
map3gt  CCTTCTCTGTAATTGGAAACACAATCAGCCACATAACTCATCAGAATGGTTTTCAAGTCT
        ::::::::::::::::::::::::::::::::::::::::::::::::::::::::::::
GT      CCTTCTCTGTAATTGGAAACACAATCAGCCACATAACTCATCAGAATGGTTTTCAAGTCT
        780       790       800       810       820       830
            740       750       760       770       780       790
map3gt  GTCCACATTTTGTGGGACATGGAATAGGATCTTACTTTCATGGACATCCAGAAATTTGGC
        ::::::::::::::::::::::::::::::::::::::::::::::::::::::::::::
GT      GTCCACATTTTGTGGGACATGGAATAGGATCTTACTTTCATGGACATCCAGAAATTTGGC
        840       850       860       870       880       890
            800       810       820       830       840       850
map3gt  ATCATGCAAACGACAGTGATCTACCCATGGAGGAGGGCATGGCATTCACTATAGAGCCAA
        ::::::::::::::::::::::::::::::::::::::::::::::::::::::::::::
GT      ATCATGCAAACGACAGTGATCTACCCATGGAGGAGGGCATGGCATTCACTATAGAGCCAA
        900       910       920       930       940       950
            860       870       880       890       900       910
map3gt  TCATCACGGAGGGATCCCCTGAATTTAAAGTCCTGGAGGATGCATGGACTGTGGTCTCCC
        ::::::::::::::::::::::::::::::::::::::::::::::::::::::::::::
GT      TCATCACGGAGGGATCCCCTGAATTTAAAGTCCTGGAGGATGCATGGACTGTGGTCTCCC
```

FIG. 2B

```
         960       970       980       990       1000      1010
            920       930       940       950       960       970
map3gt TAGACAATCAAAGGTCGGCGCAGTTCGAGCACACGGTTCTGATCACGTCGAGGGGCGCGC
       ::::::::::::::::::::::::::::::::::::::::::::::::::::::::::::
GT     TAGACAATCAAAGGTCGGCGCAGTTCGAGCACACGGTTCTGATCACGTCGAGGGGCGCGC
         1020      1030      1040      1050      1060      1070
            980       990      1000      1010      1020      1030
map3gt AGATCCTGACCAAACTACCCCATGAGGCCTGAGGAGCCGCCCGAAGGTCGCGGTGACCTG
       ::::::::::::::::::::::::::::::::::::::::::::::::::::::::::::
GT     AGATCCTGACCAAACTACCCCATGAGGCCTGAGGAGCCGCCCGAAGGTCGCGGTGACCTG
         1080      1090      1100      1110      1120      1130
           1040      1050      1060      1070      1080      1090
map3gt GTGCCTTTTTAAATAAATTGCTGAAATTTGGCTGGAGAACTTTTAGAAGAAACAGGGAAA
       ::::::::::::::::::::::::::::::::::::::::::::::::::::::::::::
GT     GTGCCTTTTTAAATAAATTGCTGAAATTTGGCTGGAGAACTTTTAGAAGAAACAGGGAAA
         1140      1150      1160      1170      1180      1190
           1100      1110      1120      1130      1140      1150
map3gt TGACCGGTGGTGCGGTAACCTGCGTGGCTCCTGATAGCGTTTGGAAGAACGCGGGGGAGA
       ::::::::::::::::::::::::::::::::::::::::::::::::::::::::::::
GT     TGACCGGTGGTGCGGTAACCTGCGTGGCTCCTGATAGCGTTTGGAAGAACGCGGGGGAGA
         1200      1210      1220      1230      1240      1250
           1160      1170      1180      1190      1200      1210
map3gt CTGAAGAGCAACTGGGAACTCGGATCTGAAGCCCTGCTGGGGTCGCGCGGCTTTGGAAAA
       ::::::::::::::::::::::::::::::::::::::::::::::::::::::::::::
GT     CTGAAGAGCAACTGGGAACTCGGATCTGAAGCCCTGCTGGGGTCGCGCGGCTTTGGAAAA
         1260      1270      1280      1290      1300      1310
           1220      1230      1240      1250      1260      1270
map3gt ACAAATCCTGGCCCTGGACTCGGTTTCCCAGCGCGGTCAACGCATGTGGAGGGGACTGGA
       ::::::::::::::::::::::::::::::::::::::::::  ::::::::::::::::
GT     ACAAATCCTGGCCCTGGACTCGGTTTCCCAGCGCGGTCAACGCATCTGGAGGGGACTGGA
         1320      1330      1340      1350      1360      1370
           1280      1290      1300      1310      1320      1330
map3gt GGAAACCCCCTTGTTGGAAGAGATTCCAAGAGAAGCACGGKTTTCTCTTTCCCNTGCCCT
       ::::::::::::::::::::::::::::::::::::::::.:::::::::::: ::::::
GT     GGAAACCCCCTTGTTGGAAGAGATTCCAAGAGAAGCACGGTTTTCTCTTTCCCCTTGCCCT
         1380      1390      1400      1410      1420      1430
           1340      1350      1360
map3gt GACTGTTGGAGTAAAAAACCTCTTAAATCCA-----------------------------
       :::::::::::::::::::::::::::::::
GT     GACTGTTGGAGTAAAAAACCTCTTAAATCCAAAAAAAAAAAAAAAAAAAAAAAAAAGGGC
         1440      1450      1460      1470      1480      1490
map3gt ------
GT     GGCCGC
         1500
```

*FIG. 2C*

| WELL | SAMPLE NAME | CT | AVG CT | WELL | SAMPLE NAME | CT | AVGCT | DCT | DDCT | X EXPRESSION |
|---|---|---|---|---|---|---|---|---|---|---|
| 2-9-00#1 | | | | 2-9-00#1 | | | | | | |
| A1 | CYCLOPHILIN KIDNEY | 16.83 | 16.83 | C1 | MetAP1 KIDNEY | 24.84 | 24.88 | 8.045 | -1.4 | 2.639015822 |
| B1 | CYCLOPHILIN KIDNEY | 16.83 | | D1 | MetAP1 KIDNEY | 24.91 | | | | |
| A2 | CYCLOPHILIN ADRENAL | 17.18 | 17.175 | C2 | MetAP1 ADRENAL | 26.83 | 26.62 | 9.445 | 0 | 1 |
| B2 | CYCLOPHILIN ADRENAL | 17.17 | | D2 | MetAP1 ADRENAL | 26.41 | | | | |
| A3 | CYCLOPHILIN UTERUS | 17.96 | 17.83 | C3 | MetAP1 UTERUS | 24.91 | 25.05 | 7.215 | -2.23 | 4.691339797 |
| B3 | CYCLOPHILIN UTERUS | 17.7 | | D3 | MetAP1 UTERUS | 25.18 | | | | |
| A4 | CYCLOPHILIN HEART | 25.12 | 25.425 | C4 | MetAP1 HEART | 33.33 | 33.2 | 7.77 | -1.675 | 3.193193545 |
| B4 | CYCLOPHILIN HEART | 25.73 | | D4 | MetAP1 HEART | 33.06 | | | | |
| A5 | CYCLOPHILIN PROSTATE | 17.21 | 17.28 | C5 | MetAP1 PROSTATE | 24.27 | 24.24 | 6.955 | -2.49 | 5.617779503 |
| B5 | CYCLOPHILIN PROSTATE | 17.35 | | D5 | MetAP1 PROSTATE | 24.2 | | | | |
| A6 | CYCLOPHILIN SMALL INTESTIN | 18.07 | 18.085 | C6 | MetAP1 SMALL INTESTINE | 25.19 | 25.17 | 7.085 | -2.36 | 5.13370359 |
| B6 | CYCLOPHILIN SMALL INTESTIN | 18.1 | | D6 | MetAP1 SMALL INTESTINE | 25.15 | | | | |
| A7 | CYCLOPHILIN CEREBELLUM | 17.57 | 17.65 | C7 | MetAP1 CEREBELLUM | 25.62 | 25.48 | 7.83 | -1.615 | 3.063115994 |
| B7 | CYCLOPHILIN CEREBELLUM | 17.73 | | D7 | MetAP1 CEREBELLUM | 25.34 | | | | |
| A8 | CYCLOPHILIN LUNG | 22.13 | 22.17 | C8 | MetAP1 LUNG | 32.13 | 32.18 | 10.005 | 0.56 | 0.678302164 |
| B8 | CYCLOPHILIN LUNG | 22.21 | | D8 | MetAP1 LUNG | 32.22 | | | | |
| A9 | CYCLOPHILIN BONE MARROW | 17.53 | 17.57 | C9 | MetAP1 BONE MARROW | 25.47 | 25.42 | 7.845 | -1.6 | 3.031433133 |
| B9 | CYCLOPHILIN BONE MARROW | 17.61 | | D9 | MetAP1 BONE MARROW | 25.36 | | | | |
| A10 | CYCLOPHILIN COLON | 17.21 | 17.3 | C10 | MetAP1 COLON | 25.01 | 25.05 | 7.75 | -1.695 | 3.237768866 |
| B10 | CYCLOPHILIN COLON | 17.39 | | D10 | MetAP1 COLON | 25.09 | | | | |
| A11 | CYCLOPHILIN SPINAL CHORD | 17.06 | 17.02 | C11 | MetAP1 SPINAL CHORD | 25.41 | 25.5 | 8.475 | -0.97 | 1.958840595 |
| B11 | CYCLOPHILIN SPINAL CHORD | 16.98 | | D11 | MetAP1 SPINAL CHORD | 25.58 | | | | |
| 2-10-00#1 | | | | 2-10-00#1 | | | | | | |
| A1 | CYCLOPHILIN SMALL INTESTIN | 18.11 | 18.175 | C1 | MetAP1 SMALL INTESTINE | 25.14 | 25.19 | 7.01 | -2.435 | 5.407643332 |
| B1 | CYCLOPHILIN SMALL INTESTIN | 18.24 | | D1 | MetAP1 SMALL INTESTINE | 25.23 | | | | |
| A2 | CYCLOPHILIN TESTIS | 17.5 | 17.465 | C2 | MetAP1 TESTIS | 22.5 | 22.47 | 5.005 | -4.44 | 21.70566924 |
| B2 | CYCLOPHILIN TESTIS | 17.43 | | D2 | MetAP1 TESTIS | 22.44 | | | | |
| A3 | CYCLOPHILIN HEART | 17.87 | 17.83 | C3 | MetAP1 HEART | 24.12 | 23.99 | 6.16 | -3.285 | 9.747282109 |
| B3 | CYCLOPHILIN HEART | 17.79 | | D3 | MetAP1 HEART | 23.86 | | | | |
| A4 | CYCLOPHILIN LIVER | 17.83 | 17.805 | C4 | MetAP1 LIVER | 25.13 | 25.17 | 7.36 | -2.085 | 4.242750965 |
| B4 | CYCLOPHILIN LIVER | 17.78 | | D4 | MetAP1 LIVER | 25.2 | | | | |
| A5 | CYCLOPHILIN THYMUS | 17.2 | 17.21 | C5 | MetAP1 THYMUS | 23.91 | 24.03 | 6.815 | -2.63 | 6.190259974 |
| B5 | CYCLOPHILIN THYMUS | 17.22 | | D5 | MetAP1 THYMUS | 24.14 | | | | |
| A6 | CYCLOPHILIN BRAIN | 16.15 | 16.125 | C6 | MetAP1 BRAIN | 23.74 | 23.84 | 7.71 | -1.735 | 3.328794939 |
| B6 | CYCLOPHILIN BRAIN | 16.1 | | D6 | MetAP1 BRAIN | 23.93 | | | | |

| WELL | SAMPLE NAME | CT | AVGCTDCT | DDCT | X EXPRESSION | WELL | SAMPLE NAME | CT | AVGCT | DCT | DDCT | X EXPRESSION |
|---|---|---|---|---|---|---|---|---|---|---|---|---|
| 2-9-00#1 | | | | | | 2-9-00#1 | | | | | | |
| E1 | MetAP2 KIDNEY | 22.3 | 22.31 5.48 | -0.6 | 1.515716567 | G1 | MetAP3 KIDNEY | 25.5 / 25.54 | 25.52 | 8.69 | -1.485 | 2.799171731 |
| F1 | MetAP2 KIDNEY | 22.32 | | | | H1 | MetAP3 KIDNEY | 24.83 / 24.9 | 24.87 | 7.69 | -2.485 | 5.598343462 |
| E2 | MetAP2 ADRENAL | 21.97 / 21.39 | 21.68 4.505 | -1.575 | 2.979354926 | G2 | MetAP3 ADRENAL | 25.56 / 25.36 | 25.46 | 7.63 | -2.545 | 5.836081377 |
| F2 | MetAP2 ADRENAL | | | | | H2 | MetAP3 ADRENAL | | | | | |
| E3 | MetAP2 UTERUS | 22.24 / 22.19 | 22.22 4.385 | -1.695 | 3.237768866 | G3 | MetAP3 UTERUS | 36.02 / 34.76 | 35.39 | 9.965 | -0.21 | 1.156688184 |
| F3 | MetAP2 UTERUS | | | | | H3 | MetAP3 UTERUS | | | | | |
| E4 | MetAP2 HEART | 31.48 / 31.53 | 31.51 6.08 | 0 | | G4 | MetAP3 HEART | 25.61 / 25.46 | 25.54 | 8.255 | -1.92 | 3.784230587 |
| F4 | MetAP2 HEART | | | | | H4 | MetAP3 HEART | | | | | |
| E5 | MetAP2 PROSTATE | 22.48 / 22.14 | 22.31 5.03 | -1.05 | 2.070529848 | G5 | MetAP3 PROSTATE | 25.72 / 25.42 | 25.57 | 7.485 | -2.69 | 6.453134074 |
| F5 | MetAP2 PROSTATE | | | | | H5 | MetAP3 PROSTATE | | | | | |
| E6 | MetAP2 SMALL INTESTINE | 22.47 / 22.82 | 22.65 4.56 | -1.52 | 2.867910496 | G6 | MetAP3 SMALL INTESTINE | 25.98 / 25.81 | 25.9 | 8.245 | -1.93 | 3.810551992 |
| F6 | MetAP2 SMALL INTESTINE | | | | | H6 | MetAP3 SMALL INTESTINE | | | | | |
| E7 | MetAP2 CEREBELLUM | 22.27 / 22.37 | 22.32 4.67 | -1.41 | 2.657371628 | G7 | MetAP3 CEREBELLUM | 32.76 / 32.43 | 32.6 | 10.425 | 0.25 | 0.840896415 |
| F7 | MetAP2 CEREBELLUM | | | | | H7 | MetAP3 CEREBELLUM | | | | | |
| E8 | MetAP2 LUNG | 29.48 / 29.16 | 29.32 7.15 | 1.07 | 0.476318999 | G8 | MetAP3 LUNG | 26.02 / 25.63 | 25.83 | 8.255 | -1.92 | 3.784230587 |
| F8 | MetAP2 LUNG | | | | | H8 | MetAP3 LUNG | | | | | |
| E9 | MetAP2 BONE MARROW | 21.94 / 21.61 | 21.78 4.205 | -1.875 | 3.668016173 | G9 | MetAP3 BONE MARROW | 27.06 / 26.46 | 26.76 | 9.46 | -0.715 | 1.641483218 |
| F9 | MetAP2 BONE MARROW | | | | | H9 | MetAP3 BONE MARROW | | | | | |
| E10 | MetAP2 COLON | 22.68 / 22.51 | 22.6 5.295 | -0.785 | 1.723092319 | G10 | MetAP3 COLON | 25.22 / 24.99 | 25.11 | 8.085 | -2.09 | 4.25748073 |
| F10 | MetAP2 COLON | | | | | H10 | MetAP3 COLON | | | | | |
| E11 | MetAP2 SPINAL CHORD | 21.29 / 21.23 | 21.26 4.24 | -1.84 | 3.580100284 | G11 | MetAP3 SPINAL CHORD | | | | | |
| F11 | MetAP2 SPINAL CHORD | | | | | H11 | MetAP3 SPINAL CHORD | | | | | |
| 2-10-00#1 | | | | | | 2-10-00#1 | | | | | | |
| E1 | MetAP2 SMALL INTESTINE | 22.42 / 22.58 | 22.5 4.325 | -1.755 | 3.375263185 | G1 | MetAP3 SMALL INTESTINE | 26.01 / 25.81 | 25.91 | 7.735 | -2.44 | 5.42641731 |
| F1 | MetAP2 SMALL INTESTINE | | | | | H1 | MetAP3 SMALL INTESTINE | | | | | |
| E2 | MetAP2 TESTIS | 19.81 / 19.87 | 19.84 2.375 | -3.705 | 13.04115732 | G2 | MetAP3 TESTIS | 24.99 / 24.81 | 24.9 | 7.435 | -2.74 | 6.680703355 |
| F2 | MetAP2 TESTIS | | | | | H2 | MetAP3 TESTIS | | | | | |
| E3 | MetAP2 HEART | 21.05 / 21.14 | 21.1 3.265 | -2.815 | 7.037192607 | G3 | MetAP3 HEART | 25.25 / 25.11 | 25.18 | 7.35 | -2.825 | 7.086140153 |
| F3 | MetAP2 HEART | | | | | H3 | MetAP3 HEART | | | | | |
| E4 | MetAP2 LIVER | 21.57 / 21.75 | 21.66 3.855 | -2.255 | 13.04115732 | G4 | MetAP3 LIVER | 25.34 / 25.46 | 25.4 | 7.595 | -2.58 | 5.979396995 |
| F4 | MetAP2 LIVER | | | | | H4 | MetAP3 LIVER | | | | | |
| E5 | MetAP2 THYMUS | 21.75 / 22.07 | 21.91 4.7 | -1.38 | 2.602683711 | G5 | MetAP3 THYMUS | 27.51 / 27.26 | 27.39 | 10.175 | 0 | 1 |
| F5 | MetAP2 THYMUS | | | | | H5 | MetAP3 THYMUS | | | | | |
| E6 | MetAP2 BRAIN | 20.38 / 20.46 | 20.42 4.295 | -1.785 | 3.446184639 | G6 | MetAP3 BRAIN | 24.01 / 24.01 | 24.01 | 7.885 | -2.29 | 4.890561111 |
| F6 | MetAP2 BRAIN | | | | | H6 | MetAP3 BRAIN | | | | | |

FIG. 8C

| WELL | SAMPLE NAME | | CT | AVG CT | WELL | SAMPLE NAME | | CT | AVGCT | DCT | DDCT | X EXPRESSION |
|---|---|---|---|---|---|---|---|---|---|---|---|---|
| 2-10-00#1 | | | | | 2-10-00#1 | | | | | | | |
| A7 | 18 | CYCLOPHILIN FETAL BRAIN | 17.09 | 17.205 | C7 | MetAP1 | FETAL BRAIN | 24.11 | 23.79 | 6.585 | -2.86 | 7.260153243 |
| B7 | | CYCLOPHILIN FETAL BRAIN | 17.32 | | C7 | MetAP1 | FETAL BRAIN | 23.47 | | | | |
| A8 | 19 | CYCLOPHILIN SALIVARY | 18.29 | 18.31 | C8 | MetAP1 | SALIVARY | 25.35 | 25.47 | 7.16 | -2.285 | 4.873641055 |
| B8 | | CYCLOPHILIN SALIVARY | 18.33 | | D8 | MetAP1 | SALIVARY | 25.59 | | | | |
| A9 | 21 | CYCLOPHILIN MUSCLE | 19.8 | 19.85 | C9 | MetAP1 | MUSCLE | 25.11 | 25.1 | 5.245 | -4.2 | 18.37917368 |
| B9 | | CYCLOPHILIN MUSCLE | 19.9 | | D9 | MetAP1 | MUSCLE | 25.08 | | | | |
| A10 | 22 | CYCLOPHILIN SPLEEN | 17.33 | 17.365 | C10 | MetAP1 | SPLEEN | 24.95 | 25.01 | 7.645 | -1.8 | 3.482202253 |
| B10 | | CYCLOPHILIN SPLEEN | 17.4 | | D10 | MetAP1 | SPLEEN | 25.07 | | | | |
| A11 | 23 | CYCLOPHILIN BRAIN | 16.46 | 16.445 | C11 | MetAP1 | BRAIN | 24.22 | 24.27 | 7.825 | -1.62 | 3.073750363 |
| B11 | | CYCLOPHILIN BRAIN | 16.43 | | D11 | MetAP1 | BRAIN | 24.32 | | | | |
| 2-10-00#2 | | | | | 2-10-00#2 | | | | | | | |
| A1 | 6 | CYCLOPHILIN SMALL INTESTIN | 18.07 | 18.12 | C1 | MetAP1 | SMALL INTESTINE | 25.39 | 25.36 | 7.235 | -2.21 | 4.626752736 |
| B1 | | CYCLOPHILIN SMALL INTESTIN | 18.17 | | D1 | MetAP1 | SMALL INTESTINE | 25.32 | | | | |
| A2 | 24 | CYCLOPHILIN THYROID | 17.84 | 17.82 | C2 | MetAP1 | THYROID | 25.9 | 25.94 | 8.12 | -1.325 | 2.505328877 |
| B2 | | CYCLOPHILIN THYROID | 17.8 | | D2 | MetAP1 | THYROID | 25.98 | | | | |
| A3 | 25 | CYCLOPHILIN MAMMARY | 18.31 | 18.025 | C3 | MetAP1 | MAMMARY | 25.36 | 25.3 | 7.275 | -2.17 | 4.500233939 |
| B3 | | CYCLOPHILIN MAMMARY | 17.74 | | D3 | MetAP1 | MAMMARY | 25.24 | | | | |
| A4 | 26 | CYCLOPHILIN PLACENTA | 18.67 | 18.55 | C4 | MetAP1 | PLACENTA | 26.72 | 26.54 | 7.985 | -1.46 | 2.751083636 |
| B4 | | CYCLOPHILIN PLACENTA | 18.43 | | D4 | MetAP1 | PLACENTA | 26.35 | | | | |
| A5 | 27 | CYCLOPHILIN FETAL LIVER | 17.68 | 17.835 | C5 | MetAP1 | FETAL LIVER | 25.5 | 25.64 | 7.8 | -1.645 | 3.127478573 |
| B5 | | CYCLOPHILIN FETAL LIVER | 17.99 | | D5 | MetAP1 | FETAL LIVER | 25.77 | | | | |
| A6 | 28 | CYCLOPHILIN TRACHEA | 18.79 | 18.84 | C6 | MetAP1 | TRACHEA | 26.12 | 25.9 | 7.055 | -2.39 | 5.241573615 |
| B6 | | CYCLOPHILIN TRACHEA | 18.89 | | D6 | MetAP1 | TRACHEA | 25.67 | | | | |
| A7 | 29 | CYCLOPHILIN PANCREAS | 20.25 | 20.22 | C7 | MetAP1 | PANCREAS | 28.05 | 27.98 | 7.76 | -1.685 | 3.215403963 |
| B7 | | CYCLOPHILIN PANCREAS | 20.19 | | D7 | MetAP1 | PANCREAS | 27.91 | | | | |
| A8 | 30 | CYCLOPHILIN STOMACH | 19.86 | 19.965 | C8 | MetAP1 | STOMACH | 27.48 | 27.23 | 7.26 | -2.185 | 4.547267893 |
| B8 | | CYCLOPHILIN STOMACH | 20.07 | | D8 | MetAP1 | STOMACH | 26.97 | | | | |
| 2-9-00#1 | | | | | | | | | | | | |
| A6 | 6 | CYCLOPHILIN SMALL INTESTIN | 18.07 | 18.085 | C6 | MetAP1 | SMALL INTESTINE | 25.19 | 25.17 | 7.085 | -2.36 | 5.13370359 |
| B6 | | CYCLOPHILIN SMALL INTESTIN | 18.1 | | D6 | MetAP1 | SMALL INTESTINE | 25.15 | | | | |
| 2-10-00#1 | | | | | | | | | | | | |
| A1 | 6 | CYCLOPHILIN SMALL INTESTIN | 18.11 | 18.175 | C1 | MetAP1 | SMALL INTESTINE | 25.14 | 25.19 | 7.01 | -2.435 | 5.407643332 |
| B1 | | CYCLOPHILIN SMALL INTESTIN | 18.24 | | D1 | MetAP1 | SMALL INTESTINE | 25.23 | | | | |
| 2-10-00#2 | | | | | | | | | | | | |
| A1 | 6 | CYCLOPHILIN SMALL INTESTIN | 18.07 | 18.12 | C1 | MetAP1 | SMALL INTESTINE | 25.39 | 25.36 | 7.235 | -2.21 | 4.626752736 |
| B1 | | CYCLOPHILIN SMALL INTESTIN | 18.17 | | D1 | MetAP1 | SMALL INTESTINE | 25.32 | | | | |

FIG. 8D

| WELL | SAMPLE NAME | CT | AVGCTDCT | DDCT | X EXPRESSION | WELL | SAMPLE NAME | CT | AVGCT | DCT | DDCT | X EXPRESSION |
|---|---|---|---|---|---|---|---|---|---|---|---|---|
| 2-9-00#1 | | | | | | 2-9-00#1 | | | | | | |
| E7 | MetAP2 FETAL BRAIN | 21.38 | 21.36 4.155 | -1.925 | 3.797368484 | G7 | MetAP3 FETAL BRAIN | 23.04 | 22.91 | 5.705 | -4.47 | 22.16175149 |
| F7 | MetAP2 FETAL BRAIN | 21.34 | | | | H7 | MetAP3 FETAL BRAIN | 22.78 | | | | |
| E8 | MetAP2 SALIVARY | 22.43 | 22.42 4.105 | -1.975 | 3.931282394 | G8 | MetAP3 SALIVARY | 25.72 | 25.74 | 7.43 | -2.745 | 6.703897077 |
| F8 | MetAP2 SALIVARY | 22.43 | | | | H8 | MetAP3 SALIVARY | 25.72 | | | | |
| E9 | MetAP2 MUSCLE | 21.43 | 21.48 1.63 | -4.45 | 21.85664411 | G9 | MetAP3 MUSCLE | 25 | 25 | 5.15 | -5.025 | 32.55935015 |
| F9 | MetAP2 MUSCLE | 21.53 | | | | H9 | MetAP3 MUSCLE | 25 | | | | |
| E10 | MetAP2 SPLEEN | 22.01 | 22 4.635 | -1.445 | 2.722628233 | G10 | MetAP3 SPLEEN | 25.29 | 25.15 | 7.78 | -2.395 | 5.259771041 |
| F10 | MetAP2 SPLEEN | 21.99 | | | | H10 | MetAP3 SPLEEN | 25 | | | | |
| E11 | MetAP2 BRAIN | 21.13 | 21.15 4.705 | -1.375 | 2.593679109 | G11 | MetAP3 BRAIN | 24.37 | 24.34 | 7.895 | -2.28 | 4.856779538 |
| F11 | MetAP2 BRAIN | 21.17 | | | | H11 | MetAP3 BRAIN | 24.31 | | | | |
| 2-10-00#2 | | | | | | 2-10-00#2 | | | | | | |
| E1 | MetAP2 SMALL INTESTINE | 23.12 | 23.12 5 | -1.08 | 2.114036081 | G1 | MetAP3 SMALL INTESTINE | 25.98 | 25.74 | 7.62 | -2.555 | 5.876674533 |
| F1 | MetAP2 SMALL INTESTINE | 23.12 | | | | H1 | MetAP3 SMALL INTESTINE | 25.5 | | | | |
| E2 | MetAP2 THYROID | 23.07 | 22.94 5.12 | -0.96 | 1.945509895 | G2 | MetAP3 THYROID | 26.24 | 26.24 | 8.415 | -1.76 | 3.386981249 |
| F2 | MetAP2 THYROID | 22.81 | | | | H2 | MetAP3 THYROID | 26.23 | | | | |
| E3 | MetAP2 MAMMARY | 22.3 | 22.29 4.26 | -1.82 | 3.530811985 | G3 | MetAP3 MAMMARY | 24.76 | 24.82 | 6.795 | -3.38 | 10.41073484 |
| F3 | MetAP2 MAMMARY | 22.27 | | | | H3 | MetAP3 MAMMARY | 24.88 | | | | |
| E4 | MetAP2 PLACENTA | 22.93 | 22.77 4.22 | -1.86 | 3.630076621 | G4 | MetAP3 PLACENTA | 26.66 | 26.72 | 8.165 | -2.01 | 4.0278222 |
| F4 | MetAP2 PLACENTA | 22.61 | | | | H4 | MetAP3 PLACENTA | 26.77 | | | | |
| E5 | MetAP2 FETAL LIVER | 21.96 | 21.81 3.97 | -2.11 | 4.316912946 | G5 | MetAP3 FETAL LIVER | 25.59 | 25.5 | 7.66 | -2.515 | 5.715976559 |
| F5 | MetAP2 FETAL LIVER | 21.65 | | | | H5 | MetAP3 FETAL LIVER | 25.4 | | | | |
| E6 | MetAP2 TRACHEA | 24.31 | 24.2 5.36 | -0.72 | 1.647182035 | G6 | MetAP3 TRACHEA | 26.26 | 26.39 | 7.545 | -2.63 | 6.190259974 |
| F6 | MetAP2 TRACHEA | 24.09 | | | | H6 | MetAP3 TRACHEA | 26.51 | | | | |
| E7 | MetAP2 PANCREAS | 25.12 | 25.04 4.815 | -1.265 | 2.403272099 | G7 | MetAP3 PANCREAS | 27.24 | 27.13 | 6.905 | 3.27 | 9.646462622 |
| F7 | MetAP2 PANCREAS | 24.95 | | | | H7 | MetAP3 PANCREAS | 27.01 | | | | |
| E8 | MetAP2 STOMACH | 24.61 | 24.48 4.51 | -1.57 | 2.969047141 | G8 | MetAP3 STOMACH | 27.37 | 27.23 | 7.265 | -2.91 | 7.516181994 |
| F8 | MetAP2 STOMACH | 24.34 | | | | H8 | MetAP3 STOMACH | 27.09 | | | | |
| 2-10-00#2 | | | | | | 2-10-00#2 | | | | | | |
| E6 | MetAP2 SMALL INTESTINE | 22.47 | 22.65 4.56 | -1.52 | 2.867910496 | G6 | MetAP3 SMALL INTESTINE | 25.72 | 25.57 | 7.485 | -2.69 | 6.453134074 |
| F6 | MetAP2 SMALL INTESTINE | 22.82 | | | | H6 | MetAP3 SMALL INTESTINE | 25.42 | | | | |
| E1 | MetAP2 SMALL INTESTINE | 22.42 | 22.5 4.325 | -1.755 | 3.375263185 | G1 | MetAP3 SMALL INTESTINE | 26.01 | 25.91 | 7.735 | -2.44 | 5.42641731 |
| F1 | MetAP2 SMALL INTESTINE | 22.58 | | | | H1 | MetAP3 SMALL INTESTINE | 25.81 | | | | |
| E1 | MetAP2 SMALL INTESTINE | 23.12 | 23.12 5 | -1.08 | 2.114036081 | G1 | MetAP3 SMALL INTESTINE | 25.98 | 25.74 | 7.62 | -2.555 | 5.876674533 |
| F1 | MetAP2 SMALL INTESTINE | 23.12 | | | | H1 | MetAP3 SMALL INTESTINE | 25.5 | | | | |

| WELL | SAMPLE NAME | CT | AVGCT | DCT | DDCT | FOLD EXPRESSION |
|---|---|---|---|---|---|---|
| 2-9-00#1 | | | | | | |
| A1 | CYCLOPHILIN KIDNEY | 16.83 | 16.83 | 0 | | |
| B1 | CYCLOPHILIN KIDNEY | 16.83 | | | | |
| C1 | MetAP1 KIDNEY | 24.84 | 24.875 | 8.045 | -0.65 | 1.563739286 |
| D1 | MetAP1 KIDNEY | 24.91 | | | | |
| E1 | MetAP2 KIDNEY | 22.3 | 22.31 | 5.48 | -3.21 | 9.253505471 |
| F1 | MetAP2 KIDNEY | 22.32 | | | | |
| G1 | MetAP3 KIDNEY | 25.5 | 25.52 | 8.69 | 0 | 1 |
| H1 | MetAP3 KIDNEY | 25.54 | | | | |
| A2 | CYCLOPHILIN ADRENAL | 17.18 | 17.175 | 0 | | |
| B2 | CYCLOPHILIN ADRENAL | 17.17 | | | | |
| C2 | MetAP1 ADRENAL | 26.83 | 26.62 | 9.445 | 1.755 | 0.296273193 |
| D2 | MetAP1 ADRENAL | 26.41 | | | | |
| E2 | MetAP2 ADRENAL | 21.97 | 21.68 | 4.505 | -3.19 | 9.094535786 |
| F2 | MetAP2 ADRENAL | 21.39 | | | | |
| G2 | MetAP3 ADRENAL | 24.83 | 24.865 | 7.69 | 0 | 1 |
| H2 | MetAP3 ADRENAL | 24.9 | | | | |
| A3 | CYCLOPHILIN UTERUS | 17.96 | 17.83 | 0 | | |
| B3 | CYCLOPHILIN UTERUS | 17.7 | | | | |
| C3 | MetAP1 UTERUS | 24.91 | 25.045 | 7.215 | -0.41 | 1.333298677 |
| D3 | MetAP1 UTERUS | 25.18 | | | | |
| E3 | MetAP2 UTERUS | 22.24 | 22.215 | 4.385 | -3.25 | 9.480742168 |
| F3 | MetAP2 UTERUS | 22.19 | | | | |
| G3 | MetAP3 UTERUS | 25.56 | 25.46 | 7.63 | 0 | 1 |
| H3 | MetAP3 UTERUS | 25.36 | | | | |
| A4 | CYCLOPHILIN HEART | 25.12 | 25.425 | 0 | | |
| B4 | CYCLOPHILIN HEART | 25.73 | | | | |
| C4 | MetAP1 HEART | 33.33 | 33.195 | 7.77 | -2.2 | 4.578896642 |
| D4 | MetAP1 HEART | 33.06 | | | | |
| E4 | MetAP2 HEART | 31.48 | 31.505 | 6.08 | -3.89 | 14.77411697 |
| F4 | MetAP2 HEART | 31.53 | | | | |
| G4 | MetAP3 HEART | 36.02 | 35.39 | 9.965 | 0 | 1 |
| H4 | MetAP3 HEART | 34.76 | | | | |
| A5 | CYCLOPHILIN PROSTATE | 17.21 | 17.28 | 0 | | |
| B5 | CYCLOPHILIN PROSTATE | 17.35 | | | | |
| C5 | MetAP1 PROSTATE | 24.27 | 24.235 | 6.955 | -1.3 | 2.462288827 |
| D5 | MetAP1 PROSTATE | 24.2 | | | | |
| E5 | MetAP2 PROSTATE | 22.48 | 22.31 | 5.03 | -3.23 | 9.350217988 |
| F5 | MetAP2 PROSTATE | 22.14 | | | | |
| G5 | MetAP3 PROSTATE | 25.61 | 25.535 | 8.255 | 0 | 1 |
| H5 | MetAP3 PROSTATE | 25.46 | | | | |
| A6 | CYCLOPHILIN SMALL INTESTIN | 18.07 | 18.085 | 0 | | |
| B6 | CYCLOPHILIN SMALL INTESTIN | 18.1 | | | | |
| C6 | MetAP1 SMALL INTESTINE | 25.19 | 25.17 | 7.085 | -0.4 | 1.319507911 |
| D6 | MetAP1 SMALL INTESTINE | 25.15 | | | | |
| E6 | MetAP2 SMALL INTESTINE | 22.47 | 22.645 | 4.56 | -2.93 | 7.594736968 |
| F6 | MetAP2 SMALL INTESTINE | 22.82 | | | | |
| G6 | MetAP3 SMALL INTESTINE | 25.72 | 25.57 | 7.485 | 0 | 1 |
| H6 | MetAP3 SMALL INTESTINE | 25.42 | | | | |
| A7 | CYCLOPHILIN CEREBELLUM | 17.57 | 17.65 | 0 | | |
| B7 | CYCLOPHILIN CEREBELLUM | 17.73 | | | | |
| C7 | MetAP1 CEREBELLUM | 25.62 | 25.48 | 7.83 | -0.41 | 1.333298677 |
| D7 | MetAP1 CEREBELLUM | 25.34 | | | | |
| E7 | MetAP2 CEREBELLUM | 22.27 | 22.32 | 4.67 | -3.58 | 11.9174197 |
| F7 | MetAP2 CEREBELLUM | 22.37 | | | | |
| G7 | MetAP3 CEREBELLUM | 25.98 | 25.895 | 8.245 | 0 | 1 |
| H7 | MetAP3 CEREBELLUM | 25.81 | | | | |

*FIG. 12A*

| WELL | SAMPLE NAME | CT | AVGCT | DCT | DDCT | FOLD EXPRESSION |
|---|---|---|---|---|---|---|
| A8 | CYCLOPHILIN LUNG | 22.13 | 22.17 | 0 | | |
| B8 | CYCLOPHILIN LUNG | 22.21 | | | | |
| C8 | MetAP1 LUNG | 32.13 | 32.175 | 10.005 | -0.42 | 1.337927555 |
| D8 | MetAP1 LUNG | 32.22 | | | | |
| E8 | MetAP2 LUNG | 29.48 | 29.32 | 7.15 | -3.28 | 9.679952714 |
| F8 | MetAP2 LUNG | 29.16 | | | | |
| G8 | MetAP3 LUNG | 32.76 | 32.595 | 10.425 | 0 | 1 |
| H8 | MetAP3 LUNG | 32.43 | | | | |
| A9 | CYCLOPHILIN BONE MARROW | 17.53 | 17.57 | 0 | | |
| B9 | CYCLOPHILIN BONE MARROW | 17.61 | | | | |
| C9 | MetAP1 BONE MARROW | 25.47 | 25.415 | 7.845 | -0.41 | 1.328685814 |
| D9 | MetAP1 BONE MARROW | 25.36 | | | | |
| E9 | MetAP2 BONE MARROW | 21.94 | 21.775 | 4.205 | -4.05 | 16.56423878 |
| F9 | MetAP2 BONE MARROW | 21.61 | | | | |
| G9 | MetAP3 BONE MARROW | 26.02 | 25.825 | 8.255 | 0 | 1 |
| H9 | MetAP3 BONE MARROW | 25.63 | | | | |
| A10 | CYCLOPHILIN COLON | 17.21 | 17.3 | 0 | | |
| B10 | CYCLOPHILIN COLON | 17.39 | | | | |
| C10 | MetAP1 COLON | 25.01 | 25.05 | 7.75 | -1.71 | 3.271608234 |
| D10 | MetAP1 COLON | 25.09 | | | | |
| E10 | MetAP2 COLON | 22.68 | 22.595 | 5.295 | -4.17 | 17.93865725 |
| F10 | MetAP2 COLON | 22.51 | | | | |
| G10 | MetAP3 COLON | 27.06 | 26.76 | 9.46 | 0 | 1 |
| H10 | MetAP3 COLON | 26.46 | | | | |
| A11 | CYCLOPHILIN SPINAL CHORD | 17.06 | 17.02 | 0 | | |
| B11 | CYCLOPHILIN SPINAL CHORD | 16.98 | | | | |
| C11 | MetAP1 SPINAL CHORD | 25.41 | 25.495 | 8.475 | 0.39 | 0.763129604 |
| D11 | MetAP1 SPINAL CHORD | 25.58 | | | | |
| E11 | MetAP2 SPINAL CHORD | 21.29 | 21.26 | 4.24 | -3.85 | 14.37011797 |
| F11 | MetAP2 SPINAL CHORD | 21.23 | | | | |
| G11 | MetAP3 SPINAL CHORD | 25.22 | 25.105 | 8.085 | 0 | 1 |
| H11 | MetAP3 SPINAL CHORD | 24.99 | | | | |
| 2-10-00#1 | | | | | | |
| A1 | CYCLOPHILIN SMALL INTESTIN | 18.11 | 18.175 | 0 | | |
| B1 | CYCLOPHILIN SMALL INTESTIN | 18.24 | | | | |
| C1 | MetAP1 SMALL INTESTINE | 25.14 | 25.185 | 7.01 | -0.72 | 1.652900636 |
| D1 | MetAP1 SMALL INTESTINE | 25.23 | | | | |
| E1 | MetAP2 SMALL INTESTINE | 22.42 | 22.5 | 4.325 | -3.41 | 10.62948651 |
| F1 | MetAP2 SMALL INTESTINE | 22.58 | | | | |
| G1 | MetAP3 SMALL INTESTINE | 26.01 | 25.91 | 7.735 | 0 | 1 |
| H1 | MetAP3 SMALL INTESTINE | 25.81 | | | | |
| A2 | CYCLOPHILIN TESTIS | 17.5 | 17.465 | 0 | | |
| B2 | CYCLOPHILIN TESTIS | 17.43 | | | | |
| C2 | MetAP1 TESTIS | 22.5 | 22.47 | 5.005 | -2.43 | 5.388934307 |
| D2 | MetAP1 TESTIS | 22.44 | | | | |
| E2 | MetAP2 TESTIS | 19.81 | 19.84 | 2.375 | -5.06 | 33.35890435 |
| F2 | MetAP2 TESTIS | 19.87 | | | | |
| G2 | MetAP3 TESTIS | 24.99 | 24.9 | 7.435 | 0 | 1 |
| H2 | MetAP3 TESTIS | 24.81 | | | | |
| A3 | CYCLOPHILIN HEART | 17.87 | 17.83 | 0 | | |
| B3 | CYCLOPHILIN HEART | 17.79 | | | | |
| C3 | MetAP1 HEART | 24.12 | 23.99 | 6.16 | -1.19 | 2.281527432 |
| D3 | MetAP1 HEART | 23.86 | | | | |
| E3 | MetAP2 HEART | 21.05 | 21.095 | 3.265 | -4.09 | 16.97100386 |
| F3 | MetAP2 HEART | 21.14 | | | | |
| G3 | MetAP3 HEART | 25.25 | 25.18 | 7.35 | 0 | 1 |
| H3 | MetAP3 HEART | 25.11 | | | | |

*FIG. 12B*

| WELL | SAMPLE NAME | CT | AVGCT | DCT | DDCT | FOLD EXPRESSION |
|---|---|---|---|---|---|---|
| A4 | CYCLOPHILIN LIVER | 17.83 | 17.805 | 0 | | |
| B4 | CYCLOPHILIN LIVER | 17.78 | | | | |
| C4 | MetAP1 LIVER | 25.13 | 25.165 | 7.36 | -0.23 | 1.176906737 |
| D4 | MetAP1 LIVER | 25.2 | | | | |
| E4 | MetAP2 LIVER | 21.57 | 21.66 | 3.855 | -3.74 | 13.36140671 |
| F4 | MetAP2 LIVER | 21.75 | | | | |
| G4 | MetAP3 LIVER | 25.34 | 25.4 | 7.595 | 0 | 1 |
| H4 | MetAP3 LIVER | 25.46 | | | | |
| A5 | CYCLOPHILIN THYMUS | 17.2 | 17.21 | 0 | | |
| B5 | CYCLOPHILIN THYMUS | 17.22 | | | | |
| C5 | MetAP1 THYMUS | 23.91 | 24.025 | 6.815 | -3.36 | 10.26740718 |
| D5 | MetAP1 THYMUS | 24.14 | | | | |
| E5 | MetAP2 THYMUS | 21.75 | 21.91 | 4.7 | -5.48 | 44.47738303 |
| F5 | MetAP2 THYMUS | 22.07 | | | | |
| G5 | MetAP3 THYMUS | 27.51 | 27.385 | 10.175 | 0 | 1 |
| H5 | MetAP3 THYMUS | 27.26 | | | | |
| A6 | CYCLOPHILIN BRAIN | 16.15 | 16.125 | 0 | | |
| B6 | CYCLOPHILIN BRAIN | 16.1 | | | | |
| C6 | MetAP1 BRAIN | 23.74 | 23.835 | 7.71 | -0.81 | 1.128964405 |
| D6 | MetAP1 BRAIN | 23.93 | | | | |
| E6 | MetAP2 BRAIN | 20.38 | 20.42 | 4.295 | -3.59 | 12.04197398 |
| F6 | MetAP2 BRAIN | 20.46 | | | | |
| G6 | MetAP3 BRAIN | 24.01 | 24.01 | 7.885 | 0 | 1 |
| H6 | MetAP3 BRAIN | 24.01 | | | | |
| A7 | CYCLOPHILIN FETAL BRAIN | 17.09 | 17.205 | 0 | | |
| B7 | CYCLOPHILIN FETAL BRAIN | 17.32 | | | | |
| C7 | MetAP1 FETAL BRAIN | 24.11 | 23.79 | 6.585 | 0.88 | 0.543367431 |
| C7 | MetAP1 FETAL BRAIN | 23.47 | | | | |
| E7 | MetAP2 FETAL BRAIN | 21.38 | 21.36 | 4.155 | -1.55 | 2.928171392 |
| F7 | MetAP2 FETAL BRAIN | 21.34 | | | | |
| G7 | MetAP3 FETAL BRAIN | 23.04 | 22.91 | 5.705 | 0 | 1 |
| H7 | MetAP3 FETAL BRAIN | 22.78 | | | | |
| A8 | CYCLOPHILIN SALIVARY | 18.29 | 18.31 | 0 | | |
| B8 | CYCLOPHILIN SALIVARY | 18.33 | | | | |
| C8 | MetAP1 SALIVARY | 25.35 | 25.47 | 7.16 | -0.27 | 1.205807828 |
| D8 | MetAP1 SALIVARY | 25.59 | | | | |
| E8 | MetAP2 SALIVARY | 22.4 | 22.415 | 4.105 | -3.33 | 10.02131551 |
| F8 | MetAP2 SALIVARY | 22.43 | | | | |
| G8 | MetAP3 SALIVARY | 25.76 | 25.74 | 7.43 | 0 | 1 |
| H8 | MetAP3 SALIVARY | 25.72 | | | | |
| A9 | CYCLOPHILIN MUSCLE | 19.8 | 19.85 | 0 | | |
| B9 | CYCLOPHILIN MUSCLE | 19.9 | | | | |
| C9 | MetAP1 MUSCLE | 25.11 | 25.095 | 5.245 | 3.615 | 0.081616237 |
| D9 | MetAP1 MUSCLE | 25.08 | | | | |
| E9 | MetAP2 MUSCLE | 21.43 | 21.48 | 1.63 | -3.52 | 11.47164198 |
| F9 | MetAP2 MUSCLE | 21.53 | | | | |
| G9 | MetAP3 MUSCLE | 25 | 25 | 5.15 | 0 | 1 |
| H9 | MetAP3 MUSCLE | 25 | | | | |
| A10 | CYCLOPHILIN SPLEEN | 17.33 | 17.365 | 0 | | |
| B10 | CYCLOPHILIN SPLEEN | 17.4 | | | | |
| C10 | MetAP1 SPLEEN | 24.95 | 25.01 | 7.645 | -0.14 | 1.098092814 |
| D10 | MetAP1 SPLEEN | 25.07 | | | | |
| E10 | MetAP2 SPLEEN | 22.01 | 22 | 4.635 | -3.15 | 8.845845227 |
| F10 | MetAP2 SPLEEN | 21.99 | | | | |
| G10 | MetAP3 SPLEEN | 25 | 25.145 | 7.78 | 0 | 1 |
| H10 | MetAP3 SPLEEN | 25.29 | | | | |

*FIG. 13A*

| WELL | SAMPLE NAME | CT | AVGCT | DCT | DDCT | FOLD EXPRESSION |
|---|---|---|---|---|---|---|
| A11 | CYCLOPHILIN BRAIN | 16.46 | 16.445 | 0 | | |
| B11 | CYCLOPHILIN BRAIN | 16.43 | | | | |
| C11 | MetAP1 BRAIN | 24.22 | 24.27 | 7.825 | -0.07 | 1.049716684 |
| D11 | MetAP1 BRAIN | 24.32 | | | | |
| E11 | MetAP2 BRAIN | 21.13 | 21.15 | 4.705 | -3.19 | 9.126109727 |
| F11 | MetAP2 BRAIN | 21.17 | | | | |
| G11 | MetAP3 BRAIN | 24.37 | 24.34 | 7.895 | 0 | 1 |
| H11 | MetAP3 BRAIN | 24.31 | | | | |
| 2-10-00#2 | | | | | | |
| A1 | CYCLOPHILIN SMALL INTESTIN | 18.07 | 18.12 | 0 | | |
| B1 | CYCLOPHILIN SMALL INTESTIN | 18.17 | | | | |
| C1 | MetAP1 SMALL INTESTINE | 25.39 | 25.355 | 7.235 | -0.39 | 1.305859787 |
| D1 | MetAP1 SMALL INTESTINE | 25.32 | | | | |
| E1 | MetAP2 SMALL INTESTINE | 23.12 | 23.12 | 5 | -2.62 | 6.147500725 |
| F1 | MetAP2 SMALL INTESTINE | 23.12 | | | | |
| G1 | MetAP3 SMALL INTESTINE | 25.98 | 25.74 | 7.62 | 0 | 1 |
| H1 | MetAP3 SMALL INTESTINE | 25.5 | | | | |
| A2 | CYCLOPHILIN THYROID | 17.84 | 17.82 | 0 | | |
| B2 | CYCLOPHILIN THYROID | 17.8 | | | | |
| C2 | MetAP1 THYROID | 25.9 | 25.94 | 8.12 | -0.3 | 1.226884977 |
| D2 | MetAP1 THYROID | 25.98 | | | | |
| E2 | MetAP2 THYROID | 23.07 | 22.94 | 5.12 | -3.3 | 9.815079818 |
| F2 | MetAP2 THYROID | 22.81 | | | | |
| G2 | MetAP3 THYROID | 26.24 | 26.235 | 8.415 | 0 | 1 |
| H2 | MetAP3 THYROID | 26.23 | | | | |
| A3 | CYCLOPHILIN MAMMARY | 18.31 | 18.025 | 0 | | |
| B3 | CYCLOPHILIN MAMMARY | 17.74 | | | | |
| C3 | MetAP1 MAMMARY | 25.36 | 25.3 | 7.275 | 0.48 | 0.716977624 |
| D3 | MetAP1 MAMMARY | 25.24 | | | | |
| E3 | MetAP2 MAMMARY | 22.3 | 22.285 | 4.26 | -2.54 | 5.795768618 |
| F3 | MetAP2 MAMMARY | 22.27 | | | | |
| G3 | MetAP3 MAMMARY | 24.76 | 24.82 | 6.795 | 0 | 1 |
| H3 | MetAP3 MAMMARY | 24.88 | | | | |
| A4 | CYCLOPHILIN PLACENTA | 18.67 | 18.55 | 0 | | |
| B4 | CYCLOPHILIN PLACENTA | 18.43 | | | | |
| C4 | MetAP1 PLACENTA | 26.72 | 26.535 | 7.985 | -0.18 | 1.132883885 |
| D4 | MetAP1 PLACENTA | 26.35 | | | | |
| E4 | MetAP2 PLACENTA | 22.93 | 22.77 | 4.22 | -3.95 | 15.40151109 |
| F4 | MetAP2 PLACENTA | 22.61 | | | | |
| G4 | MetAP3 PLACENTA | 26.66 | 26.715 | 8.165 | 0 | 1 |
| H4 | MetAP3 PLACENTA | 26.77 | | | | |
| A5 | CYCLOPHILIN FETAL LIVER | 17.68 | 17.835 | 0 | | |
| B5 | CYCLOPHILIN FETAL LIVER | 17.99 | | | | |
| C5 | MetAP1 FETAL LIVER | 25.5 | 25.635 | 7.8 | 0.14 | 0.907519155 |
| D5 | MetAP1 FETAL LIVER | 25.77 | | | | |
| E5 | MetAP2 FETAL LIVER | 21.96 | 21.805 | 3.97 | -3.69 | 12.90626815 |
| F5 | MetAP2 FETAL LIVER | 21.65 | | | | |
| G5 | MetAP3 FETAL LIVER | 25.59 | 25.495 | 7.66 | 0 | 1 |
| H5 | MetAP3 FETAL LIVER | 25.4 | | | | |
| A6 | CYCLOPHILIN TRACHEA | 18.79 | 18.84 | 0 | | |
| B6 | CYCLOPHILIN TRACHEA | 18.89 | | | | |
| C6 | MetAP1 TRACHEA | 26.12 | 25.895 | 7.055 | -0.49 | 1.404444876 |
| D6 | MetAP1 TRACHEA | 25.67 | | | | |
| E6 | MetAP2 TRACHEA | 24.31 | 24.2 | 5.36 | -2.19 | 4.547267893 |
| F6 | MetAP2 TRACHEA | 24.09 | | | | |
| G6 | MetAP3 TRACHEA | 26.26 | 26.385 | 7.545 | 0 | 1 |
| H6 | MetAP3 TRACHEA | 26.51 | | | | |

*FIG. 13B*

| WELL | SAMPLE NAME | CT | AVGCT | DCT | DDCT | FOLD EXPRESSION |
|---|---|---|---|---|---|---|
| A7 | CYCLOPHILIN PANCREAS | 20.25 | 20.22 | 0 | | |
| B7 | CYCLOPHILIN PANCREAS | 20.19 | | | | |
| C7 | MetAP1 PANCREAS | 28.05 | 27.98 | 7.76 | 0.855 | 0.552865327 |
| D7 | MetAP1 PANCREAS | 27.91 | | | | |
| E7 | MetAP2 PANCREAS | 25.12 | 25.035 | 4.815 | -2.09 | 4.25748073 |
| F7 | MetAP2 PANCREAS | 24.95 | | | | |
| G7 | MetAP3 PANCREAS | 27.24 | 27.125 | 6.905 | 0 | 1 |
| H7 | MetAP3 PANCREAS | 27.01 | | | | |
| A8 | CYCLOPHILIN STOMACH | 19.86 | 19.965 | 0 | | |
| B8 | CYCLOPHILIN STOMACH | 20.07 | | | | |
| C8 | MetAP1 STOMACH | 27.48 | 27.225 | 7.26 | -0 | 1.003471749 |
| D8 | MetAP1 STOMACH | 26.97 | | | | |
| E8 | MetAP2 STOMACH | 24.61 | 24.475 | 4.51 | -2.76 | 6.750526369 |
| F8 | MetAP2 STOMACH | 24.34 | | | | |
| G8 | MetAP3 STOMACH | 27.37 | 27.23 | 7.265 | 0 | 1 |
| H8 | MetAP3 STOMACH | 27.09 | | | | |
| 2-9-00#1 | | | | | | |
| A6 | CYCLOPHILIN SMALL INTESTIN | 18.07 | 18.085 | 0 | | |
| B6 | CYCLOPHILIN SMALL INTESTIN | 18.1 | | | | |
| C6 | MetAP1 SMALL INTESTINE | 25.19 | 25.17 | 7.085 | -0.55 | 1.464085696 |
| D6 | MetAP1 SMALL INTESTINE | 25.15 | | | | |
| E6 | MetAP2 SMALL INTESTINE | 22.47 | 22.645 | 4.56 | -3.08 | 8.426888288 |
| F6 | MetAP2 SMALL INTESTINE | 22.82 | | | | |
| G6 | MetAP3 SMALL INTESTINE | 25.72 | 25.57 | 7.635 | 0 | 1 |
| H6 | MetAP3 SMALL INTESTINE | 25.42 | | | | |
| 2-10-00#1 | | | | | | |
| A1 | CYCLOPHILIN SMALL INTESTIN | 18.11 | 18.175 | 0 | | |
| B1 | CYCLOPHILIN SMALL INTESTIN | 18.24 | | | | |
| C1 | MetAP1 SMALL INTESTINE | 25.14 | 25.185 | 7.01 | -0.72 | 1.652900636 |
| D1 | MetAP1 SMALL INTESTINE | 25.23 | | | | |
| E1 | MetAP2 SMALL INTESTINE | 22.42 | 22.5 | 4.325 | -3.41 | 10.62948651 |
| F1 | MetAP2 SMALL INTESTINE | 22.58 | | | | |
| G1 | MetAP3 SMALL INTESTINE | 26.01 | 25.91 | 7.735 | 0 | 1 |
| H1 | MetAP3 SMALL INTESTINE | 25.81 | | | | |
| 2-10-00#2 | | | | | | |
| A1 | CYCLOPHILIN SMALL INTESTIN | 18.07 | 18.12 | 0 | | |
| B1 | CYCLOPHILIN SMALL INTESTIN | 18.17 | | | | |
| C1 | MetAP1 SMALL INTESTINE | 25.39 | 25.355 | 7.235 | -0.39 | 1.305859787 |
| D1 | MetAP1 SMALL INTESTINE | 25.32 | | | | |
| E1 | MetAP2 SMALL INTESTINE | 23.12 | 23.12 | 5 | -2.62 | 6.147500725 |
| F1 | MetAP2 SMALL INTESTINE | 23.12 | | | | |
| G1 | MetAP3 SMALL INTESTINE | 25.98 | 25.74 | 7.62 | 0 | 1 |
| H1 | MetAP3 SMALL INTESTINE | 25.5 | | | | |

*FIG. 14*

| WELL | TYPE | SAMPLE NAME | CT | AVGCT | DCT | DDCT | FOLD EXPRESSION |
|---|---|---|---|---|---|---|---|
| A1 | UNKN | CYCLOPHILIN HIPPOCAMPUS | 15.23 | 15.24 | | | |
| B1 | UNKN | CYCLOPHILIN HIPPOCAMPUS | 15.25 | | | | |
| A2 | UNKN | CYCLOPHILIN FETAL WHOLE | 16.12 | 16.1 | | | |
| B2 | UNKN | CYCLOPHILIN FETAL WHOLE | 16.08 | | | | |
| A3 | UNKN | CYCLOPHILIN THALAMUS | 16.47 | 16.445 | | | |
| B3 | UNKN | CYCLOPHILIN THALAMUS | 16.42 | | | | |
| A4 | UNKN | CYCLOPHILIN CEREBELLUM | 15.6 | 15.6 | | | |
| B4 | UNKN | CYCLOPHILIN CEREBELLUM | 15.6 | | | | |
| A5 | UNKN | CYCLOPHILIN ADULT WHOLE | 15.24 | 15.25 | | | |
| B5 | UNKN | CYCLOPHILIN ADULT WHOLE | 15.26 | | | | |
| A6 | UNKN | CYCLOPHILIN AMYGDALA | 16.35 | 16.365 | | | |
| B6 | UNKN | CYCLOPHILIN AMYGDALA | 16.38 | | | | |
| A7 | UNKN | CYCLOPHILIN SUBSTANTIA NIGER | 15.62 | 15.55 | | | |
| B7 | UNKN | CYCLOPHILIN SUBSTANTIA NIGER | 15.48 | | | | |
| A8 | UNKN | CYCLOPHILIN CAUDATE NUCLEUS | 16.71 | 16.67 | | | |
| B8 | UNKN | CYCLOPHILIN CAUDATE NUCLEUS | 16.63 | | | | |
| C1 | UNKN | MetAP1 HIPPOCAMPUS | 23.07 | 23.04 | 7.8 | -0.76 | 1.693490625 |
| D1 | UNKN | MetAP1 HIPPOCAMPUS | 23.01 | | | | |
| C2 | UNKN | MetAP1 FETAL WHOLE | 22.32 | 22.53 | 6.43 | -2.13 | 4.377174805 |
| D2 | UNKN | MetAP1 FETAL WHOLE | 22.74 | | | | |
| C3 | UNKN | MetAP1 THALAMUS | 25.15 | 25.005 | 8.56 | 0 | 1 |
| D3 | UNKN | MetAP1 THALAMUS | 24.86 | | | | |
| C4 | UNKN | MetAP1 CEREBELLUM | 22.52 | 22.675 | 7.075 | -1.485 | 2.799171731 |
| D4 | UNKN | MetAP1 CEREBELLUM | 22.83 | | | | |
| C5 | UNKN | MetAP1 ADULT WHOLE | 22.67 | 22.68 | 7.43 | -1.13 | 2.188587403 |
| D5 | UNKN | MetAP1 ADULT WHOLE | 22.69 | | | | |
| C6 | UNKN | MetAP1 AMYGDALA | 23.68 | 23.835 | 7.47 | -1.09 | 2.128740365 |
| D6 | UNKN | MetAP1 AMYGDALA | 23.99 | | | | |
| C7 | UNKN | MetAP1 SUBSTANTIA NIGER | 23.49 | 23.4 | 7.85 | -0.71 | 1.635804117 |
| D7 | UNKN | MetAP1 SUBSTANTIA NIGER | 23.31 | | | | |
| C8 | UNKN | MetAP1 CAUDATE NUCLEUS | 24.16 | 24.165 | 7.495 | -1.065 | 2.09216988 |
| D8 | UNKN | MetAP1 CAUDATE NUCLEUS | 24.17 | | | | |
| E1 | UNKN | MetAP2 HIPPOCAMPUS | 20.32 | 20.29 | 5.05 | -0.415 | 1.333298677 |
| F1 | UNKN | MetAP2 HIPPOCAMPUS | 20.26 | | | | |
| E2 | UNKN | MetAP2 FETAL WHOLE | 20.79 | 20.76 | 4.66 | -0.805 | 1.747145792 |
| F2 | UNKN | MetAP2 FETAL WHOLE | 20.73 | | | | |
| E3 | UNKN | MetAP2 THALAMUS | 21.87 | 21.895 | 5.45 | -0.015 | 1.010451446 |
| F3 | UNKN | MetAP2 THALAMUS | 21.92 | | | | |
| E4 | UNKN | MetAP2 CEREBELLUM | 19.98 | 19.955 | 4.355 | -1.11 | 2.158456473 |
| F4 | UNKN | MetAP2 CEREBELLUM | 19.93 | | | | |
| E5 | UNKN | MetAP2 ADULT WHOLE | 20.97 | 20.715 | 5.465 | 0 | 1 |
| F5 | UNKN | MetAP2 ADULT WHOLE | 20.46 | | | | |
| E6 | UNKN | MetAP2 AMYGDALA | 21.73 | 21.68 | 5.315 | -0.15 | 1.109569472 |
| F6 | UNKN | MetAP2 AMYGDALA | 21.63 | | | | |
| E7 | UNKN | MetAP2 SUBSTANTIA NIGER | 20.15 | 20.11 | 4.56 | -0.905 | 1.872544495 |
| F7 | UNKN | MetAP2 SUBSTANTIA NIGER | 20.07 | | | | |
| E8 | UNKN | MetAP2 CAUDATE NUCLEUS | 21.76 | 21.585 | 4.915 | -0.55 | 1.464085696 |
| F8 | UNKN | MetAP2 CAUDATE NUCLEUS | 21.41 | | | | |

*FIG. 15A*

| WELL | TYPE | SAMPLE NAME | CT | AVGCT | DCT | DDCT | FOLD EXPRESSION |
|---|---|---|---|---|---|---|---|
| G1 | UNKN | MetAP3 HIPPOCAMPUS | 24.01 | 23.835 | 8.595 | -0.98 | 1.972465409 |
| H1 | UNKN | MetAP3 HIPPOCAMPUS | 23.66 | | | | |
| G2 | UNKN | MetAP3 FETAL WHOLE | 22.73 | 22.66 | 6.56 | -3.015 | 8.083611572 |
| H2 | UNKN | MetAP3 FETAL WHOLE | 22.59 | | | | |
| G3 | UNKN | MetAP3 THALAMUS | 25.4 | 25.395 | 8.95 | -0.625 | 1.542210825 |
| H3 | UNKN | MetAP3 THALAMUS | 25.39 | | | | |
| G4 | UNKN | MetAP3 CEREBELLUM | 24.24 | 24.175 | 8.575 | -1 | 2 |
| H4 | UNKN | MetAP3 CEREBELLUM | 24.11 | | | | |
| G5 | UNKN | MetAP3 ADULT WHOLE | 25.33 | 24.825 | 9.575 | 0 | 1 |
| H5 | UNKN | MetAP3 ADULT WHOLE | 24.32 | | | | |
| G6 | UNKN | MetAP3 AMYGDALA | 25 | 24.89 | 8.525 | -1.05 | 2.070529848 |
| H6 | UNKN | MetAP3 AMYGDALA | 24.78 | | | | |
| G7 | UNKN | MetAP3 SUBSTANTIA NIGER | 24.03 | 23.965 | 8.415 | -1.16 | 2.234574276 |
| H7 | UNKN | MetAP3 SUBSTANTIA NIGER | 23.9 | | | | |
| G8 | UNKN | MetAP3 CAUDATE NUCLEUS | 25.35 | 25.325 | 8.655 | -0.92 | 1.892115293 |
| H8 | UNKN | MetAP3 CAUDATE NUCLEUS | 25.3 | | | | |
| A9 | NTC | CYCLOPHILIN | 40 | | | | |
| B9 | NTC | CYCLOPHILIN | 40 | | | | |
| C9 | NTC | MetAP1 | 40 | | | | |
| D9 | NTC | MetAP1 | 40 | | | | |
| E9 | NTC | MetAP2 | 40 | | | | |
| F9 | NTC | MetAP2 | 40 | | | | |
| G9 | NTC | MetAP3 | 40 | | | | |
| H9 | NTC | MetAP3 | 40 | | | | |

FIG. 15B

SEQUENCE LISTING

<160> NUMBER OF SEQ ID NOS: 62

<210> SEQ ID NO 1
<211> LENGTH: 2671
<212> TYPE: DNA
<213> ORGANISM: homo sapiens MetAP1

<400> SEQUENCE: 1

```
ggcgctcttc cagcgggcag gcagcatggc ggccgtggag acgcgggtgt gcgagacaga      60
cggctgcagc agtgaggcca agctccagtg tcccacttgc atcaagctgg gcatccaggg     120
ctcgtacttc tgctcgcagg aatgttttaa aggaagttgg gctactcaca agttactaca     180
taagaaagca aaagatgaaa aggcgaagcg agaagtgtct tcctggactg tggaaggtga     240
tattaatact gacccatggg caggttatcg atatactggt aaactcagac cacattatcc     300
actgatgcca acaaggccag tgccaagtta tattcaaaga ccagattatg ctgatcatcc     360
cttaggaatg tctgaatctg aacaggctct taaaggtact tctcagatta aattactctc     420
atctgaagat ataagaggga tgcgacttgt atgtaggctt gctagagaag ttttggatgt     480
tgctgccggc atgattaaac caggtgtaac tactgaagaa atagatcacg ctgtacactt     540
agcatgtatt gcaagaaatt gctacccttc tccctgaat tattataatt tcccaaagtc     600
ttgttgtacc tcagtgaatg aagtcatttg ccatggaata ccagacagaa ggcccttaca     660
agaaggtgac attgttaatg tggatatcac tctttatcgc aatggttatc atggggacct     720
gaatgagaca ttttttgttg gagaagtgga tgatggagca cggaaacttg ttcagaccac     780
atatgagtgc ctgatgcaag ccattgatgc agtgaagcct ggtgttcggt acagagaatt     840
gggaaacatt atccagaagc atgcccaagc aaatgggttt tcagttgttc gaagctattg     900
tgggcatgga atccacaagc tttttcatac agctcccaat gtaccccact atgctaaaaa     960
taaagcagtt ggagtgatga agtcgggcca tgtatttaca attgagccaa tgatttgtga    1020
aggcggatgg caggatgaaa cctggccaga tggttggact gcggtgacaa gagacggaaa    1080
gcggtctgct cagtttgagc acaccctcct ggtcacagac actggctgtg aaatcctaac    1140
ccggcgactt gacagtgcac ggcctcactt catgtctcaa ttttaatttc tcccaagatg    1200
```

-continued

```
gcacatctca gtaccttctt actgtgctat gcattttatt gagagtacag aaaggaagag    1260
gaaccttttt ttaatcactt gttttgtttt gactatagat aagaaaggac tacagcattt    1320
gatgtgtgtc ctcaagaact tgtcttgggt ctgaaaaagc tgagaagaat aaaggaaaca    1380
ttgctcaact cttcagcccc ctcccccctgc acacctgttt tctcatttgc cctttgagca    1440
cttttactta aacttgcttg tagttgcttt tatcactgcc gcaaaacagc catcaagagc    1500
catctgcttt ccaggtgaac attggaaatg agaatctttg aaacttagca atatgtgttg    1560
caccagattt tttaaattat atatatggaa atatatatgt atacatttta agttctgtat    1620
acataattac caaacactat gtgacctgga gtttgtgttg tttctgctct gacaggttta    1680
tatgttctta caaatggatc catagtttgc agtgatttaa ttcctggttg ggatttggcc    1740
tcccctctcc cccatgctaa ttatttaccc ttgtaattgt gcatagggaa gcactcaccc    1800
aatgagactt tctccaatgt ggactctgtg tgtcagtgaa tgaatgtagt aaaattcact    1860
ttggaaggtt atcaggcttt taaaaatcta gtttatggca aaaatagcca ttttccaagt    1920
ggtggctgac tgttgcaggg aatgagaatt tcataataca ctgctatttc agacctctgt    1980
ttggtcagaa atggaaaaga aaaagccccc tttcttccct tttctgtttt acttcaaggg    2040 catacctttgg aggtgctcag agaagcgtga agtttgcact atggtggagg atggggaaag    2100
agttctaaag tgtctccagc tgtgaaccca ggaggtcaag tgggctatta aaatctaacg    2160
ttgagtaaat gtgatagtga tgagaaagga attttgtgta ctgtaacctt gcagtagaga    2220
tgcagctgtc cttcgtgtgt ggaaacacac ctctccttta catagttggg aacctcatta    2280
gaaatgacct cagctgcccc atatctacgt tcctttcagc agttgtccaa gtaggagtgt    2340
atccagtgaa gacatatcaa atcacaaagt cattgtcatt agagtgtact tgattactgg    2400
gcatccttgt aatataattt cataccactg acacattata cttgtaagag aacatctttc    2460
ccagagtgcc tcagaccta tgctttaaa atataataat gttttcatta cttttattat    2520
ttgaatgatt tagtaaagtt gactgaatct ggtatagact ttgggagtat gtgtgtgaag    2580
tttttatcaa actgtaatat ttgtgaatgg aatgccttgc aatatgaatg ttaatataat    2640
gtgtaaaggg agattaaaaa gtttgaatga t                                  2671
```

<210> SEQ ID NO 2
<211> LENGTH: 394
<212> TYPE: PRT
<213> ORGANISM: homo sapiens MetAP1

<400> SEQUENCE: 2

```
Ala Leu Phe Gln Arg Ala Gly Ser Met Ala Ala Val Glu Thr Arg Val
 1               5                  10                  15

Cys Glu Thr Asp Gly Cys Ser Ser Glu Ala Lys Leu Gln Cys Pro Thr
                20                  25                  30

Cys Ile Lys Leu Gly Ile Gln Gly Ser Tyr Phe Cys Ser Gln Glu Cys
            35                  40                  45

Phe Lys Gly Ser Trp Ala Thr His Lys Leu Leu His Lys Lys Ala Lys
        50                  55                  60

Asp Glu Lys Ala Lys Arg Glu Val Ser Ser Trp Thr Val Glu Gly Asp
65                  70                  75                  80

Ile Asn Thr Asp Pro Trp Ala Gly Tyr Arg Tyr Thr Gly Lys Leu Arg
                85                  90                  95

Pro His Tyr Pro Leu Met Pro Thr Arg Pro Val Pro Ser Tyr Ile Gln
               100                 105                 110
```

```
Arg Pro Asp Tyr Ala Asp His Pro Leu Gly Met Ser Glu Ser Glu Gln
        115                 120                 125
Ala Leu Lys Gly Thr Ser Gln Ile Lys Leu Leu Ser Ser Glu Asp Ile
    130                 135                 140
Glu Gly Met Arg Leu Val Cys Arg Leu Ala Arg Glu Val Leu Asp Val
145                 150                 155                 160
Ala Ala Gly Met Ile Lys Pro Gly Val Thr Thr Glu Glu Ile Asp His
                165                 170                 175
Ala Val His Leu Ala Cys Ile Ala Arg Asn Cys Tyr Pro Ser Pro Leu
            180                 185                 190
Asn Tyr Tyr Asn Phe Pro Lys Ser Cys Cys Thr Ser Val Asn Glu Val
        195                 200                 205
Ile Cys His Gly Ile Pro Asp Arg Arg Pro Leu Gln Glu Gly Asp Ile
    210                 215                 220
Val Asn Val Asp Ile Thr Leu Tyr Arg Asn Gly Tyr His Gly Asp Leu
225                 230                 235                 240
Asn Glu Thr Phe Phe Val Gly Glu Val Asp Asp Gly Ala Arg Lys Leu
                245                 250                 255
Val Gln Thr Thr Tyr Glu Cys Leu Met Gln Ala Ile Asp Ala Val Lys
            260                 265                 270
Pro Gly Val Arg Tyr Arg Glu Leu Gly Asn Ile Ile Gln Lys His Ala
        275                 280                 285
Gln Ala Asn Gly Phe Ser Val Val Arg Ser Tyr Cys Gly His Gly Ile
    290                 295                 300
His Lys Leu Phe His Thr Ala Pro Asn Val Pro His Tyr Ala Lys Asn
305                 310                 315                 320
Lys Ala Val Gly Val Met Lys Ser Gly His Val Phe Thr Ile Glu Pro
                325                 330                 335
Met Ile Cys Glu Gly Gly Trp Gln Asp Glu Thr Trp Pro Asp Gly Trp
            340                 345                 350
Thr Ala Val Thr Arg Asp Gly Lys Arg Ser Ala Gln Phe Glu His Thr
        355                 360                 365
Leu Leu Val Thr Asp Thr Gly Cys Glu Ile Leu Thr Arg Arg Leu Asp
    370                 375                 380
Ser Ala Arg Pro His Phe Met Ser Gln Phe
385                 390

<210> SEQ ID NO 3
<211> LENGTH: 1908
<212> TYPE: DNA
<213> ORGANISM: homo sapiens MetAP2

<400> SEQUENCE: 3
ctctgtctca ttccctcgcg ctctctcggg caacatggcg ggtgtggagg aggtagcggc      60
ctccgggagc cacctgaatg gcgacctgga tccagacgac agggaagaag gagctgcctc    120
tacggctgag gaagcagcca agaaaaaaag acgaaagaag aagaagagca agggccttc     180
tgcagcaggg gaacaggaac ctgataaaga atcaggagcc tcagtggatg aagtagcaag    240
acagttggaa agatcagcat tggaagataa agaaagagat gaagatgatg aagatggaga    300
tggcgatgga gatggagcaa ctggaaagaa gaagaaaaag aagaagaaga gagaggacc     360
aaaagttcaa acagaccctc cctcagttcc aatatgtgac ctgtatccta atggtgtatt    420
tcccaaagga caagaatgcg aatacccacc cacacaagat gggcgaacag ctgcttggag    480
```

-continued

| | |
|---|---|
| aactacaagt gaagaaaaga aagcattaga tcaggcaagt gaagagattt ggaatgattt | 540 |
| tcgagaagct gcagaagcac atcgacaagt tagaaaatac gtaatgagct ggatcaagcc | 600 |
| tgggatgaca atgatagaaa tctgtgaaaa gttggaagac tgttcacgca agttaataaa | 660 |
| agagaatgga ttaaatgcag gcctggcatt tcctactgga tgttctctca ataattgtgc | 720 |
| tgcccattat actcccaatg ccggtgacac aacagtatta cagtatgatg acatctgtaa | 780 |
| aatagacttt ggaacacata taagtggtag gattattgac tgtgctttta ctgtcacttt | 840 |
| taatcccaaa tatgatacgt tattaaaagc tgtaaaagat gctactaaca ctggaataaa | 900 |
| gtgtgctgga attgatgttc gtctgtgtga tgttggtgag ccatccaag aagttatgga | 960 |
| gtcctatgaa gttgaaatag atgggaagac atatcaagtg aaaccaatcc gtaatctaaa | 1020 |
| tggacattca attgggcaat atagaataca tgctggaaaa acagtgccga ttgtgaaagg | 1080 |
| agggaggca acaagaatgg aggaaggaga agtatatgca attgaaacct ttggtagtac | 1140 |
| aggaaaaggt gttgttcatg atgatatgga atgttcacat tacatgaaaa attttgatgt | 1200 |
| tggacatgtg ccaataaggc ttccaagaac aaaacacttg ttaaatgtca tcaatgaaaa | 1260 |
| ctttggaacc cttgccttct gccgcagatg gctggatcgc ttgggagaaa gtaaatactt | 1320 |
| gatggctctg aagaatctgt gtgacttggg cattgtagat ccatatccac cattatgtga | 1380 |
| cattaaagga tcatatacag cgcaatttga acataccatc ctgttgcgtc caacatgtaa | 1440 |
| agaagttgtc agcagaggag atgactatta aacttagtcc aaagccacct caacacctt | 1500 |
| attttctgag ctttgttgga aaacatgata ccagaattaa tttgccacat gttgtctgtt | 1560 |
| ttaacagtgg acccatgtaa tacttttatc catgtttaaa aagaaggaat ttggacaaag | 1620 |
| gcaaaccgtc taatgtaatt aaccaacgaa aaagctttcc ggactttaa atgctaactg | 1680 |
| ttttttcccct tcctgtctag gaaaatgcta taaagctcaa attagttagg aatgacttat | 1740 |
| acgttttgtt ttgaatacct aagagatact ttttggatat ttatattgcc atattcttac | 1800 |
| ttgaatgctt tgaatgacta catccagttc tgcacctata ccctctggtg ttgctttta | 1860 |
| accttcctgg aatccatttc taaaaaataa agacatttc agatctga | 1908 |

<210> SEQ ID NO 4
<211> LENGTH: 478
<212> TYPE: PRT
<213> ORGANISM: homo sapiens MetAP2

<400> SEQUENCE: 4

Met Ala Gly Val Glu Val Ala Ala Ser Gly Ser His Leu Asn Gly
1               5                   10                  15

Asp Leu Asp Pro Asp Asp Arg Glu Glu Gly Ala Ala Ser Thr Ala Glu
            20                  25                  30

Glu Ala Ala Lys Lys Lys Arg Arg Lys Lys Lys Ser Lys Gly Pro
        35                  40                  45

Ser Ala Ala Gly Glu Gln Glu Pro Asp Lys Glu Ser Gly Ala Ser Val
    50                  55                  60

Asp Glu Val Ala Arg Gln Leu Glu Arg Ser Ala Leu Glu Asp Lys Glu
65                  70                  75                  80

Arg Asp Glu Asp Asp Glu Asp Gly Asp Gly Asp Gly Asp Gly Ala Thr
                85                  90                  95

Gly Lys Lys Lys Lys Lys Lys Lys Lys Arg Gly Pro Lys Val Gln
            100                 105                 110

Thr Asp Pro Pro Ser Val Pro Ile Cys Asp Leu Tyr Pro Asn Gly Val
        115                 120                 125

Phe Pro Lys Gly Gln Glu Cys Glu Tyr Pro Pro Thr Gln Asp Gly Arg
    130                 135                 140

Thr Ala Ala Trp Arg Thr Thr Ser Glu Lys Lys Ala Leu Asp Gln
145                 150                 155                 160

Ala Ser Glu Glu Ile Trp Asn Asp Phe Arg Glu Ala Glu Ala His
                165                 170                 175

Arg Gln Val Arg Lys Tyr Val Met Ser Trp Ile Lys Pro Gly Met Thr
                180                 185                 190

Met Ile Glu Ile Cys Glu Lys Leu Glu Asp Cys Ser Arg Lys Leu Ile
                195                 200                 205

Lys Glu Asn Gly Leu Asn Ala Gly Leu Ala Phe Pro Thr Gly Cys Ser
210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
                260                 265                 270

Tyr Asp Thr Leu Leu Lys Ala Val Lys Asp Ala Thr Asn Thr Gly Ile
                275                 280                 285

Lys Cys Ala Gly Ile Asp Val Arg Leu Cys Asp Val Gly Glu Ala Ile
290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Gln Tyr
                325                 330                 335

Arg Ile His Ala Gly Lys Thr Val Pro Ile Val Lys Gly Gly Glu Ala
                340                 345                 350

Thr Arg Met Glu Glu Gly Glu Val Tyr Ala Ile Glu Thr Phe Gly Ser
                355                 360                 365

Thr Gly Lys Gly Val Val His Asp Asp Met Glu Cys Ser His Tyr Met
370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
                420                 425                 430

Lys Asn Leu Cys Asp Leu Gly Ile Val Asp Pro Tyr Pro Pro Leu Cys
435                 440                 445

Asp Ile Lys Gly Ser Tyr Thr Ala Gln Phe Glu His Thr Ile Leu Leu
450                 455                 460

Arg Pro Thr Cys Lys Glu Val Val Ser Arg Gly Asp Asp Tyr
465                 470                 475

<210> SEQ ID NO 5
<211> LENGTH: 3114
<212> TYPE: DNA
<213> ORGANISM: homo sapiens MetAP3 clone GT9D Insert
<220> FEATURE:
<221> NAME/KEY: misc_feature
<222> LOCATION: 1765, 1800, 2896, 2912, 2972, 2977, 2984, 2995, 3009,
      3040, 3073
<223> OTHER INFORMATION: n = A,T,C or G

<400> SEQUENCE: 5

-continued

```
cgccaacatg gcggcgccca gtggcgtcca cctgctcgtc cgcagaggta agcgcgtgga      60
ggagagcccc gtgagggttc gcacggttgc tcactaggtt ctcatagaat tttctcttca     120
ccactcaatc atatctactt acacaagcag tcaagcagta acaaagaag aaatttcttt      180
tttcggagac aaagagatat tcacacagt atagttttgc cggctgcagt ttcttcagct     240
catccggttc ctaagcacat aaagaagcca gactatgtga cgacaggcat tgtaccagac    300
tggggagaca gcatagaagt taagaatgaa gatcagattc aagggcttca tcaggcttgt     360
cagctggccc gccacgtcct cctcttggct gggaagagtt taaaggttga catgacaact    420
gaagagatag atgctcttgt tcatcgggaa atcatcagtc ataatgccta tccctcacct    480
ctaggctatg gaggttttcc aaaatctgtt tgtacctctg taaacaacgt gctctgtcat    540
ggtattcctg acagtcgacc tcttcaggat ggagatatta tcaacattga tgtcacagtc    600
tattacaatg gctaccatgg agacacctct gaaacatttt tggtgggcaa tgtggacgaa    660
tgtggtaaaa agttagtgga ggttgccagg aggtgtagag atgaagcaat gcagcttgc     720
agagcagggg ctcccttctc tgtaattgga acacaatca gccacataac tcatcagaat     780
ggttttcaag tctgtccaca ttttgtggga catggaatag gatcttactt tcatggacat    840
ccagaaattt ggcatcatgc aaacgacagt gatctaccca tggaggaggg catggcattc    900
actatagagc caatcatcac ggagggatcc cctgaattta aagtcctgga ggatgcatgg    960
actgtggtct ccctagacaa tcaaaggtcg gcgcagttcg agcacacggt tctgatcacg   1020
tcgaggggcg cgcagatcct gaccaaacta ccccatgagg cctgaggagc cgcccgaagg   1080
tcgcggtgac ctggtgcctt tttaaataaa ttgctgaaat ttggctggag aacttttaga   1140
agaaacaggg aaatgaccgg tggtgcggta acctgcgtgg ctcctgatag cgtttggaag   1200
aacgcgggg agactgaaga acaactggga actcggatct gaagccctgc tggggtcgcg    1260
cggctttgga aaacaaatc ctggccctgg actcggtttc ccaacgcggt caacgcatct    1320
ggagggact ggaggaaacc cccttgttgg aagagattcc aagagaagca cggtttctct    1380
ttccttgcct gactgttgga gtaaaaaacc tcttaaatcc attgtatcag aggtccttac   1440
ctctctgaca gttacatgat ctttgtatct gaactttgca cgtctgccga aaaatccgaa   1500
cctgttgact gggatttta agaatccgtt tctccctttt gtgtattcca tattggccgg    1560
ccccaaggat gctcgcagaa gccagccccc aaccccagcc cttccgtatc tttcccctcc   1620
atcgcggctt tgcgatgaaa gattagcccg cgaacagagg cattgattac aaacatgtcc   1680
ttggcagtgg actctgggcc tggccattct tcagtttct gtcaatccag aaacgcgact    1740
ttcctggacc cctgcggctc ttctncccg ccacattcag ccttcaaggc cagtccagan    1800
gtgaagtttg aggccctccc cccacccacc ccacacgcac gcacgcacgc tagagcgttt   1860
gctgcactag gaattcgagc ttgggcccca ctcgcccagt gtgaacagt ggctgattag    1920
tgggcggtct agtctctaaa atgaccctc cccagactgg cccttctcgc atcgggaccc    1980
gcgcttgcac gctgcaggag ccgcaaacgt cagctgttct ggaaaccgag agggtcccag   2040
agagaggaga tacgggcgca tttgagagca agggcctact tggccgggac tgaagcttgc   2100
gagttgagct ccagttcggc cggcagttcc atcccgcttc aggaacagga atccaagggc   2160
ccacgctctg tctgcaaggg ccattcctgc ccggagcacc ctccttccc ttgcgcttgc    2220
tctccggtac ctgttccgca cctgagctca aggcaggag aggccgggcc tctgcagtc     2280
cacgaaggaa gccgtctgcc ttcggttatg attttaggaa caagtccaac gagggtgttc   2340
```

-continued

```
aagcagttaa tggttgtgct aactcttgtt tctactgaag cgggttttgc aaagctgaca      2400
tcccttaaag ataacttggg ctttcggaag cggcaaggaa atggcacccg tagttgccag      2460
gacaggtggt gtcctcggcc aggactaaga gccagctcat ctttgtaaca ttcataatac      2520
gggaaactga ggaccaggtg gctcggaaaa gagatgagtt ccagcttta cctaacacag      2580 ggttctctcg tcgtccccca acccctccag ctcggcttct ttgtgtccag ggttgtagat      2640
ttttggatag aggtgtttct gattctagtg agtctgagaa ctggaaaaga ccaaggaggg      2700
gttgatgatt tmcaaggtcc atagaaaaac tttttgtgtg gtcggaagtt ggccaagcag      2760
aggcccacag cctgatgcta ctgccccca cccccccaaa gatctgaatt cctaaagatc      2820
aagagggttc agctggcctt gggagatgtt tgctggagaa tgacttcagt tttctcctaa      2880
ggcaatcaga ttgcanccat tagcattgta tnttatctgc aaatcagttt actccgaggt      2940
tccccaagga tagttttatt aggaccacag gnctttncta accnctgagg taacncgctg      3000
cttgtgcanc aattattttg aggtggaggt atttatgggn caagtttata attccattta      3060
ttaaagggac tancctaaaa aaaaaaaaaa aaaaaaaaa aaaagggcgg ccgc            3114
```

<210> SEQ ID NO 6
<211> LENGTH: 217
<212> TYPE: PRT
<213> ORGANISM: homo sapiens MetAP3 insert

<400> SEQUENCE: 6

```
Met Thr Thr Glu Glu Ile Asp Ala Leu Val His Arg Glu Ile Ile Ser
  1               5                  10                  15

His Asn Ala Tyr Pro Ser Pro Leu Gly Tyr Gly Gly Phe Pro Lys Ser
             20                  25                  30

Val Cys Thr Ser Val Asn Asn Val Leu Cys His Gly Ile Pro Asp Ser
         35                  40                  45

Arg Pro Leu Gln Asp Gly Asp Ile Ile Asn Ile Asp Val Thr Val Tyr
     50                  55                  60

Tyr Asn Gly Tyr His Gly Asp Thr Ser Glu Thr Phe Leu Val Gly Asn
 65                  70                  75                  80

Glu Asp Glu Cys Gly Lys Lys Leu Val Glu Val Ala Arg Arg Cys Arg
                 85                  90                  95

Asp Glu Ala Ile Ala Ala Cys Arg Ala Gly Ala Pro Phe Ser Val Ile
            100                 105                 110

Gly Asn Thr Ile Ser His Ile Thr His Gln Asn Gly Phe Gln Val Cys
        115                 120                 125

Pro His Phe Val Gly His Gly Ile Gly Ser Tyr Phe His Gly His Pro
    130                 135                 140

Glu Ile Trp His His Ala Asn Asp Ser Asp Leu Pro Met Glu Glu Gly
145                 150                 155                 160

Met Ala Phe Thr Ile Glu Pro Ile Ile Thr Glu Gly Ser Pro Glu Phe
                165                 170                 175

Lys Val Leu Glu Asp Ala Trp Thr Val Val Ser Leu Asp Asn Gln Arg
            180                 185                 190

Ser Ala Gln Phe Glu His Thr Val Leu Ile Thr Ser Arg Gly Ala Gln
        195                 200                 205

Ile Leu Thr Lys Leu Pro His Glu Ala
    210                 215
```

<210> SEQ ID NO 7
<211> LENGTH: 1529

```
<212> TYPE: DNA
<213> ORGANISM: homo sapiens MetAP3HZ2 - full length
<220> FEATURE:
<221> NAME/KEY: misc_feature
<222> LOCATION: 1326
<223> OTHER INFORMATION: n = A,T,C or G

<400> SEQUENCE: 7
gcggcgccag tggcgtccac ctgctcgtcc gcagaggttc tcatagaatt ttctcttcac      60
cactcaatca tatctactta cacaagcagt caagcagtca acaaagaaga aatttctttt     120
ttcggagaca aagagatatt tcacacagta tagttttgcc ggctgcagtt tcttcagctc     180
atccggttcc taagcacata agaagccag actatgtgac gacaggcatt gtaccagact      240
ggggagacag catagaagtt aagaatgaag atcagattca agggcttcat caggcttgtc     300
agctggcccg ccacgtcctc ctcttggctg ggaagagttt aaaggttgac atgacaactg     360
aagagataga tgctcttgtt catcgggaaa tcatcagtca taatgcctat ccctcacctc     420
taggctatgg aggttttcca aaatctgttt gtacctctgt aaacaacgtg ctctgtcatg     480
gtattcctga cagtcgacct cttcaggatg gagatattat caacattgat gtcacagtct     540
attacaatgg ctaccatgga gacacctctg aaacattttt ggtgggcaat gtggacgaat     600
gtggtaaaaa gttagtggag gttgccagga ggtgtagaga tgaagcaatt gcagcttgca     660 gagcagggc tcccttctct gtaattggaa acacaatcag ccacataact catcagaatg      720
gttttcaagt ctgtccacat tttgtgggac atggaatagg atcttacttt catggacatc     780
cagaaatttg gcatcatgca aacgacagtg atctacccat ggaggagggc atggcattca     840
ctatagagcc aatcatcacg gagggatccc ctgaatttaa agtcctggag gatgcatgga     900
ctgtggtctc cctagacaat caaaggtcgg cgcagttcga gcacacggtt ctgatcacgt     960 cgagggggcgc gcagatcctg accaaactac cccatgaggc ctgaggagcc gcccgaaggt    1020
cgcggtgacc tggtgccttt ttaaataaat tgctgaaatt tggctggaga acttttagaa    1080
gaaacaggga aatgaccggt ggtgcggtaa cctgcgtggc tcctgatagc gtttggaaga    1140
acgcggggga gactgaagag caactgggaa ctcggatctg aagccctgct ggggtcgcgc    1200
ggctttggaa aaacaaatcc tggccctgga ctcggttttcc cagcgcggtc aacgcatgtg    1260
gaggggactg gaggaaaccc ccttgttgga agagattcca agagaagcac ggktttctct    1320
ttcccntgcc ctgactgttg gagtaaaaaa cctcttaaat ccattgtatc aagaggtcct    1380
tacctctctg acagttacaa tgatctttgt atctgaactt tgcacgtctg ccgaaaaatc    1440
cgaacctgtt gactgggaaa aaaaaaaaa aacmmaaaaa aaaaaaaaaa aaaaaaaaa      1500 aaaaaaaaaa aaaaaaaarg ggcggccgc                                      1529

<210> SEQ ID NO 8
<211> LENGTH: 335
<212> TYPE: PRT
<213> ORGANISM: homo sapiens MetAP3HZ2 - full length

<400> SEQUENCE: 8

Met Ala Ala Pro Ser Gly Val His Leu Leu Val Arg Arg Gly Ser His
 1               5                  10                  15

Arg Ile Phe Ser Ser Pro Leu Asn His Ile Tyr Leu His Lys Gln Ser
                20                  25                  30

Ser Ser Gln Gln Arg Arg Asn Phe Phe Arg Arg Gln Arg Asp Ile
            35                  40                  45

Ser His Ser Ile Val Leu Pro Ala Ala Val Ser Ser Ala His Pro Val
```

```
            50                  55                  60
Pro Lys His Ile Lys Lys Pro Asp Tyr Val Thr Gly Ile Val Pro
65                  70                  75                  80

Asp Trp Gly Asp Ser Ile Glu Val Lys Asn Glu Asp Gln Ile Gln Gly
                85                  90                  95

Leu His Gln Ala Cys Gln Leu Ala Arg His Val Leu Leu Ala Gly
            100                 105                 110

Lys Ser Leu Lys Val Asp Met Thr Thr Glu Glu Ile Asp Ala Leu Val
        115                 120                 125

His Arg Glu Ile Ile Ser His Asn Ala Tyr Pro Ser Pro Leu Gly Tyr
    130                 135                 140

Gly Gly Phe Pro Lys Ser Val Cys Thr Ser Val Asn Asn Val Leu Cys
145                 150                 155                 160

His Gly Ile Pro Asp Ser Arg Pro Leu Gln Asp Gly Asp Ile Ile Asn
                165                 170                 175

Ile Asp Val Thr Val Tyr Tyr Asn Gly Tyr His Gly Asp Thr Ser Glu
            180                 185                 190

Thr Phe Leu Val Gly Asn Val Asp Glu Cys Gly Lys Lys Leu Val Glu
        195                 200                 205

Val Ala Arg Arg Cys Arg Asp Glu Ala Ile Ala Ala Cys Arg Ala Gly
    210                 215                 220

Ala Pro Phe Ser Val Ile Gly Asn Thr Ile Ser His Ile Thr His Gln
225                 230                 235                 240

Asn Gly Phe Gln Val Cys Pro His Phe Val Gly His Gly Ile Gly Ser
                245                 250                 255

Tyr Phe His Gly His Pro Glu Ile Trp His Ala Asn Asp Ser Asp
            260                 265                 270

Leu Pro Met Glu Glu Gly Met Ala Phe Thr Ile Glu Pro Ile Ile Thr
        275                 280                 285

Glu Gly Ser Pro Glu Phe Lys Val Leu Glu Asp Ala Trp Thr Val Val
    290                 295                 300

Ser Leu Asp Asn Gln Arg Ser Ala Gln Phe Glu His Thr Val Leu Ile
305                 310                 315                 320

Thr Ser Arg Gly Ala Gln Ile Leu Thr Lys Leu Pro His Glu Ala
                325                 330                 335
```

<210> SEQ ID NO 9
<211> LENGTH: 387
<212> TYPE: PRT
<213> ORGANISM: Saccharomyces cerevisiae MetAP1

<400> SEQUENCE: 9

```
Met Ser Thr Ala Thr Thr Thr Val Thr Thr Ser Asp Gln Ala Ser His
1               5                   10                  15

Pro Thr Lys Ile Tyr Cys Ser Gly Leu Gln Cys Gly Arg Glu Thr Ser
            20                  25                  30

Ser Gln Met Lys Cys Pro Val Cys Leu Lys Gln Gly Ile Val Ser Ile
        35                  40                  45

Phe Cys Asp Thr Ser Cys Tyr Glu Asn Asn Tyr Lys Ala His Lys Ala
    50                  55                  60

Leu His Asn Ala Lys Asp Gly Leu Glu Gly Ala Tyr Asp Pro Phe Pro
65                  70                  75                  80

Lys Phe Lys Tyr Ser Gly Lys Val Lys Ala Ser Tyr Pro Leu Thr Pro
                85                  90                  95
```

```
Arg Arg Tyr Val Pro Glu Asp Ile Pro Lys Pro Asp Trp Ala Ala Asn
            100                 105                 110

Gly Leu Pro Val Ser Glu Gln Arg Asn Asp Arg Leu Asn Asn Ile Pro
        115                 120                 125

Ile Tyr Lys Lys Asp Gln Ile Lys Lys Ile Arg Lys Ala Cys Met Leu
        130                 135                 140

Gly Arg Glu Val Leu Asp Ile Ala Ala His Val Arg Pro Gly Ile
145                 150                 155                 160

Thr Thr Asp Glu Leu Asp Glu Ile Val His Asn Glu Thr Ile Lys Arg
                165                 170                 175

Gly Ala Tyr Pro Ser Pro Leu Asn Tyr Tyr Asn Phe Pro Lys Ser Leu
                180                 185                 190

Cys Thr Ser Val Asn Glu Val Ile Cys His Gly Val Pro Asp Lys Thr
            195                 200                 205

Val Leu Lys Glu Gly Asp Ile Val Asn Leu Asp Val Ser Leu Tyr Tyr
        210                 215                 220

Gln Gly Tyr His Ala Asp Leu Asn Glu Thr Tyr Tyr Val Gly Glu Asn
225                 230                 235                 240

Ile Ser Lys Glu Ala Leu Asn Thr Thr Glu Thr Ser Arg Glu Cys Leu
                245                 250                 255

Lys Leu Ala Ile Lys Met Cys Lys Pro Gly Thr Thr Phe Gln Glu Leu
            260                 265                 270

Gly Asp His Ile Glu Lys His Ala Thr Glu Asn Lys Cys Ser Val Val
        275                 280                 285

Arg Thr Tyr Cys Gly His Gly Val Gly Glu Phe Phe His Cys Ser Pro
    290                 295                 300

Asn Ile Pro His Tyr Ala Lys Asn Arg Thr Pro Gly Val Met Lys Pro
305                 310                 315                 320

Gly Met Val Phe Thr Ile Glu Pro Met Ile Asn Glu Gly Thr Trp Lys
                325                 330                 335

Asp Met Thr Trp Pro Asp Asp Trp Thr Ser Thr Thr Gln Asp Gly Lys
            340                 345                 350

Leu Ser Ala Gln Phe Glu His Thr Leu Leu Val Thr Glu His Gly Val
        355                 360                 365

Glu Ile Leu Thr Ala Arg Asn Lys Lys Ser Pro Gly Gly Pro Arg Gln
    370                 375                 380

Arg Ile Lys
385

<210> SEQ ID NO 10
<211> LENGTH: 253
<212> TYPE: PRT
<213> ORGANISM: Synechocystis sp. MetAP1

<400> SEQUENCE: 10

Met Gly Asp Thr Ile Thr Leu Leu Ser Arg Arg Glu Ile Glu Lys Met
1               5                   10                  15

Arg Gln Ala Gly Gln Leu Ala Ala Leu Leu Asp His Leu Ala Pro
            20                  25                  30

Met Val Gln Pro Gly Ile Thr Thr Leu Glu Leu Asn Asp Glu Ala Glu
        35                  40                  45

Lys Trp Thr Lys Ala His Gly Ala Ile Ser Ala Pro Leu Gly Tyr Asn
    50                  55                  60

Gly Phe Pro Lys Ser Ile Cys Thr Ser Ile Asn Glu Val Ile Cys His
65                  70                  75                  80
```

```
Gly Ile Pro His Arg Lys Arg Val Leu Gln Ala Gly Asp Ile Ile Asn
                85                  90                  95

Val Asp Val Thr Pro Ile Val Asp Gly Tyr His Gly Asp Cys Ser Arg
            100                 105                 110

Thr Phe Phe Val Gly Thr Pro Ser Pro Val Ala Glu Lys Leu Val Lys
        115                 120                 125

Val Thr Glu Glu Cys Leu Arg Leu Gly Ile Glu Ala Val Lys Pro Gly
    130                 135                 140

Gly Lys Ile Gly Asp Ile Gly Ala Ala Ile Gln Ser His Ala Glu Ala
145                 150                 155                 160

Gln Gly Phe Ser Val Val Arg Asp Phe Val Gly His Gly Ile Ser Lys
                165                 170                 175

Ile Phe His Thr Ala Pro Gln Ile Pro His Tyr Gly Lys Ala Gly Lys
            180                 185                 190

Gly Lys Arg Leu Arg Pro Gly Met Val Phe Thr Ile Glu Pro Met Ile
        195                 200                 205

Asn Glu Gly Thr Trp Glu Ala Val Leu Leu Asp Asp Gly Trp Thr Ala
    210                 215                 220

Ile Thr Lys Asp Gly Lys Leu Ser Ala Gln Phe Glu His Thr Ile Ala
225                 230                 235                 240

Val Thr Glu Asp Gly Val Glu Ile Leu Thr Leu Gly Glu
                245                 250

<210> SEQ ID NO 11
<211> LENGTH: 274
<212> TYPE: PRT
<213> ORGANISM: Synechocystis sp. MetAP2

<400> SEQUENCE: 11

Met Asn His Gln Asn Leu Leu Ser Ile Thr Arg Asn Leu Val His Pro
 1               5                  10                  15

Pro Ile Ser Ser Gly Leu Val Leu Ser Ala Arg Glu Leu Asp Lys
             20                  25                  30

Met Arg Arg Val Gly Gln Leu Ala Ala Asn Leu Leu Asn His Leu Glu
         35                  40                  45

Ser Met Val Gln Pro Gly Val Ser Thr Gln Ala Leu Asn Asp Glu Ala
     50                  55                  60

Thr Arg Trp Met Glu Asp His Gly Ala Ile Ser Ala Thr Leu Gly Tyr
65                  70                  75                  80

Ala Pro Pro Gly Tyr Pro Pro Phe Thr Gly Ala Ile Cys Thr Ser Ile
                85                  90                  95

Asn Glu Val Val Cys His Gly Ile Pro Asn Pro Lys Gln Ile Leu Lys
            100                 105                 110

Asp Gly Asp Ile Ile Asn Ile Asp Val Thr Leu Arg Leu Ala Gly Tyr
        115                 120                 125

His Gly Asp Thr Ser Arg Thr Phe Leu Val Gly Ser Val Ser Ala Thr
    130                 135                 140

Ala Arg Lys Leu Val Glu Ala Thr Gln Glu Ser Met Met Arg Gly Ile
145                 150                 155                 160

Ala Glu Ile Lys Pro Gly Ala Arg Ile Gly Asp Ile Gly Ala Ala Ile
                165                 170                 175

Gln Ala Tyr Ala Glu Ala Ser Gly Phe Ser Val Val Arg Asp Met Val
            180                 185                 190

Gly His Gly Ile Gly Arg Gln Met His Thr Glu Leu Gln Ile Pro His
```

-continued

```
            195                 200                 205

Tyr Gly Lys Arg Gly Ser Gly Leu Lys Leu Arg Pro Gly Met Val Phe
    210                 215                 220

Thr Val Glu Pro Met Leu Asn Glu Gly Thr Tyr Glu Leu Thr Phe Leu
225                 230                 235                 240

Ala Asp Gly Trp Thr Val Ile Thr Lys Asp Lys Lys Leu Ser Ala Gln
                245                 250                 255

Phe Glu His Thr Val Val Thr Glu Gly Val Glu Ile Leu Thr
                260                 265                 270

Leu Ala

<210> SEQ ID NO 12
<211> LENGTH: 264
<212> TYPE: PRT
<213> ORGANISM: E. colli MetAP

<400> SEQUENCE: 12

Met Ala Ile Ser Ile Lys Thr Pro Glu Asp Ile Glu Lys Met Arg Val
  1               5                  10                  15

Ala Gly Arg Leu Ala Ala Glu Val Leu Glu Met Ile Glu Pro Tyr Val
                20                  25                  30

Lys Pro Gly Val Ser Thr Gly Glu Leu Asp Arg Ile Cys Asn Asp Tyr
                35                  40                  45

Ile Val Asn Glu Gln His Ala Val Ser Ala Cys Leu Gly Tyr His Gly
            50                  55                  60

Tyr Pro Lys Ser Val Cys Ile Ser Ile Asn Glu Val Val Cys His Gly
65                  70                  75                  80

Ile Pro Asp Asp Ala Lys Leu Leu Lys Asp Gly Asp Ile Val Asn Ile
                85                  90                  95

Asp Val Thr Val Ile Lys Asp Gly Phe His Gly Asp Thr Ser Lys Met
                100                 105                 110

Phe Ile Val Gly Lys Pro Thr Ile Met Gly Glu Arg Leu Cys Arg Ile
            115                 120                 125

Thr Gln Glu Ser Leu Tyr Leu Ala Leu Arg Met Val Lys Pro Gly Ile
130                 135                 140

Asn Leu Arg Glu Ile Gly Ala Ala Ile Gln Lys Phe Val Glu Ala Glu
145                 150                 155                 160

Gly Phe Ser Val Val Arg Glu Tyr Cys Gly His Gly Ile Gly Arg Gly
                165                 170                 175

Phe His Glu Glu Pro Gln Val Leu His Tyr Asp Ser Arg Glu Thr Asn
            180                 185                 190

Val Val Leu Lys Pro Gly Met Thr Phe Thr Ile Glu Pro Met Val Asn
            195                 200                 205

Ala Gly Lys Lys Glu Ile Arg Thr Met Lys Asp Gly Trp Thr Val Lys
    210                 215                 220

Thr Lys Asp Arg Ser Leu Ser Ala Gln Tyr Glu His Thr Ile Val Val
225                 230                 235                 240

Thr Asp Asn Gly Cys Glu Ile Leu Thr Leu Arg Lys Asp Asp Thr Ile
                245                 250                 255

Pro Ala Ile Ile Ser His Asp Glu
            260

<210> SEQ ID NO 13
<211> LENGTH: 268
<212> TYPE: PRT
```

<213> ORGANISM: Haemophilus influenzae MetAP

<400> SEQUENCE: 13

Met Ala Ile Pro Ile Arg Thr Glu Lys Glu Ile Val Lys Leu Arg Glu
1               5                   10                  15

Ala Cys Lys Leu Ala Ser Asp Val Leu Val Met Ile Glu Pro Tyr Val
            20                  25                  30

Lys Ala Gly Val Thr Thr Gly Glu Leu Asp Arg Ile Cys His Glu Tyr
        35                  40                  45

Met Val Asn Glu Gln Lys Val Ile Pro Ala Cys Leu Asn Tyr His Gly
    50                  55                  60

Phe Pro Lys Ala Thr Cys Ile Ser Ile Asn Glu Val Val Cys His Gly
65                  70                  75                  80

Ile Pro Ser Asp Asp Lys Val Leu Lys Asn Gly Asp Ile Val Asn Ile
                85                  90                  95

Asp Val Thr Val Ile Lys Asp Gly Tyr Phe Gly Asp Asn Ser Lys Met
            100                 105                 110

Tyr Ile Val Gly Gly Glu Thr Asn Ile Arg Ser Lys Lys Leu Val Glu
        115                 120                 125

Ala Ala Gln Glu Ala Leu Tyr Val Gly Ile Arg Thr Val Lys Pro Asp
    130                 135                 140

Ile Arg Leu Asn Glu Ile Gly Lys Ala Val Gln Lys Tyr Thr Glu Ser
145                 150                 155                 160

Gln Thr Phe Ser Val Val Arg Glu Tyr Cys Gly His Gly Val Gly Thr
                165                 170                 175

Glu Phe His Cys Glu Pro Gln Val Leu His Tyr Tyr Ala Asp Asp Gly
            180                 185                 190

Gly Val Ile Leu Lys Pro Gly Met Val Phe Thr Ile Glu Pro Met Ile
        195                 200                 205

Asn Ala Gly Lys Lys Glu Val Arg Val Met Gly Asp Gly Trp Thr Val
    210                 215                 220

Lys Thr Lys Asp Arg Ser His Ser Ala Gln Tyr Glu His Gln Leu Ile
225                 230                 235                 240

Val Thr Glu Thr Gly Cys Glu Val Met Thr Ile Arg Asp Glu Glu Ile
                245                 250                 255

Ala Glu Gly Arg Ile Ser Arg Ile Met Val Asn Val
            260                 265

<210> SEQ ID NO 14
<211> LENGTH: 305
<212> TYPE: PRT
<213> ORGANISM: Synechocystis sp. MetAP3

<400> SEQUENCE: 14

Met Pro Arg Ile Phe Pro Trp Lys Leu Trp Arg Lys Ser Arg Pro Ala
1               5                   10                  15

Trp Pro Arg Phe Leu Gly Thr His Pro Met Asn Leu Leu Ser Gln Leu
            20                  25                  30

Phe Ala Pro Pro Ser Pro Val Pro Ser Pro Thr Pro Lys Ala Lys Lys
        35                  40                  45

Arg Ser Arg Arg Gly Val Gln Ile Lys Thr Pro Ala Glu Ile Ala Ile
    50                  55                  60

Met Arg Gln Ala Gly Ala Ile Ala Ala Gln Val Leu Lys Glu Ile Ala
65                  70                  75                  80

Ala Thr Val Gln Pro Gly Met Thr Thr Gly Asp Leu Asp Gln Leu Ala

```
                    85                  90                   95
Glu Glu Arg Ile Arg Ser Leu Gly Ala Thr Pro Ser Phe Lys Gly Tyr
                100                 105                 110

His Gly Phe Pro Ala Ser Ile Cys Ala Cys Val Asn Asn Glu Val Val
            115                 120                 125

His Gly Ile Pro Arg Arg Arg Lys Lys Ile Arg Ser Gly Asp Leu Leu
        130                 135                 140

Lys Val Asp Thr Gly Ala Tyr Phe Gln Gly Tyr His Gly Asp Ser Cys
145                 150                 155                 160

Ile Thr Ile Ala Val Gly Lys Val Ser Pro Gln Ala Gln Arg Leu Met
                165                 170                 175

Glu Val Ala Glu Gly Ala Leu Tyr Ala Gly Ile Glu Gln Val Lys Pro
            180                 185                 190

Gly Asn Tyr Leu Met Asp Ile Ala Gly Ala Ile Glu Asp Tyr Val Lys
        195                 200                 205

Pro Thr Gly Tyr Thr Ile Val Glu Glu Phe Thr Gly His Gly Val Gly
    210                 215                 220

Gln Ala Leu His Glu Asp Pro His Val Phe Asn Val Arg Cys Arg Asp
225                 230                 235                 240

Leu Pro Asn Val Lys Leu Lys Pro Gly Met Thr Leu Ala Ile Glu Pro
                245                 250                 255

Ile Val Asn Ala Gly Ser Arg Phe Thr Arg Thr Leu Gly Asp Arg Trp
            260                 265                 270

Thr Val Val Thr Val Asp Asn Ala Leu Ser Ala Gln Phe Glu His Thr
        275                 280                 285

Val Leu Val Thr Ala Thr Gly Tyr Glu Leu Leu Thr Asp Arg Arg Leu
    290                 295                 300

Val
305

<210> SEQ ID NO 15
<211> LENGTH: 248
<212> TYPE: PRT
<213> ORGANISM: Bacillus subtilus MetAP

<400> SEQUENCE: 15

Met Ile Ile Cys Lys Thr Pro Arg Glu Leu Gly Ile Met Arg Glu Ala
1               5                  10                  15

Gly Arg Ile Val Ala Leu Thr His Glu Glu Leu Lys Lys His Ile Lys
            20                  25                  30

Pro Gly Ile Ser Thr Lys Glu Leu Asp Gln Ile Ala Glu Arg Phe Ile
        35                  40                  45

Lys Lys Gln Gly Ala Ile Pro Ser Phe Lys Gly Tyr Asn Gly Phe Arg
    50                  55                  60

Gly Ser Ile Cys Val Ser Val Asn Glu Glu Leu Val His Gly Ile Pro
65                  70                  75                  80

Gly Ser Arg Val Leu Lys Asp Gly Asp Ile Ile Ser Ile Asp Ile Gly
                85                  90                  95

Ala Lys Leu Asn Gly Tyr His Gly Asp Ser Ala Trp Thr Tyr Pro Val
            100                 105                 110

Gly Asn Ile Ser Asp Asp Lys Lys Leu Leu Glu Val Thr Glu Glu
        115                 120                 125

Ser Leu Tyr Lys Gly Leu Gln Glu Ala Lys Pro Gly Glu Arg Leu Ser
    130                 135                 140
```

```
Asn Ile Ser His Ala Ile Gln Thr Tyr Val Glu Asn Glu Gln Phe Ser
145                 150                 155                 160

Val Val Arg Glu Tyr Val Gly His Gly Val Gly Gln Asp Leu His Glu
                165                 170                 175

Asp Pro Gln Ile Pro His Tyr Gly Pro Pro Asn Lys Gly Pro Arg Leu
            180                 185                 190

Lys Pro Gly Met Val Leu Ala Ile Glu Pro Met Val Asn Ala Gly Ser
        195                 200                 205

Arg Tyr Val Lys Thr Leu Ala Asp Asn Trp Thr Val Thr Val Asp
    210                 215                 220

Gly Lys Lys Cys Ala His Phe Glu His Thr Ile Ala Ile Thr Glu Thr
225                 230                 235                 240

Gly Phe Asp Ile Leu Thr Arg Val
                245

<210> SEQ ID NO 16
<211> LENGTH: 478
<212> TYPE: PRT
<213> ORGANISM: Mus musculus MetAP2

<400> SEQUENCE: 16

Met Ala Gly Val Glu Gln Ala Ala Ser Phe Gly Gly His Leu Asn Gly
1               5                   10                  15

Asp Leu Asp Pro Asp Asp Arg Glu Glu Gly Thr Ser Ser Thr Ala Glu
                20                  25                  30

Glu Ala Ala Lys Lys Lys Arg Arg Lys Lys Lys Lys Gly Lys Gly Ala
            35                  40                  45

Val Ser Ala Val Gln Gln Glu Leu Asp Lys Glu Ser Gly Ala Leu Val
    50                  55                  60

Asp Glu Val Ala Lys Gln Leu Glu Ser Gln Ala Leu Glu Glu Lys Glu
65                  70                  75                  80

Arg Asp Asp Asp Asp Glu Asp Gly Asp Gly Asp Ala Asp Gly Ala Thr
                85                  90                  95

Gly Lys Lys Lys Lys Lys Lys Lys Lys Arg Gly Pro Lys Val Gln
            100                 105                 110

Thr Asp Pro Pro Ser Val Pro Ile Cys Asp Leu Tyr Pro Asn Gly Val
        115                 120                 125

Phe Pro Lys Gly Gln Glu Cys Glu Tyr Pro Pro Thr Gln Asp Gly Arg
130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
                165                 170                 175

Arg Gln Val Arg Lys Tyr Val Met Ser Trp Ile Lys Pro Gly Met Thr
            180                 185                 190

Met Ile Glu Ile Cys Glu Lys Leu Glu Asp Cys Ser Arg Lys Leu Ile
        195                 200                 205

Lys Glu Asn Gly Leu Asn Ala Gly Leu Ala Phe Pro Thr Gly Cys Ser
    210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
            260                 265                 270
```

-continued

```
Tyr Asp Ile Leu Leu Thr Ala Val Lys Asp Ala Thr Asn Thr Gly Ile
            275                 280                 285

Lys Cys Ala Gly Ile Asp Val Arg Leu Cys Asp Val Gly Glu Ala Ile
    290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Pro Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser
            355                 360                 365

Thr Gly Lys Gly Val Val His Asp Asp Met Glu Cys Ser His Tyr Met
370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
            405                 410                 415

Arg Arg Trp Leu Asp Arg Leu Gly Glu Ser Lys Tyr Leu Met Ala Leu
            420                 425                 430

Lys Asn Leu Cys Asp Leu Gly Ile Val Asp Pro Tyr Pro Pro Leu Cys
            435                 440                 445

Asp Ile Lys Gly Ser Tyr Thr Ala Gln Phe Glu His Thr Ile Leu Leu
            450                 455                 460

Arg Pro Thr Cys Lys Glu Val Val Ser Arg Gly Asp Asp Tyr
465                 470                 475

<210> SEQ ID NO 17
<211> LENGTH: 478
<212> TYPE: PRT
<213> ORGANISM: Rattus MetAP2

<400> SEQUENCE: 17

Met Ala Gly Val Glu Glu Ala Ser Ser Phe Gly Gly His Leu Asn Arg
  1               5                  10                  15

Asp Leu Asp Pro Asp Asp Arg Glu Glu Gly Thr Ser Ser Thr Ala Glu
             20                  25                  30

Glu Ala Ala Lys Lys Lys Arg Arg Lys Lys Lys Gly Lys Gly Ala
            35                  40                  45

Val Ser Ala Gly Gln Gln Glu Leu Asp Lys Glu Ser Gly Thr Ser Val
    50                  55                  60

Asp Glu Val Ala Lys Gln Leu Glu Arg Gln Ala Leu Glu Glu Lys Glu
65                  70                  75                  80

Lys Asp Asp Asp Glu Asp Gly Asp Gly Asp Gly Asp Gly Ala Ala
            85                  90                  95

Gly Lys Lys Lys Lys Lys Lys Lys Arg Gly Pro Arg Val Gln
            100                 105                 110

Thr Asp Pro Pro Ser Val Pro Ile Cys Asp Leu Tyr Pro Asn Gly Val
            115                 120                 125

Phe Pro Lys Gly Gln Glu Cys Glu Tyr Pro Pro Thr Gln Asp Gly Arg
            130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
```

```
                    165                 170                 175
Arg Gln Val Arg Lys Tyr Val Met Ser Trp Ile Lys Pro Gly Met Thr
                180                 185                 190

Met Ile Glu Ile Cys Glu Lys Leu Glu Asp Cys Ser Arg Lys Leu Ile
            195                 200                 205

Lys Glu Asn Gly Leu Asn Ala Gly Leu Ala Phe Pro Thr Gly Cys Ser
        210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                245                 250                 255

Ser Gly Arg Ile Ile Asp Cys Ala Phe Thr Val Thr Phe Asn Pro Lys
            260                 265                 270

Tyr Asp Ile Leu Leu Lys Ala Val Lys Asp Ala Thr Asn Thr Gly Ile
        275                 280                 285

Lys Cys Ala Gly Ile Asp Val Arg Leu Cys Asp Val Gly Glu Ala Ile
        290                 295                 300

Gln Glu Val Met Glu Ser Tyr Glu Val Glu Ile Asp Gly Lys Thr Tyr
305                 310                 315                 320

Gln Val Lys Pro Ile Arg Asn Leu Asn Gly His Ser Ile Gly Pro Tyr
                325                 330                 335

Arg Ile His Ala Gly Lys Thr Val Pro Ile Val Lys Gly Gly Glu Ala
            340                 345                 350

Thr Arg Met Glu Glu Gly Glu Val Tyr Ala Ile Glu Thr Phe Gly Ser
        355                 360                 365

Thr Gly Lys Gly Val Val His Asp Asp Met Glu Cys Ser His Tyr Met
        370                 375                 380

Lys Asn Phe Asp Val Gly His Val Pro Ile Arg Leu Pro Arg Thr Lys
385                 390                 395                 400

His Leu Leu Asn Val Ile Asn Glu Asn Phe Gly Thr Leu Ala Phe Cys
                405                 410                 415

Arg Arg Trp Leu Asp Arg Leu Gly Glu Ser Lys Tyr Leu Met Ala Leu
            420                 425                 430

Lys Asn Leu Cys Asp Leu Gly Ile Val Asp Pro Tyr Pro Pro Leu Cys
        435                 440                 445

Asp Ile Lys Gly Ser Tyr Thr Ala Gln Phe Glu His Thr Ile Leu Leu
        450                 455                 460

Arg Pro Thr Cys Lys Glu Val Val Ser Arg Gly Asp Asp Tyr
465                 470                 475

<210> SEQ ID NO 18
<211> LENGTH: 421
<212> TYPE: PRT
<213> ORGANISM: Saccharomyces cerevisiae MetAP2

<400> SEQUENCE: 18

Met Thr Asp Ala Glu Ile Glu Asn Ser Pro Ala Ser Asp Leu Lys Glu
  1               5                  10                  15

Leu Asn Leu Glu Asn Glu Gly Val Glu Gln Gln Asp Gln Ala Lys Ala
                20                  25                  30

Asp Glu Ser Asp Pro Val Glu Ser Lys Lys Lys Asn Lys Lys Lys
            35                  40                  45

Lys Lys Lys Lys Ser Asn Val Lys Lys Ile Glu Leu Leu Phe Pro Asp
        50                  55                  60
```

```
Gly Lys Tyr Pro Glu Gly Ala Trp Met Asp Tyr His Gln Asp Phe Asn
 65                  70                  75                  80

Leu Gln Arg Thr Thr Asp Glu Glu Ser Arg Tyr Leu Lys Arg Asp Leu
                 85                  90                  95

Glu Arg Ala Glu His Trp Asn Asp Val Arg Lys Gly Ala Glu Ile His
            100                 105                 110

Arg Arg Val Arg Arg Ala Ile Lys Asp Arg Ile Val Pro Gly Met Lys
        115                 120                 125

Leu Met Asp Ile Ala Asp Met Ile Glu Asn Thr Thr Arg Lys Tyr Thr
130                 135                 140

Gly Ala Glu Asn Leu Leu Ala Met Glu Asp Pro Lys Ser Gln Gly Ile
145                 150                 155                 160

Gly Phe Pro Thr Gly Leu Ser Leu Asn His Cys Ala Ala His Phe Thr
                165                 170                 175

Pro Asn Ala Gly Asp Lys Thr Val Leu Lys Tyr Glu Asp Val Met Lys
            180                 185                 190

Val Asp Tyr Gly Val Gln Val Asn Gly Asn Ile Ile Asp Ser Ala Phe
        195                 200                 205

Thr Val Ser Phe Asp Pro Gln Tyr Asp Asn Leu Leu Ala Ala Val Lys
    210                 215                 220

Asp Ala Thr Tyr Thr Gly Ile Lys Glu Ala Gly Ile Asp Val Arg Leu
225                 230                 235                 240

Thr Asp Ile Gly Glu Ala Ile Gln Glu Val Met Glu Ser Tyr Glu Val
                245                 250                 255

Glu Ile Asn Gly Glu Thr Tyr Gln Val Lys Pro Cys Arg Asn Leu Cys
            260                 265                 270

Gly His Ser Ile Ala Pro Tyr Arg Ile His Gly Gly Lys Ser Val Pro
        275                 280                 285

Ile Val Lys Asn Gly Asp Thr Thr Lys Met Glu Glu Gly Glu His Phe
    290                 295                 300

Ala Ile Glu Thr Phe Gly Ser Thr Gly Arg Gly Tyr Val Thr Ala Gly
305                 310                 315                 320

Gly Glu Val Ser His Tyr Ala Arg Ser Ala Glu Asp His Gln Val Met
                325                 330                 335

Pro Thr Leu Asp Ser Ala Lys Asn Leu Leu Lys Thr Ile Asp Arg Asn
            340                 345                 350

Phe Gly Thr Leu Pro Phe Cys Arg Arg Tyr Leu Asp Arg Leu Gly Gln
        355                 360                 365

Glu Lys Tyr Leu Phe Ala Leu Asn Asn Leu Val Arg His Gly Leu Val
    370                 375                 380

Gln Asp Tyr Pro Pro Leu Asn Asp Ile Pro Gly Ser Tyr Thr Ala Gln
385                 390                 395                 400

Phe Glu His Thr Ile Leu Leu His Ala His Lys Lys Glu Val Val Ser
                405                 410                 415

Lys Gly Asp Asp Tyr
            420

<210> SEQ ID NO 19
<211> LENGTH: 188
<212> TYPE: PRT
<213> ORGANISM: Methanothermus fervidus MetAP

<400> SEQUENCE: 19

Met Glu Lys Phe Lys Lys Ala Gly Lys Ile Ala Ser Lys Val Arg Lys
 1               5                  10                  15
```

```
Lys Ala Ile Lys Ala Val Lys Gly Glu Met Lys Ile Leu Asp Leu Ala
            20                  25                  30

Glu Phe Ile Glu Asn Glu Ile Glu Lys Met Gly Ala Lys Pro Ala Phe
            35                  40                  45

Pro Cys Asn Ile Ser Val Asn Glu Ile Thr Ala His Tyr Ser Pro Pro
        50                  55                  60

Cys Asn Asp Asp Arg Lys Ile Leu Pro Gly Asp Leu Val Lys Ile Asp
65                  70                  75                  80

Ile Gly Val His Val Asp Gly Phe Ile Gly Asp Thr Ala Thr Thr Val
                85                  90                  95

Leu Val Glu Gly Tyr Glu Asp Leu Lys Asn Tyr Asn Asp Glu Leu Ala
            100                 105                 110

Glu Lys Asn Lys Lys Met Ile Glu Ala Ala Glu Ser Ala Leu Glu Asn
            115                 120                 125

Ala Ile Asn Thr Ile Arg Asp Gly Val Glu Ile Gly Lys Ile Gly Glu
        130                 135                 140

Val Ile Glu Asn Thr Ile Asn Lys Phe Gly Phe Lys Pro Ile Ser Asn
145                 150                 155                 160

Leu Thr Gly His Thr Ile Asp Arg Trp Val Leu His Ser Gly Leu Ser
                165                 170                 175

Ile Pro Asn Val Lys Gly Gln Asn Ser His Lys Leu
            180                 185
```

```
<210> SEQ ID NO 20
<211> LENGTH: 294
<212> TYPE: PRT
<213> ORGANISM: Methanothermus jannaschii MetAP
<220> FEATURE:
<221> NAME/KEY: UNSURE
<222> LOCATION: (28)...(28)
<223> OTHER INFORMATION: at all Xaa positions
<220> FEATURE:
<221> NAME/KEY: VARIANT
<222> LOCATION: 28
<223> OTHER INFORMATION: Xaa = Any Amino Acid

<400> SEQUENCE: 20

Met Glu Ile Glu Gly Tyr Glu Lys Ile Ile Glu Ala Gly Lys Ile Ala
1               5                   10                  15

Ser Lys Val Arg Glu Glu Ala Val Lys Leu Ile Xaa Pro Gly Val Lys
            20                  25                  30

Leu Leu Glu Val Ala Glu Phe Val Glu Asn Arg Ile Arg Glu Leu Gly
            35                  40                  45

Gly Glu Pro Ala Phe Pro Cys Asn Ile Ser Ile Asn Glu Ile Ala Ala
        50                  55                  60

His Tyr Thr Pro Lys Leu Asn Asp Asn Leu Glu Phe Lys Asp Asp
65                  70                  75                  80

Val Val Lys Leu Asp Leu Gly Ala His Val Asp Gly Tyr Ile Ala Asp
                85                  90                  95

Thr Ala Ile Thr Val Asp Leu Ser Asn Ser Tyr Lys Asp Leu Val Lys
            100                 105                 110

Ala Ser Glu Asp Ala Leu Tyr Thr Val Ile Lys Glu Ile Asn Pro Pro
            115                 120                 125

Met Asn Ile Gly Glu Met Gly Lys Ile Ile Gln Glu Val Ile Glu Ser
        130                 135                 140

Tyr Gly Tyr Lys Pro Ile Ser Asn Leu Ser Gly His Val Met His Arg
145                 150                 155                 160
```

```
Tyr Glu Leu His Thr Gly Ile Ser Ile Pro Asn Val Tyr Glu Arg Thr
            165                 170                 175

Asn Gln Tyr Ile Asp Val Gly Asp Leu Val Ala Ile Glu Pro Phe Ala
        180                 185                 190

Thr Asp Gly Phe Gly Met Val Lys Asp Gly Asn Leu Gly Asn Ile Tyr
        195                 200                 205

Lys Phe Leu Ala Lys Arg Pro Ile Arg Leu Pro Gln Ala Arg Lys Leu
        210                 215                 220

Leu Asp Val Ile Ser Lys Asn Tyr Pro Tyr Leu Pro Phe Ala Glu Arg
225                 230                 235                 240

Trp Val Leu Lys Asn Glu Ser Glu Arg Leu Ala Leu Asn Ser Leu Ile
            245                 250                 255

Arg Ala Ser Cys Ile Tyr Gly Tyr Pro Ile Leu Lys Glu Arg Glu Asn
                260                 265                 270

Gly Ile Val Gly Gln Ala Glu His Thr Ile Leu Ile Thr Glu Asn Gly
            275                 280                 285

Val Glu Ile Thr Thr Lys
        290

<210> SEQ ID NO 21
<211> LENGTH: 301
<212> TYPE: PRT
<213> ORGANISM: Sulfolobus solfataricus MetAP

<400> SEQUENCE: 21

Met Thr Glu Asp Glu Leu Asn Lys Leu Leu Leu Ala Gly Lys Ile Ala
1               5                   10                  15

Ala Lys Ala Arg Asp Glu Val Ser Leu Asp Val Lys Ala Ser Ala Lys
            20                  25                  30

Val Leu Asp Ile Cys Glu Glu Val Glu Ser Ile Ile Glu Asn Lys
            35                  40                  45

Ala Phe Pro Ser Phe Pro Cys Asn Ile Ser Ile Asn Ser Glu Ala Ala
        50                  55                  60

His Tyr Ser Pro Thr Ile Asn Asp Glu Lys Arg Ile Pro Glu Gly Ala
65              70                  75                  80

Val Val Lys Leu Asp Leu Gly Ala His Ile Asp Gly Phe Ile Ser Asp
            85                  90                  95

Thr Ala Ile Thr Ile Ser Leu Asp Ser Arg Tyr Gln Arg Leu Leu Asp
                100                 105                 110

Ala Ser Lys Thr Ala Leu Glu Ala Ala Ile Thr Asn Phe Lys Ala Gly
        115                 120                 125

Leu Ser Ile Gly Glu Ile Gly Arg Val Ile Glu Lys Val Ile Arg Ala
130                 135                 140

Gln Gly Tyr Lys Pro Ile Arg Asn Leu Gly Gly His Leu Ile Arg Arg
145                 150                 155                 160

Tyr Glu Leu His Ala Gly Val Phe Ile Pro Asn Val Tyr Glu Arg Gly
            165                 170                 175

Leu Gly Val Ile Gln Ser Asp Ser Val Tyr Ala Ile Glu Pro Phe Ala
        180                 185                 190

Thr Asp Gly Gly Gly Glu Val Val Glu Gly Lys Ser Ile Thr Ile Tyr
        195                 200                 205

Ser Leu Lys Asn Pro Asn Ile Lys Gly Leu Ser Ser Arg Glu Asn Glu
        210                 215                 220

Leu Ile Asp Phe Ile Tyr Thr Arg Phe Asn Tyr Leu Pro Phe Ser Glu
```

```
                225                 230                 235                 240
Arg Trp Leu Lys Glu Phe Ser Thr Asn Val Asp Glu Leu Arg Asn Asn
                    245                 250                 255
Ile Lys Asn Leu Val Lys Gly Ala Leu Arg Gly Tyr Pro Ile Leu
                260                 265                 270
Ile Glu Ile Lys Lys Gly Val Val Ser Gln Phe Glu His Thr Val Ile
                275                 280                 285
Val Lys Gly Asp Ser Ile Ile Val Ser Thr Lys Ser Leu
                290                 295                 300

<210> SEQ ID NO 22
<211> LENGTH: 250
<212> TYPE: PRT
<213> ORGANISM: Helicobacter pylori MetAP

<400> SEQUENCE: 22

Met Ala Ile Ser Ile Lys Ser Pro Lys Glu Ile Lys Ala Leu Arg Lys
  1               5                  10                  15
Ala Gly Glu Leu Thr Ala Gln Ala Leu Ala Leu Leu Glu Arg Glu Val
                 20                  25                  30
Arg Pro Gly Val Ser Leu Leu Glu Leu Asp Lys Met Ala Glu Asp Phe
             35                  40                  45
Ile Lys Ser Ser His Ala Arg Pro Ala Phe Lys Gly Leu Tyr Gly Phe
         50                  55                  60
Pro Asn Ser Val Cys Met Ser Leu Asn Glu Val Val Ile His Gly Ile
 65                  70                  75                  80
Pro Thr Asp Tyr Val Leu Gln Glu Gly Asp Ile Ile Gly Leu Asp Leu
                 85                  90                  95
Gly Val Glu Val Asp Gly Tyr Tyr Gly Asp Ser Ala Leu Thr Leu Pro
            100                 105                 110
Ile Gly Ala Ile Ser Pro Gln Asp Glu Lys Leu Leu Ala Cys Ser Lys
        115                 120                 125
Glu Ser Leu Met His Ala Ile Asn Ser Ile Arg Val Gly Met His Phe
    130                 135                 140
Lys Glu Leu Ser Gln Ile Leu Glu Ser Thr Ile Thr Glu Arg Gly Phe
145                 150                 155                 160
Val Pro Leu Lys Gly Phe Cys Gly His Gly Ile Gly Lys Lys Pro His
                165                 170                 175
Glu Glu Pro Glu Ile Pro Asn Tyr Leu Glu Lys Gly Val Lys Pro Asn
            180                 185                 190
Ser Gly Pro Lys Ile Lys Glu Gly Met Val Phe Cys Leu Glu Pro Met
        195                 200                 205
Val Cys Gln Lys Gln Gly Glu Pro Lys Ile Leu Ala Asp Lys Trp Ser
    210                 215                 220
Val Val Ser Val Asp Gly Leu Asn Thr Ser His His Glu His Thr Ile
225                 230                 235                 240
Ala Ile Val Gly Asn Lys Ala Val Ile Leu
                245                 250

<210> SEQ ID NO 23
<211> LENGTH: 20
<212> TYPE: DNA
<213> ORGANISM: Homo sapiens MetAP3-For primer

<400> SEQUENCE: 23
tggacgaatg tggtaaaaag                                              20
```

-continued

<210> SEQ ID NO 24
<211> LENGTH: 30
<212> TYPE: DNA
<213> ORGANISM: homo sapiens MAP3 FOR+ADAPT+ATG primer

<400> SEQUENCE: 24
ctagaattca tggcggcgcc cagtggcgtc                              30

<210> SEQ ID NO 25
<211> LENGTH: 27
<212> TYPE: DNA
<213> ORGANISM: homo sapiens MAP3 REV-NotI primer

<400> SEQUENCE: 25
tgcggccgct caggcctcat ggggtag                                 27

<210> SEQ ID NO 26
<211> LENGTH: 17
<212> TYPE: DNA
<213> ORGANISM: homo sapiens MAP3 FOR2 primer

<400> SEQUENCE: 26
acaatcagcc acataac                                            17

<210> SEQ ID NO 27
<211> LENGTH: 19
<212> TYPE: DNA
<213> ORGANISM: homo sapiens MAP3 FOR3 primer

<400> SEQUENCE: 27
ttctcttcac cactcaatc                                          19

<210> SEQ ID NO 28
<211> LENGTH: 17
<212> TYPE: DNA
<213> ORGANISM: homo sapiens MAP3 FOR4 primer

<400> SEQUENCE: 28
gtttctcttt cccttgc                                            17

<210> SEQ ID NO 29
<211> LENGTH: 21
<212> TYPE: DNA
<213> ORGANISM: homo sapiens MAP3 FOR5 primer

<400> SEQUENCE: 29
gccacattca gccttcaagg c                                       21

<210> SEQ ID NO 30
<211> LENGTH: 20
<212> TYPE: DNA
<213> ORGANISM: homo sapiens MAP3 REV1 primer

<400> SEQUENCE: 30
atccctccgt gatgattggc                                         20

<210> SEQ ID NO 31
<211> LENGTH: 17
<212> TYPE: DNA
<213> ORGANISM: homo sapiens MAP3 REV2 primer

<400> SEQUENCE: 31
gcaagggaaa gagaaac                                                            17

<210> SEQ ID NO 32
<211> LENGTH: 22
<212> TYPE: DNA
<213> ORGANISM: homo sapiens MAP3 REV1.2 primer

<400> SEQUENCE: 32
agcccctgct ctgcaagctg ca                                                      22

<210> SEQ ID NO 33
<211> LENGTH: 21
<212> TYPE: DNA
<213> ORGANISM: homo sapiens MAP3 REV3 primer

<400> SEQUENCE: 33
tccatagcct agaggtgagg g                                                       21

<210> SEQ ID NO 34
<211> LENGTH: 17
<212> TYPE: DNA
<213> ORGANISM: homo sapiens MAP3 REV4 primer

<400> SEQUENCE: 34
aaggccagct gaaccct                                                            17

<210> SEQ ID NO 35
<211> LENGTH: 21
<212> TYPE: DNA
<213> ORGANISM: homo sapiens hmap1F1 primer

<400> SEQUENCE: 35
aagcggtctg ctcagtttga g                                                       21

<210> SEQ ID NO 36
<211> LENGTH: 18
<212> TYPE: DNA
<213> ORGANISM: homo sapiens hmap1R1 primer

<400> SEQUENCE: 36
ggccgtgcac tgtcaagt                                                           18

<210> SEQ ID NO 37
<211> LENGTH: 26
<212> TYPE: DNA
<213> ORGANISM: hmap1P1

<400> SEQUENCE: 37
acaccctcct ggtcacagac actggc                                                  26

<210> SEQ ID NO 38
<211> LENGTH: 23
<212> TYPE: DNA
<213> ORGANISM: homo sapiens hmap2F1 primer

<400> SEQUENCE: 38
gaccctccct cagttccaat atg                                                     23

<210> SEQ ID NO 39
<211> LENGTH: 20
<212> TYPE: DNA
<213> ORGANISM: homo sapiens hmap2R1 primer

<400> SEQUENCE: 39

```
gtgggtgggt attcgcattc                                              20

<210> SEQ ID NO 40
<211> LENGTH: 34
<212> TYPE: DNA
<213> ORGANISM: homo sapiens hmap2P2 primer

<400> SEQUENCE: 40
acctgtatcc taatggtgta tttcccaaag gaca                              34

<210> SEQ ID NO 41
<211> LENGTH: 20
<212> TYPE: DNA
<213> ORGANISM: homo sapiens hmap3F1 primer

<400> SEQUENCE: 41
ggcatcatgc aaacgacagt                                              20

<210> SEQ ID NO 42
<211> LENGTH: 19
<212> TYPE: DNA
<213> ORGANISM: hmap3R1 primer

<400> SEQUENCE: 42
actgcgccga cctttgatt                                               19

<210> SEQ ID NO 43
<211> LENGTH: 25
<212> TYPE: DNA
<213> ORGANISM: human hmap3P1 primer

<400> SEQUENCE: 43
agagccaatc atcacggagg gatcc                                        25

<210> SEQ ID NO 44
<211> LENGTH: 22
<212> TYPE: DNA
<213> ORGANISM: homo sapiens map2bF primer

<400> SEQUENCE: 44
ttggaagact gttcacgcaa gt                                           22

<210> SEQ ID NO 45
<211> LENGTH: 20
<212> TYPE: DNA
<213> ORGANISM: homo sapiens map2bR primer

<400> SEQUENCE: 45
gtcaccggca ttgggagtat                                              20

<210> SEQ ID NO 46
<211> LENGTH: 31
<212> TYPE: DNA
<213> ORGANISM: homo sapiens map2bP primer

<400> SEQUENCE: 46
tggatgttct ctcaataatt gtgctgccca t                                 31

<210> SEQ ID NO 47
<211> LENGTH: 23
<212> TYPE: DNA
<213> ORGANISM: homo sapiens mp3bF primer
```

-continued

```
<400> SEQUENCE: 47
aacgtgctct gtcatggtat tcc                                                23

<210> SEQ ID NO 48
<211> LENGTH: 27
<212> TYPE: DNA
<213> ORGANISM: homo sapiens mp3bR primer

<400> SEQUENCE: 48
agccattgta atagactgtg acatcaa                                            27

<210> SEQ ID NO 49
<211> LENGTH: 35
<212> TYPE: DNA
<213> ORGANISM: homo sapiens mp3bP primer

<400> SEQUENCE: 49
acagtcgacc tcttcaggat ggagatatta tcaac                                   35

<210> SEQ ID NO 50
<211> LENGTH: 24
<212> TYPE: DNA
<213> ORGANISM: homo sapiens mp3cF primer

<400> SEQUENCE: 50
catggagaca cctctgaaac attt                                               24

<210> SEQ ID NO 51
<211> LENGTH: 22
<212> TYPE: DNA
<213> ORGANISM: homo sapiens mp3cR primer

<400> SEQUENCE: 51
cctggcaacc tccactaact tt                                                 22

<210> SEQ ID NO 52
<211> LENGTH: 24
<212> TYPE: DNA
<213> ORGANISM: homo sapiens mp3cP primer

<400> SEQUENCE: 52
cacattcgtc ctcattgccc acca                                               24

<210> SEQ ID NO 53
<211> LENGTH: 20
<212> TYPE: DNA
<213> ORGANISM: homo sapiens hcycmesF primer

<400> SEQUENCE: 53
cccaccgtgt tcttcgacat                                                    20

<210> SEQ ID NO 54
<211> LENGTH: 22
<212> TYPE: DNA
<213> ORGANISM: homo sapiens hcycmesR primer

<400> SEQUENCE: 54
tttctgctgt ctttgggacc tt                                                 22

<210> SEQ ID NO 55
<211> LENGTH: 24
<212> TYPE: DNA
<213> ORGANISM: homo sapiens hcycmesP primer
```

```
<400> SEQUENCE: 55
cgcgtctcct ttgagctgtt tgca                                              24

<210> SEQ ID NO 56
<211> LENGTH: 24
<212> TYPE: DNA
<213> ORGANISM: homo sapiens revmp3cP primer

<400> SEQUENCE: 56
cacattcgtc cacattgccc acca                                              24

<210> SEQ ID NO 57
<211> LENGTH: 20
<212> TYPE: PRT
<213> ORGANISM: MetAP1 peptide antigen 1

<400> SEQUENCE: 57

Asn Glu Thr Phe Phe Val Gly Glu Val Asp Asp Gly Ala Arg Lys Leu
  1               5                  10                  15

Val Gln Thr Thr
             20

<210> SEQ ID NO 58
<211> LENGTH: 20
<212> TYPE: PRT
<213> ORGANISM: MetAP2 peptide antigen

<400> SEQUENCE: 58

Cys Ala Phe Thr Val Thr Phe Asn Pro Lys Tyr Asp Thr Leu Leu Lys
  1               5                  10                  15

Ala Val Lys Asp
             20

<210> SEQ ID NO 59
<211> LENGTH: 20
<212> TYPE: PRT
<213> ORGANISM: MetAP3 peptide antigen

<400> SEQUENCE: 59

Ser Glu Thr Phe Leu Val Gly Asn Glu Asp Glu Ala Gly Lys Lys Leu
  1               5                  10                  15

Val Glu Val Ala
             20

<210> SEQ ID NO 60
<211> LENGTH: 20
<212> TYPE: PRT
<213> ORGANISM: MetAP1 blocking peptide antigen

<400> SEQUENCE: 60

Gly Trp Gln Asp Glu Thr Trp Pro Asp Gly Trp Thr Ala Val Thr Arg
  1               5                  10                  15

Asp Gly Lys Arg
             20

<210> SEQ ID NO 61
<211> LENGTH: 20
<212> TYPE: PRT
<213> ORGANISM: MetAP2 blocking peptide antigen

<400> SEQUENCE: 61
```

```
Cys Ser His Tyr Met Lys Asn Phe Asp Val Gly His Val Pro Ile Arg
1               5                   10                  15

Leu Pro Arg Thr
            20

<210> SEQ ID NO 62
<211> LENGTH: 20
<212> TYPE: PRT
<213> ORGANISM: MetAP3 blocking peptide antigen

<400> SEQUENCE: 62

Gly Ser Pro Glu Phe Lys Val Leu Glu Asp Ala Trp Thr Val Val Ser
1               5                   10                  15

Leu Asp Asn Gln
            20
```

METHIONINE AMINOPEPTIDASE TYPE 3

PRIORITY

The present application, claims priority under Title 35, United States Code, § 119 of U.S. Provisional Application Ser. No. 60/125,139, filed Mar. 11, 1999.

FIELD OF THE INVENTION

The present invention relates to a human cDNA encoding a methionine aminopeptidase type-3 (MetAP-3) protein. The invention also relates to nucleic acid molecules associated with or derived from this cDNA including complements, homologues and fragments thereof, and methods of using these nucleic acid molecules, to generate, for example, polypeptides and fragments thereof. The invention also provides methods of using the nucleic acids, for example, to produce a protein and fragments thereof and to screen for compounds or compositions that preferentially or specifically effect the activity of a MetAP-3 protein.

BACKGROUND

Angiogenesis, the process of new blood vessel formation, is essential for the exponential growth of solid tumors and tumor metastasis. Radiological and cytocidal treatments, combined with regimens involving selective inhibitors of angiogenesis should lead to dramatic reductions in tumor growth. One angiogenesis inhibitor was first discovered as a fungal contaminant of bovine endothelial cell cultures that inhibited cell proliferation (Ingber et al. *Nature* 348:555–557, 1990). This product was subsequently isolated from *A. fumagatus* and identified as fumagillin, a well-known amebicide and antibiotic (McCowen et al., *Science* 113:202–203 (1951)). Fumagillin was found to be a potent inhibitor of endothelial cell proliferation, but its therapeutic window was insufficient for further clinical advancement. TNP-470, a fumagillin-like derivative with 50-fold higher potency, was subsequently developed from a directed chemical approach (Ingber et al., *Nature* 348:555–557 (1990), Kusaka et al., *Biochem. Biophys. Res. Commun.* 174:1070–1076 (1991)). This compound's therapeutic use is limited, however, by its lack of oral availability and dose-limiting neurotoxicity.

Until recently, the molecular target for fumagillin or TNP-470 was unknown. In 1997, the target protein was isolated, purified, and identified by mass spectrometry as the type-2 methionine aminopeptidase (MetAP-2). Both fumagillin and TNP-470 are now known as potent inhibitors of MetAP-2, but not the type-1 enzyme. This result identified MetAP-2 as an anti-angiogenesis target (Sin et al. *Proc. Natl. Acad. Sci. (U.S.A.)* 94:6099–6103 (1997), Griffith et al. *Chem. Biol.* 4:461–471 (1997).

The methionine aminopeptidases were first isolated from eubacteria and shown to be cobalt-containing enzymes with molecular masses of about 30 kDa (Ben-Bassat et al., *J. Bacteriol.* 169:751–757 (1987), Suh et al., *Gene* 169:17–23 (1996), and Miller et al., *Proc. Natl. Acad. Sci. (U.S.A.)* 91:2473–2477, 1987). The structure of these enzymes consists of a novel protease fold with pseudosymmetry around a pair of cobalt ions (Roderick and Matthews, *Biochemistry* 32:3907–3912, 1993).

Enzymes with the same substrate specificity, but with larger molecular masses, were isolated from yeast and pig. Highly homologous regions at the C-terminal domain (~30 kDa) of the eukaryotic and the prokaryotic forms were discovered, although the N-terminal domain of the eukaryote enzymes was found to be unique (Kendall and Bradshaw, *J. Biol. Chem.* 267:20667–20673 (1992)). The N-terminal domain of the yeast enzyme contained sequences consistent with two zinc-finger structures, indicating a potential site of nucleic acid interaction. This class of enzyme was designated methionine peptidase Type I (MetAP-1). The porcine enzyme lacked the zinc-binding domains, but contained a block of polylysine and aspartic residues within the N-terminal domain, and was described as Type II (MetAP-2). Both isozymes have been found from Archebacteria to man, indicating a critical metabolic function (Arfin et al. *Proc. Natl. Acad. Sci. (U.S.A.)* 92:7714–7718 (1995), Bradshaw et al., *TIBS* 23: 2.63–267 (1998)).

Methionine aminopeptidase-2 is bi-functional. One action is the removal of the N-terminal methionine residues from their protein substrates. MetAP-2 can also bind to and prevent phosphorylation of the α-subunit of the peptide change initiation factor eIF-2 by one or more eIF-2 kinases (Datta et al., *Proc. Natl. Acad. Sci. USA* 85: 3324–2238 1(1988), Wu et al., *J. Biol. Chem.* 268:10796–10781 (1993)). This action promotes protein synthesis within the cell. The eIF-2 phosphorylation inhibitory activity of MetAP-2 is unaffected by TNP-470 binding, indicating that the loss of aminopeptidase activity is involved in the anti-angiogenic activity of TNP-470 (Griffith et al., *Chem. Biol.* 4:461–471 (1997)). The function of methionine peptidase activity in endothelial cell proliferation during tumorigenesis is unclear, although inhibition of MetAP-2 may play a role in altering the stability of one or more protein(s) whose abnormal presence or absence results in endothelial cell dysregulation. Several signaling proteins also appear to be modified by the covalent attachment of myristic acid to a glycine residue which occurs only after the initial amino-terminal methionine removal by MetAP-2 (Peseckis et al., *J. Biol. Chem.* 267:5107–5114 (1993)). Inhibition of methionine aminopeptidase activity may prevent this covalent attachment, resulting in improper functioning of a signal component specific to endothelial cell cycle regulation (Sin et al. *Proc. Natl. Acad. Sci. (U.S.A.)* 94:6099–6103 (1997)).

N-terminal processing agents, such as the methionine aminopeptidases, also function to initiate post-translational peptide or protein modifications which may control or induce activation, translocation, or protein turnover (Bradshaw et al., *TIBS* 23: 263–267 (1998)). Because this initial processing is important for normal protein functioning, it is possible that alteration of methionine aminopeptidase activity is a factor in a variety of diseases, including angiogenesis. Therapies can thus be developed which can modify methionine aminopeptidase activity to restore proper protein processing.

Methionine aminopeptidase activity can also be used to modify recombinant proteins expressed and harvested from *E. coli* or other expression systems. Recombinant proteins that retain the N-terminal methionine, in some cases, have biological characteristics that differ from the native species that retain the N-terminal methionine, including the induction of undesireable antibodies. Using a methionine aminopeptidase for recombinant protein modification provides a low-cost method of generating potentially life-saving therapeutic proteins and to mimic the structure of native protein species which are used to combat or eliminate the causes of various diseases (Sandman et al., Biotechnology (N Y) 13:504–6 (1995)).

Clearly, an understanding of methionine aminopeptidase activity and its role in various tissues can provide useful therapeutic and diagnostic insight into angiogenesis and tumor metastasis. The known MetAP-2 inhibitors are not good candidates for clinical use as angiogenesis inhibitors due to their neurotoxic effects. Differential expression of mammalian MetAP-1, MetAP-2, or other unidentified methionine aminopeptidases may partially or totally account for the observed variation in sensitivity of different cell types to inhibition by TNP-470 and other MetAP-2 inhibitors, and thus account for the observed toxicity of these drugs.

SUMMARY OF THE INVENTION

One aspect of the present invention is to provide a novel methionine aminopeptidase, MetAP-3, and its nucleic acids, proteins, peptides, fragments, and homologues.

Another aspect of the invention is to provide new and advantageous targets to screen for diagnostic and therapeutic agents and compositions useful for diagnosis or treatment of angiogenesis-related diseases.

The invention provides a substantially-pure nucleic acid comprising a nucleic acid sequence selected from the group consisting of: SEQ NO: 7 or complements thereof; nucleic acid sequences that specifically hybridize to SEQ NO: 7 or complements thereof, especially those that hybridize under stringent conditions; nucleic acid sequences encoding a MetAP-3 protein or fragment thereof, or complement of these nucleic acid sequences; and nucleic acid sequences encoding the amino acid sequence of SEQ NO: 8, or complements thereof.

In one embodiment, the present invention relates to a substantially-pure nucleic acid selected from the group consisting of: a nucleic acid molecule comprising SEQ NO: 7 or its complement, and fragments of either having a length of about 12 to about 650 nucleotides, and a nucleic acid molecule that encodes a protein having a sequence of SEQ NO: 8 or a fragment of any having a length of about 10 to about 215 amino acids.

The present invention also relates to a nucleic acid encoding a fragment of a MetAP-3 protein, wherein the nucleic acid is about 12 to 650 nucleotides in length and has from about 99% to about 70% identity to a fragment of SEQ NO: 7.

In a particularly useful embodiment, a substantially-pure nucleic acid of the invention will specifically hybridize to a nucleic acid molecule encoding MetAP-3 or a complement thereof and fail to specifically hybridize to a nucleic acid molecule encoding MetAP-1, MetAP-2 or a complement of either.

The present invention also provides a substantially-pure MetAP-3 nucleic acid molecule which comprises a nucleic acid sequence that is identical to at least about 12 contiguous nucleotides of SEQ NO: 7 or its complement.

In a further embodiment, the present invention relates to a substantially-pure MetAP-3 protein or fragment thereof encoded by a nucleic acid sequence encoding a protein having an amino acid sequence of SEQ NO: 8 or a fragment of SEQ NO: 8 having a length of about 10 to 215 amino acids.

The present invention further relates to a substantially-pure MetAP-3 protein or fragment thereof comprising at least 10 consecutive amino acids of SEQ NO: 8, wherein the protein possesses a MetAP activity.

In another embodiment, the present invention relates to a transformed cell having a nucleic acid molecule which comprises a structural nucleic acid molecule, wherein said structural nucleic acid molecule encodes a MetAP-3 protein, peptide, or fragment thereof.

In yet another embodiment, the present invention provides a method for determining a level or pattern of MetAP-3 expressed in a cell comprising: (A) incubating, under conditions permitting nucleic acid hybridization, a marker nucleic acid molecule, the marker nucleic molecule capable of specifically hybridizing to a nucleic acid, molecule that encodes MetAP-3 or complement thereof under high stringency conditions and the marker nucleic acid molecule incapable of specifically hybridizing to a nucleic acid molecule that encodes MetAP-1 or MetAP-2 complements of either under high stringency conditions, with a nucleic acid molecule derived from or within the cell; (B) permitting hybridization between the marker nucleic acid molecule and the complementary nucleic acid molecule derived from or within the cell; and (C) detecting the level or pattern of the hybridization. The level or pattern of the hybridized complementary nucleic acid is predictive of the level or pattern of the MetAP-3 protein.

The present invention also relates to a method for detecting the presence of a mutation affecting the level or pattern of MetAP-3 expression comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule having a nucleic acid sequence of SEQ NO: 8 or the complement thereof, with a nucleic acid molecule derived from or within said cell, wherein hybridization between the marker nucleic acid molecule and the nucleic acid molecule derived from or within the cell permits the detection of a polymorphism whose presence is predictive of a mutation affecting the level or pattern of the MetAP-3 protein in the cell; (B) permitting hybridization between the marker nucleic acid molecule and the nucleic acid molecule derived from or within the cell; and (C) detecting the presence of the hybridization.

In another embodiment, the present invention provides a method for detecting the presence or absence of angiogenic activity in a mammal which comprises assaying the concentration of a molecule whose concentration is dependent upon the expression of a MetAP-3 gene, the molecule being present in a sample of cells or bodily fluid of said mammal, and comparing the concentration of that molecule in the angiogenesis model animal with the concentration of the molecule in a sample of cells or bodily fluid of a control mammal.

In a further embodiment, the present invention relates to a prognostic or diagnostic method for identifying angiogenesis of a tumor in a patient which comprises the steps: (A) incubating, under conditions permitting nucleic acid hybridization, a marker nucleic acid molecule, said marker nucleic acid molecule comprising a nucleotide sequence that specifically hybridizes to a polynucleotide that is linked to a MetAP-3 gene, with a nucleic acid molecule derived from or within a cell or a bodily fluid of said patient, wherein nucleic acid hybridization between said marker nucleic acid molecule and said nucleic acid molecule derived from or within a cell or bodily fluid of said patient is capable of detecting a polymorphism whose presence is predictive of a mutation affecting MetAP-3 response in said patient; (B) permitting hybridization between said marker nucleic acid molecule and said nucleic acid molecule derived from or within a cell or bodily fluid of said patient; and (C) detecting the presence hybridization.

In another embodiment, the present invention relates to a method of determining an association between a polymorphism and a trait comprising: (A) hybridizing a nucleic acid molecule specific for the polymorphism to genetic material of a cell, wherein said nucleic acid molecule comprises a nucleotide sequence of SEQ NO: 5 or complements thereof; and (B) calculating the degree of association between the polymorphism and the trait.

The present invention also relates to a method of producing a cell capable of overexpressing a MetAP-3 protein comprising: (A) introducing into a cell with a functional nucleic acid molecule, comprising a nucleic acid sequence of SEQ NO: 5, and (B) culturing the cell. The invention also provides a cell and progeny of a cell produced by such a method.

In another embodiment, the present invention relates to a method for detecting a modification in the methionine-removal activity of cells in a mammal, comprising assaying the concentration of a molecule whose concentration is dependent upon the expression of a MetAP-3 protein, the molecule being present in a sample of cells or bodily fluid of the mammal, and comparing to the concentration of that molecule with that in a sample of cells or bodily fluid from a control mammal.

The present invention also relates to a composition comprising an oligodeoxynucleotide and a pharmaceutically acceptable carrier, the oligodeoxynucleotide comprising a sequence set forth in one of: SEQ NO: 7 or its complements or fragment of either, having a length of about 12 to about 650 nucleotides.

The present invention further relates to a composition comprising a polypeptide and a pharmaceutically acceptable carrier, said polypeptide comprising an amino acid sequence encoded by a nucleic acid comprising SEQ NO: 7, or its complement or a fragment of either, having a length of about 12 to about 650 nucleotides; a nucleic acid encoding a protein having a sequence of SEQ NO: 8 or a fragment of SEQ NO: 8 having a length of about 10 to about 215 amino acids.

In another embodiment, the present invention provides a method of producing a cell capable of expressing reduced levels of a MetAP-3 protein comprising: (A) introducing into a cell a functional nucleic acid molecule, comprising a nucleic acid sequence of SEQ NO: 7, wherein the functional nucleic acid molecule results in co-suppression of the MetAP protein; and (B) culturing the cell. The invention also provides a cell and progeny of a cell produced by such a method.

In a further embodiment, the present invention provides a method for reducing expression of a MetAP-3 protein in a cell comprising: (A) introducing into a cell with a nucleic acid molecule, said nucleic acid molecule having an exogenous promoter region which functions in a cell to cause the production of a mRNA molecule, wherein said exogenous promoter region is linked to a transcribed nucleic acid molecule having a transcribed strand and a non-transcribed strand, wherein the transcribed strand is complementary to a nucleic acid molecule having a nucleic acid sequence of SEQ NO: 7 or its complement and said transcribed strand is complementary to an endogenous mRNA molecule; and (B) culturing said cell. The invention also provides a cell and progeny of a cell produced by such a method.

The present invention also provides a method for detecting a compound or composition that modifies the protein phosphorylation activity of a MetAP-3 protein, or a fragment or fusion thereof comprising contacting the compound or composition with a MetAP-3 protein in the presence of a phosphorylating activity and a substrate, allowing a phosphorylation to occur, and detecting the phosphorylation of the substrate in comparison to a control.

The invention also provides a method of isolating a nucleic acid that encodes a MetAP-3 protein or fragment thereof comprising: (A) incubating, under conditions permitting hybridization, a first nucleic acid molecule comprising SEQ NO: 5, or the complement thereof, with a second nucleic acid molecule obtained or derived from a cell; (B) permitting hybridization between said first nucleic acid molecule and said second nucleic acid molecule; and (C) isolating said second nucleic acid molecule. The invention also provides a cell and progeny of a cell produced by such a method.

In a further embodiment, the present invention provides a method for identifying a molecule, compound, or composition that effects the MetAP activity of a MetAP-3 protein, comprising providing a MetAP-3 protein, contacting the MetAP-3 protein with a test sample comprising a molecule, compound, or composition, and comparing the MetAP activity with a control.

The invention further provides a method of using a, MetAP-3 protein or fragment thereof in an assay for screening test substances for the ability to modulate or maintain an activity possessed by a MetAP-3 protein, comprising contacting a MetAP-3 protein or fragment with a test substance, and determining the presence or level of MetAP-3 activity compared to a control.

BRIEF DESCRIPTION OF THE DRAWINGS

FIG. 1 shows the phylogenetic relationship displayed as a tree diagram, between the amino acid sequences of various methionine aminopeptidases, including MetAP types 1, 2, and 3, and the relationship between full-length human MetAP-3, including the partial amino acid sequence encoded by the clone designated MAP-3 insertion (see text for details).

FIG. 2 shows multiple amino acid sequence alignments of various methionine aminopeptidases FIG. 2 shows a pairwise alignment between two clones encoding MetAP-3, designated map3gt and GT, to show the position of the 50 base pair insert present in the clone GT, later designated MAP-3 insertion (see text for details).

FIG. 3 shows a restriction map of the baculovirus donor plasmid pMON57801, containing the MetAP-1 coding sequence under the control of the *Autographa californica* nuclear polyhedrosis virus (AcNPV) polyhedrin promoter (pPolh). The expression cassette containing a gentamycin resistance marker, nPolh, a His(6) tag, MetAP-1, and an SV40 poly-A termination signal is flanked by the short arms of the bacterial transposon Tn7. The mini-Tn7 cassette is transposed to an attTn7 attachment site which resides on baculovirus shuttle vector (bacmid) harbored in *E. coli* cells. Composite bacmids containing the min-Tn7 expression cassette are isolated from bacteria and transfected into insect cells to generate pure stocks of recombinant baculoviruses.

FIG. 4 shows a restriction map of the baculovirus donor plasmid pMON57800, containing the MetAP-1 coding sequence under the control of the AcNPV polyhedrin promoter.

FIG. 5 shows a restriction map of the baculovirus donor plasmid pMON56503, containing the MetAP-3 coding sequence fused to a His(6) tag under the control of the AcNPV polyhedrin promoter.

FIG. 6 shows a restriction map of the baculovirus donor plasmid pMON56502, containing the MetAP3 coding sequence under the control of the AcNPV polyhedrin promoter.

FIG. 7 shows a restriction map of the baculovirus donor plasmid pMON56500, containing the MetAP-2 coding sequence under the control of the AcNPV polyhedrin promoter.

FIG. 8 shows transcriptional profiling data comparing expression of cyclophilin, MetAP-1, MetAP-2, and MetAP-3 across various tissue samples FIG. 8 shows relative expression of cyclophilin, MetAP-1, MetAP-2, and MetAP-3, graphically displayed in FIGS. 9–11, across a library of tissue samples (See Example 4 for details).

FIG. 9 graphically displays the relative expression of MetAP-1 across a library of tissue samples.

FIG. 10 graphically displays the relative expression of MetAP-2 across a library of tissue samples.

FIG. 11 graphically displays the relative expression of MetAP-3 across a library of tissue samples.

FIGS. 12–14 show transcriptional profiling data comparing expression of cyclophilin, MetAP-1, MetAP-2, and MetAP-3 across various tissue samples FIG. 15 shows transcriptional profiling data comparing expression of cyclophilin, MetAP-1, MetAP-2, and MetAP-3 across various brain samples FIG. 15 shows relative expression of cyclophilin, MetAP-1, MetAP-2, and MetAP-3, graphically displayed in FIGS. 16–18, across a library of tissue samples (See Example 4 for details).

FIG. 16 graphically displays the relative expression of MetAP-3 across a library of brain tissue samples.

FIG. 17 graphically displays the relative expression of MetAP2 across a library of brain tissue samples.

FIG. 18 graphically displays the relative expression of MetAP-1 across a library of brain tissue samples.

Figure 1:
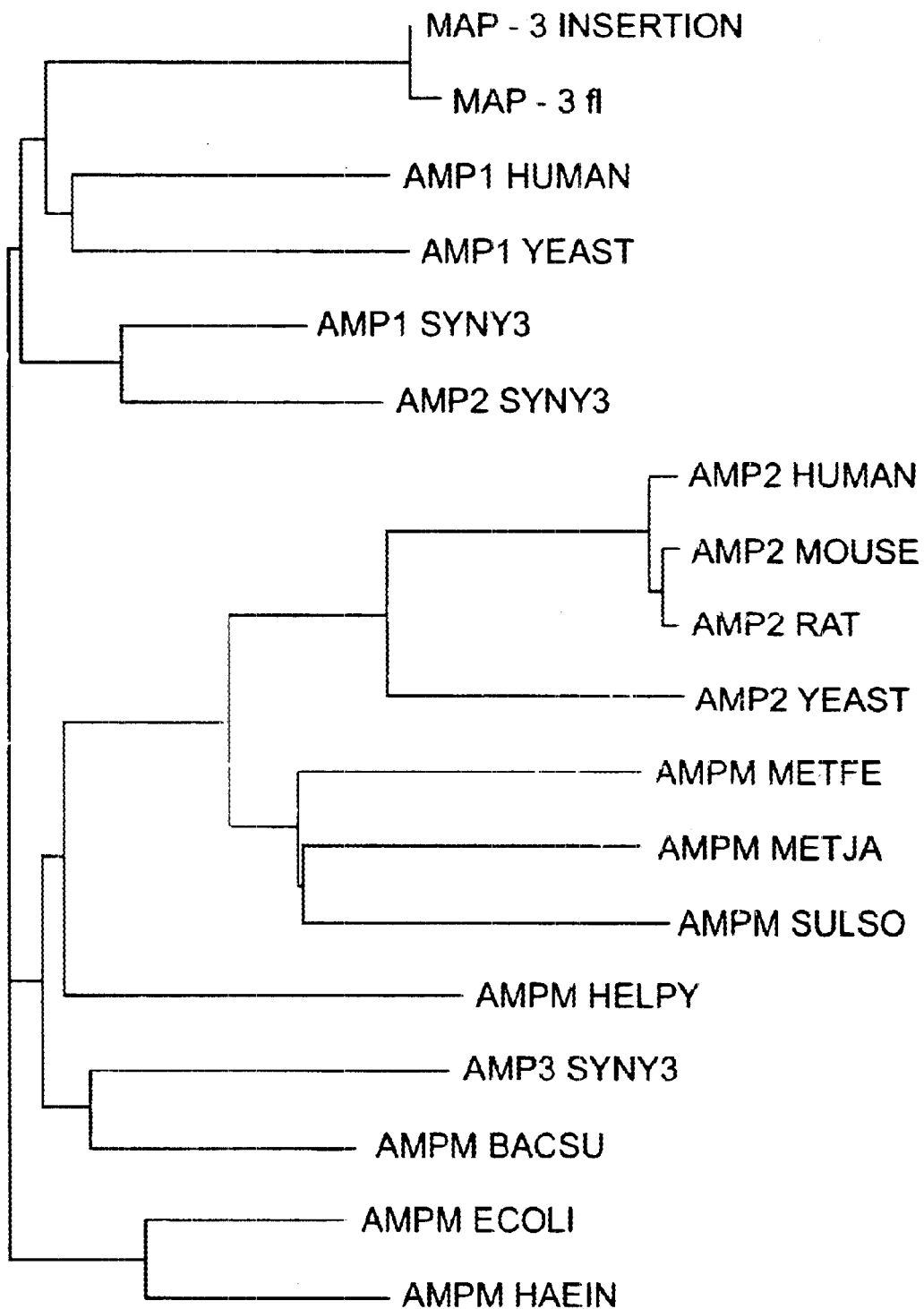
FIG. 1 displays phylogenetic trees showing the genetic relatedness of various methionine aminopeptidases

Table 1 Shows a Multiple Sequence Alignment of Various Aminopeptidases

Table 1 shows a multiple sequence alignment between the amino acid sequences of various methionine aminopeptidases, including MetAP types 1, 2, and 3, and the relationship between full-length human MetAP-3, including the partial amino acid sequence encoded by the clone designated MAP-3 insertion (see text for details, and Table 2 for a key to the SEQ ID NOS).

Table 2—Table of Sequences

Table 2 shows a listing of the sequences described in this application, including the SEQ ID NO, a brief description, the length, and type of sequence (nucleotide [DNA or RNA] or peptide [protein]).

These detailed descriptions are presented for illustrative purposes only and are not intended to be, and should not be taken as, a restriction to the scope of the invention or the claims that follow. Rather, they are merely some of the embodiments that one skilled in the art would understand from the entire contents of this disclosure.

All parts are by weight and temperatures are in Degrees centigrade unless otherwise indicated.

The following is a list of abbreviations and the corresponding meanings as used interchangeably herein:
  kb=kilobase(s)
  Mb=megabase(s)
  mg=milligram(s)
  ml or mL=milliliter(s)
  μg or ug=microgram(s)
  μl or ul=microliter(s)
  ODNs=oligonucleotides
  PCR=polymerase chain reaction
  RP-HPLC=reverse phase high performance liquid chromatography The following is a list definitions of various terms used herein:

The term "altered" means that expression differs from the expression response of cells or tissues not exhibiting the phenotype.

The term "amino acid(s)" means all naturally occurring L-amino acids, including norleucine, norvaline, homocysteine, and ornithine.

The term "chromosome walking" means a process of extending a genetic map by successive hybridization steps.

The term "complete complementarity" means that every nucleotide of one molecule is complementary to a nucleotide of another molecule.

The term "degenerate" means that two nucleic acid molecules encode for the same amino acid sequences but comprise different nucleotide sequences.

The term "exogenous genetic material" means any genetic material, whether naturally occurring or otherwise, from any source that is capable of being inserted into any organism.

The term "expression response" means a mutation affecting the level or pattern of the expression encoded in part or whole by one or more nucleic acid molecules.

The term "fragment" means a nucleic acid molecule whose sequence is shorter than the target or identified nucleic acid molecule and having the identical, the substantial complement, or the substantial homologue of at least 10 contiguous nucleotides of the target or identified nucleic acid molecule.

The term "fusion molecule" means a protein-encoding molecule or fragment thereof that upon expression, produces a fusion protein.

The term "fusion protein" means a protein or fragment thereof that comprises one or more additional peptide regions not derived from that protein.

The term "marker nucleic acid" means a nucleic acid molecule that is utilized to determine an attribute or feature (e.g., presence or absence, location, correlation, etc.) of a molecule, cell, or tissue.

A "MetAP-3 fragment" means a peptide or polypeptide whose amino acid sequence comprises a subset of the amino acid sequence of MetAP-3 protein.

A MetAP-3 protein means a peptide encoded by a nucleic acid sequence which specifically hybridizes to SEQ NO: 7 or its complement.

The term "mimetic" refers to a compound having similar functional and/or structural properties to another known compound or a particular fragment of that known compound.

The term "phenotype" means any of one or more characteristics of an organism, tissue, or cell.

The term "probe" means an agent that is utilized to determine an attribute or feature (e.g. presence or absence, location, correlation, etc.) of a molecule, cell, tissue, or organism.

The term "promoter" is used in an expansive sense to refer to the regulatory sequence(s) that control mRNA production.

The term "protein fragment" means a peptide or polypeptide molecule whose amino acid sequence comprises a subset of the amino acid sequence of that protein.

The term "protein molecule/peptide molecule" means any molecule that comprises five or more amino acids.

The term "recombinant" means any agent (e.g., DNA, peptide, etc.), that is, or results from, however indirectly, human manipulation of a nucleic acid molecule.

The term "selectable or screenable marker genes" means genes whose expression can be detected by a probe as a means of identifying or selecting for transformed cells.

The term "specifically bind" means that the binding of an antibody or peptide is not competitively inhibited by the presence of non-related molecules.

The term "specifically hybridizing" means that two nucleic acid molecules are capable of forming an anti-parallel, double-stranded nucleic acid structure.

The term "substantial complement" means that a nucleic acid sequence shares at least 80% sequence identity with the complement.

The term "substantial fragment" means a nucleic acid fragment which comprises at least 100 nucleotides.

The term "substantial homologue" means that a nucleic acid molecule shares at least 80% sequence identity with another.

The term "substantially hybridizing" means that two nucleic acid molecules can form an anti-parallel, double-stranded nucleic acid structure under conditions (e.g. salt and temperature) that permit hybridization of sequences that exhibit 90% sequence identity or greater with each other and exhibit this identity for at least about a contiguous 50 nucleotides of the nucleic acid molecules.

The term "substantially-purified" means that one or more molecules that are or may be present in a naturally-occurring preparation containing the target molecule will have been removed or reduced in concentration.

DETAILED DESCRIPTION OF THE INVENTION

I. Overview

The present invention is directed, in part, to the isolation of a nucleic acid encoding a MetAP-3 protein, which exhibits sequence homology to the highly conserved residues that coordinate the cobalt ions in MetAP-1 and MetAP-2. The phylogenetic relationship between the methionine aminopeptidases is shown in FIG. 1. MetAP-3 and MetAP-1/MetAP-2 exhibit different expression profiles, suggesting additional or different roles for MetAP-3 in cellular metabolism and in an organism as a whole. The present invention, comprising novel MetAP-3 nucleic acids, proteins, peptides, homologues, and fragments of either, provides new and advantageous targets to screen for diagnostic and therapeutic agents and compositions useful for diagnosis or treatment of angiogenesis-related diseases. Such diseases include but are not limited to angiogenesis associated with tumor growth and tumor metastasis, neovascularization induced by retinopathy, or hypoxia resulting from ischemic injury.

Figure 3:
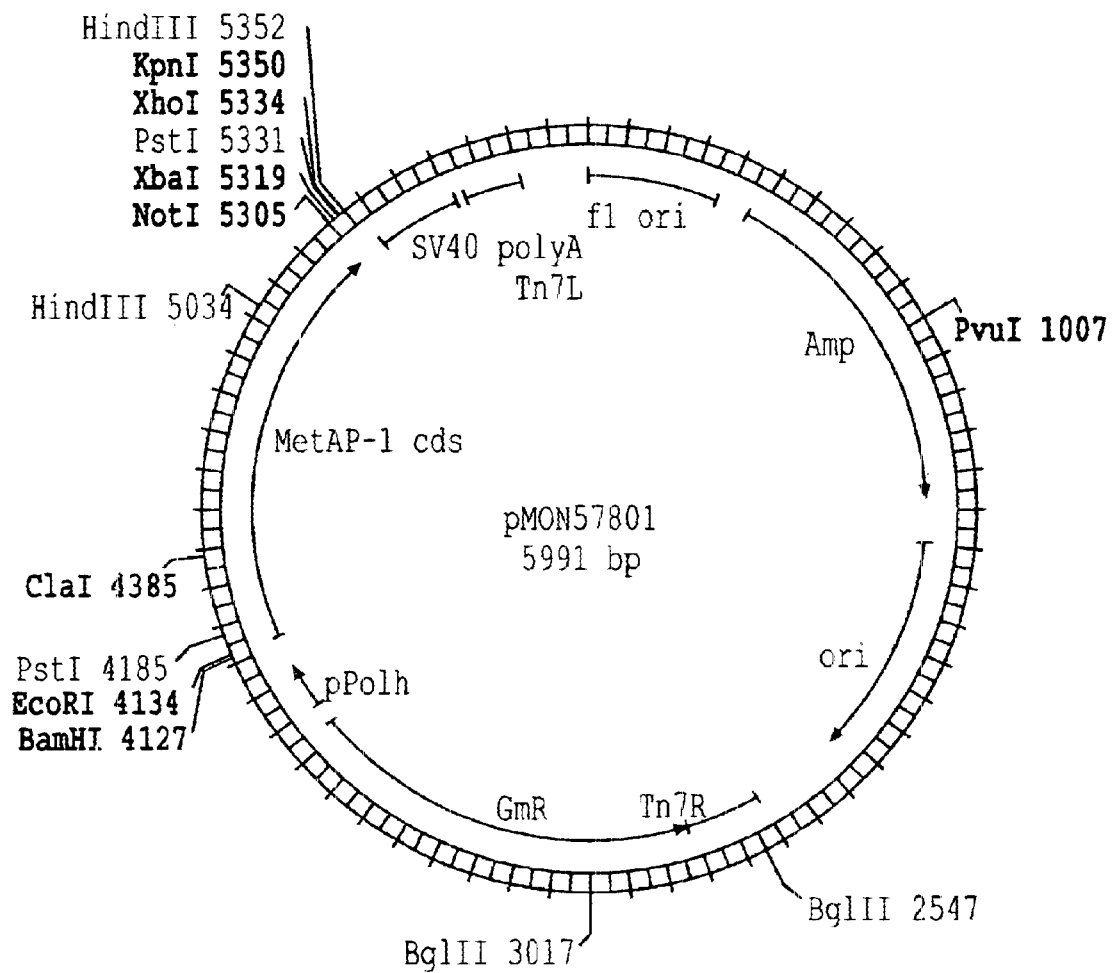
FIG. 3 shows a restriction map of the plasmid pMON57801
Figure 4:
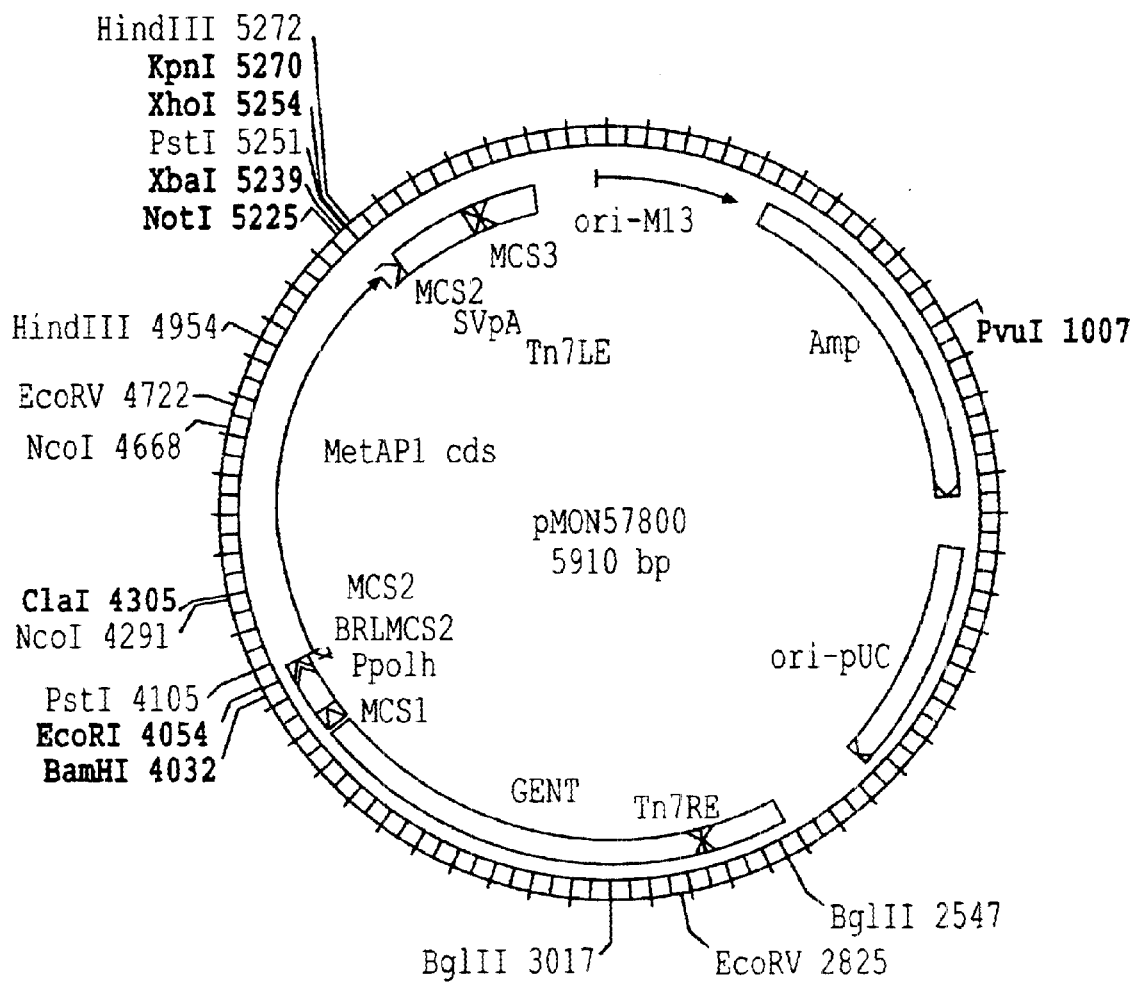
FIG. 4 shows a restriction map of the plasmid pMON57800
Figure 5:
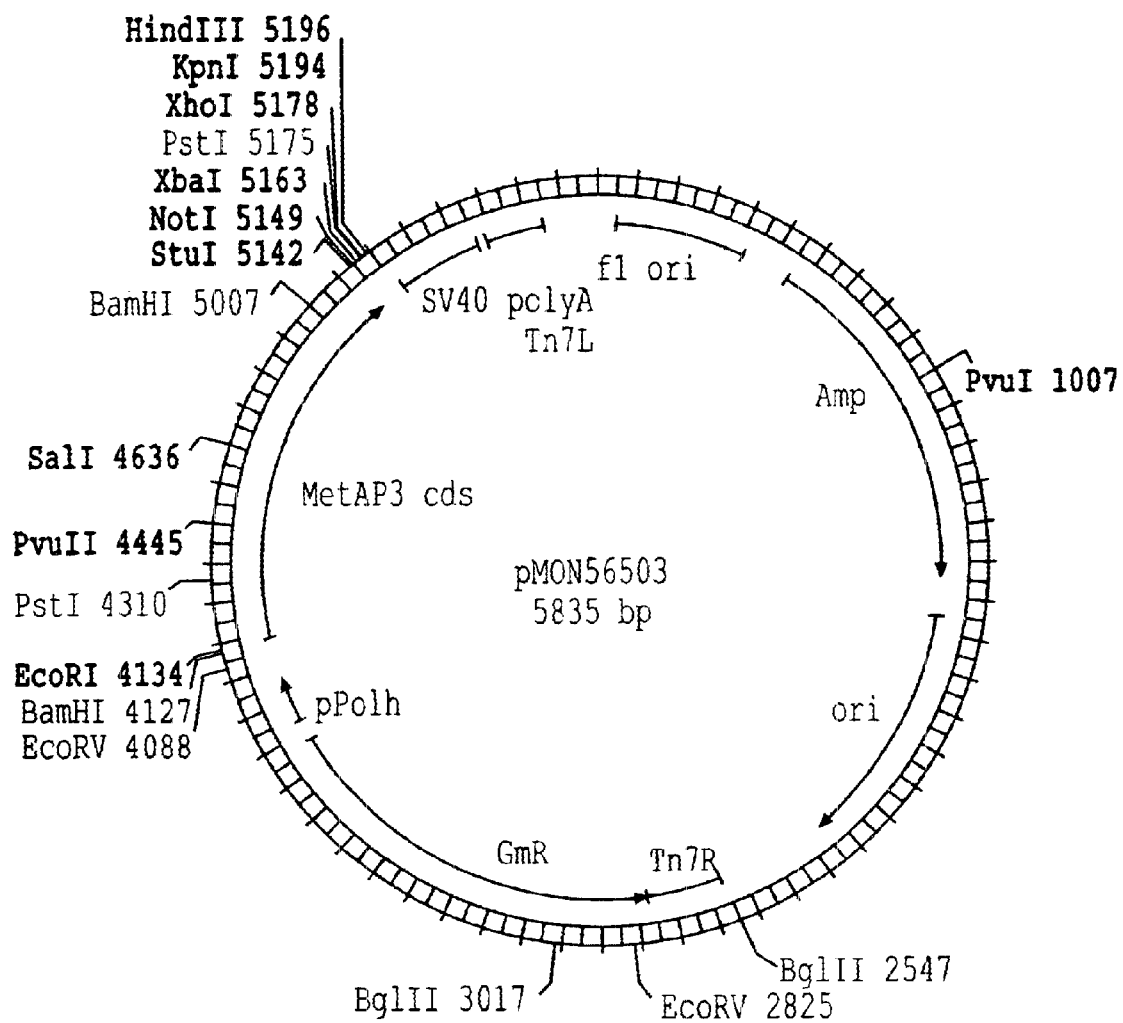
FIG. 5 shows a restriction map of the plasmid pMON57503
Figure 6:
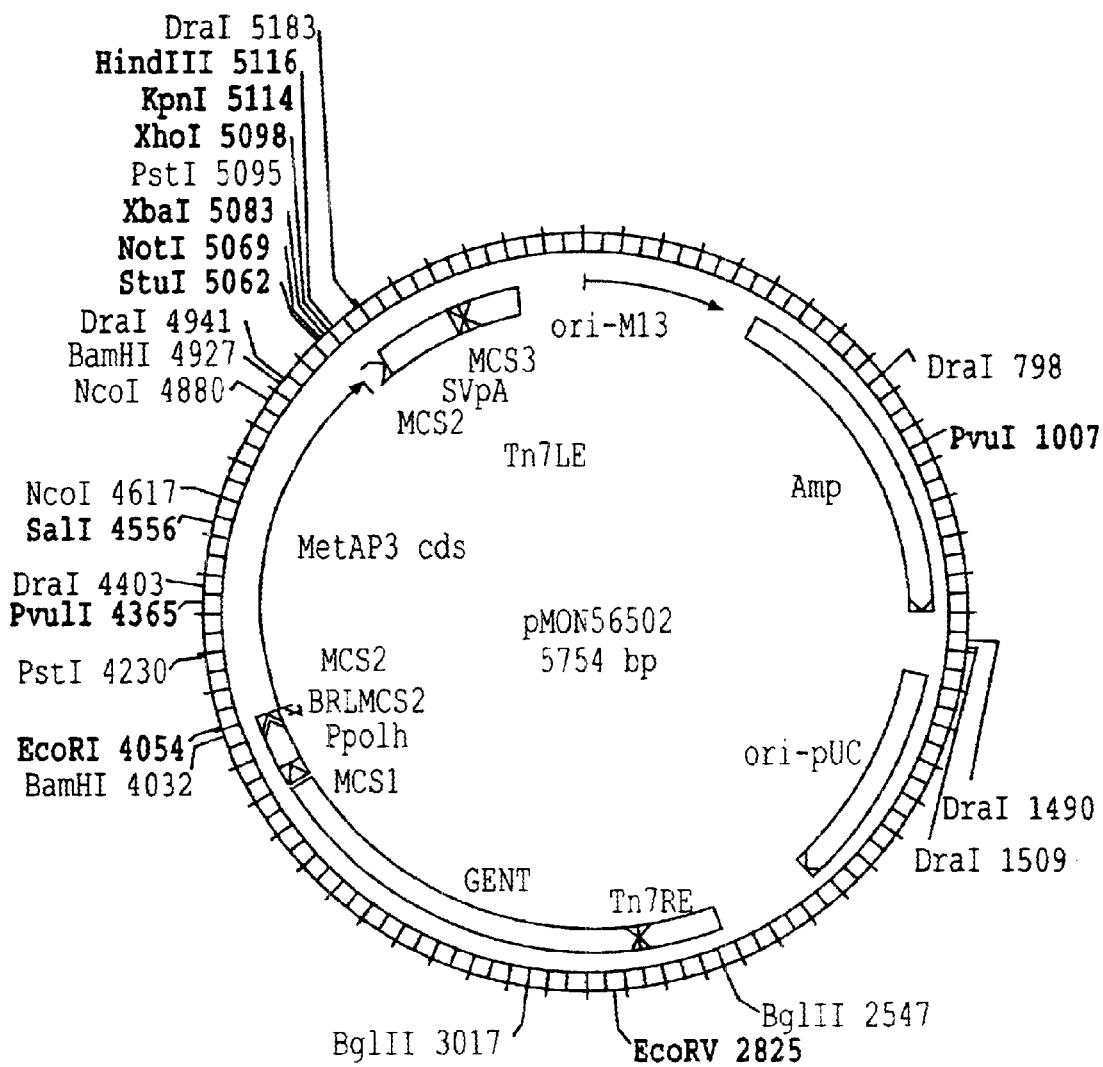
FIG. 6 shows a restriction map of the plasmid pMON56502
Figure 7:
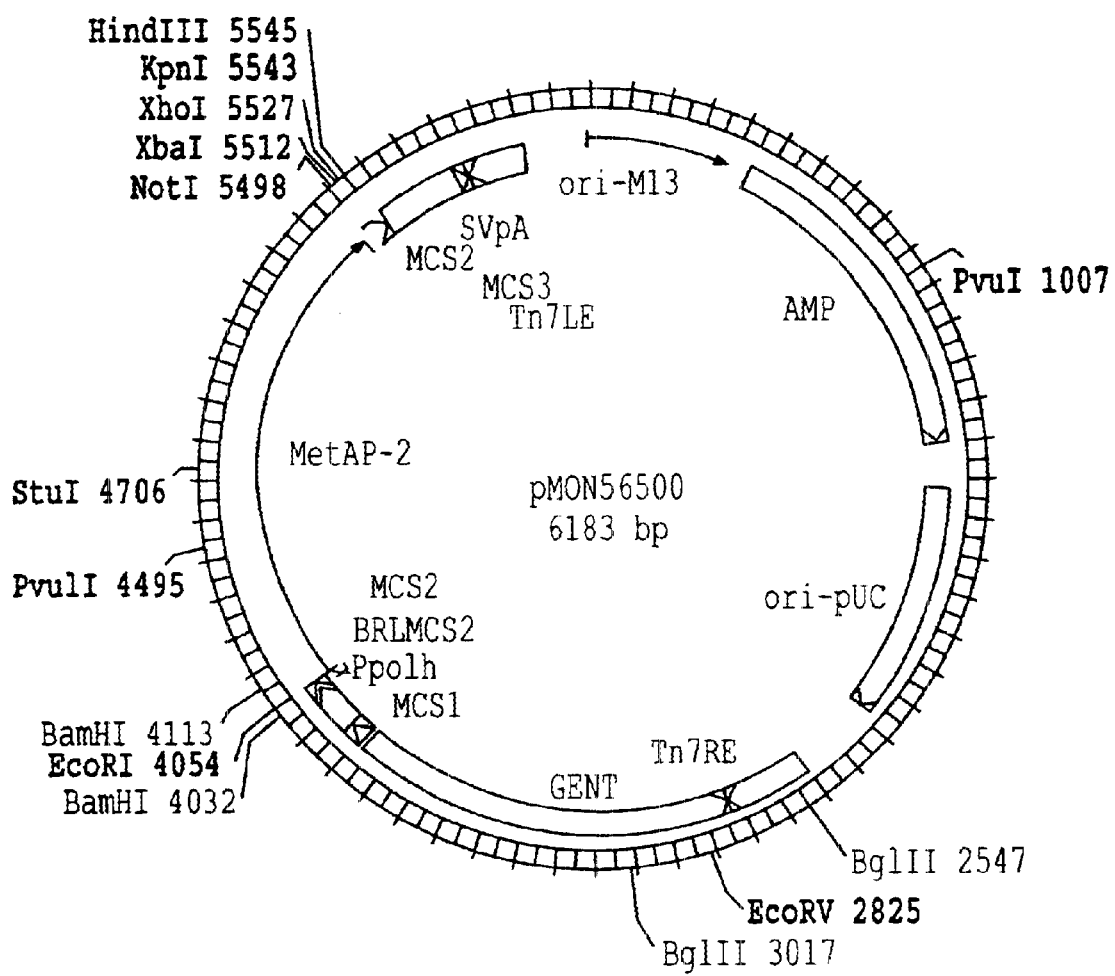
FIG. 7 shows a restriction map of the plasmid pMON56500
Figure 9:
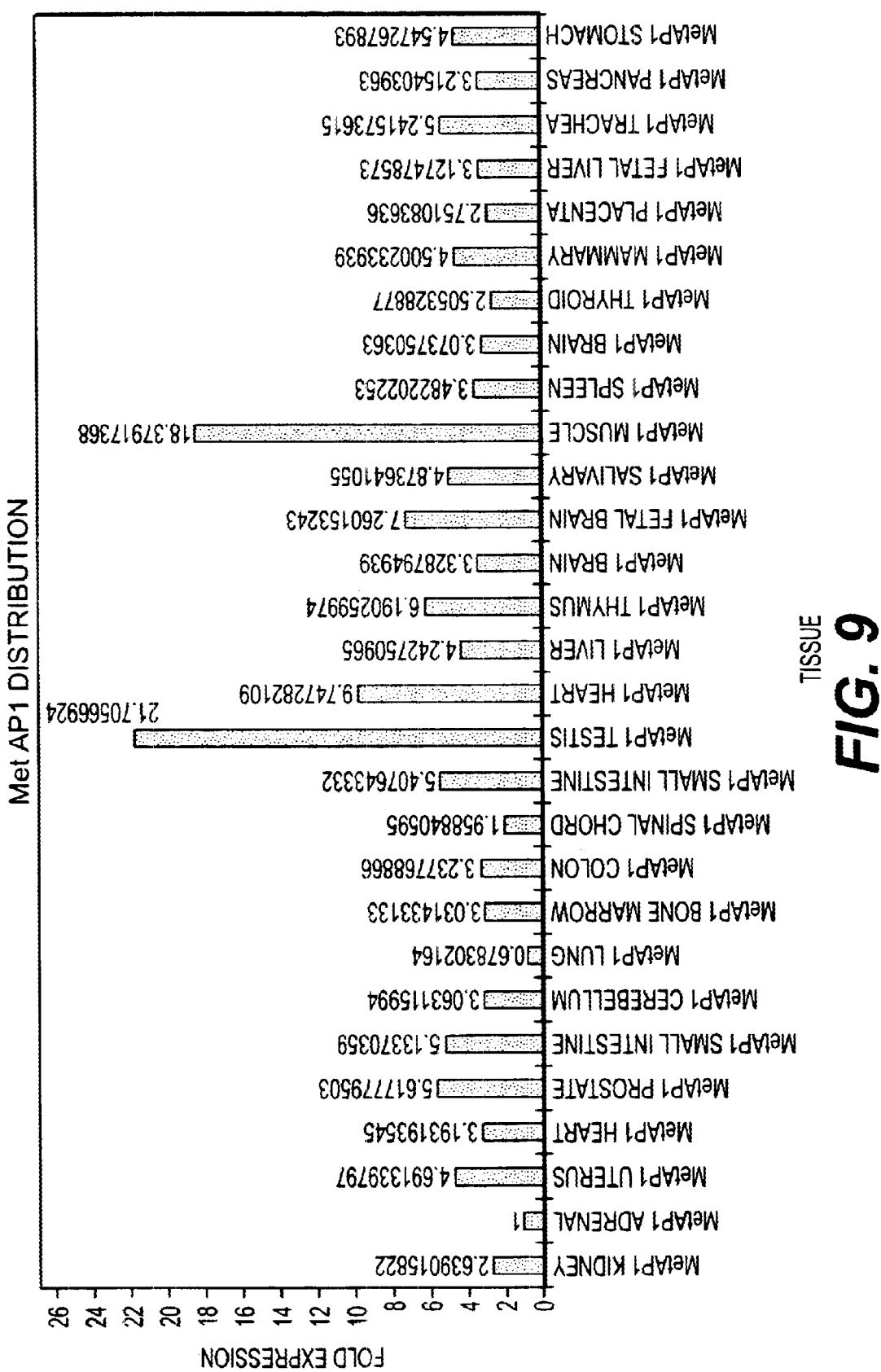
FIG. 9 shows the distribution of MetAP-1 transcripts across various tissues
Figure 10:
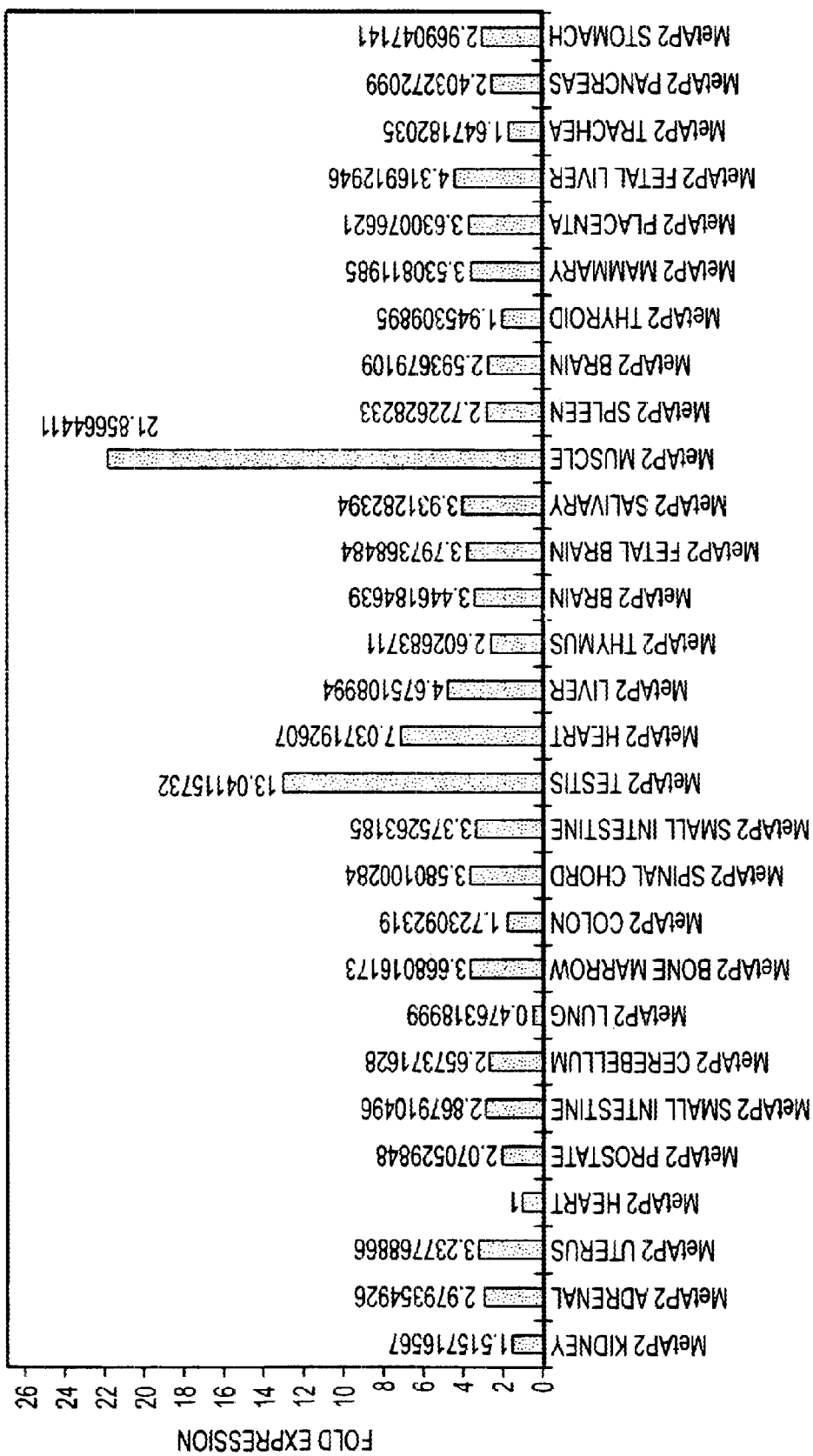
FIG. 10 shows the distribution of MetAP-2 transcripts across various tissues
Figure 11:
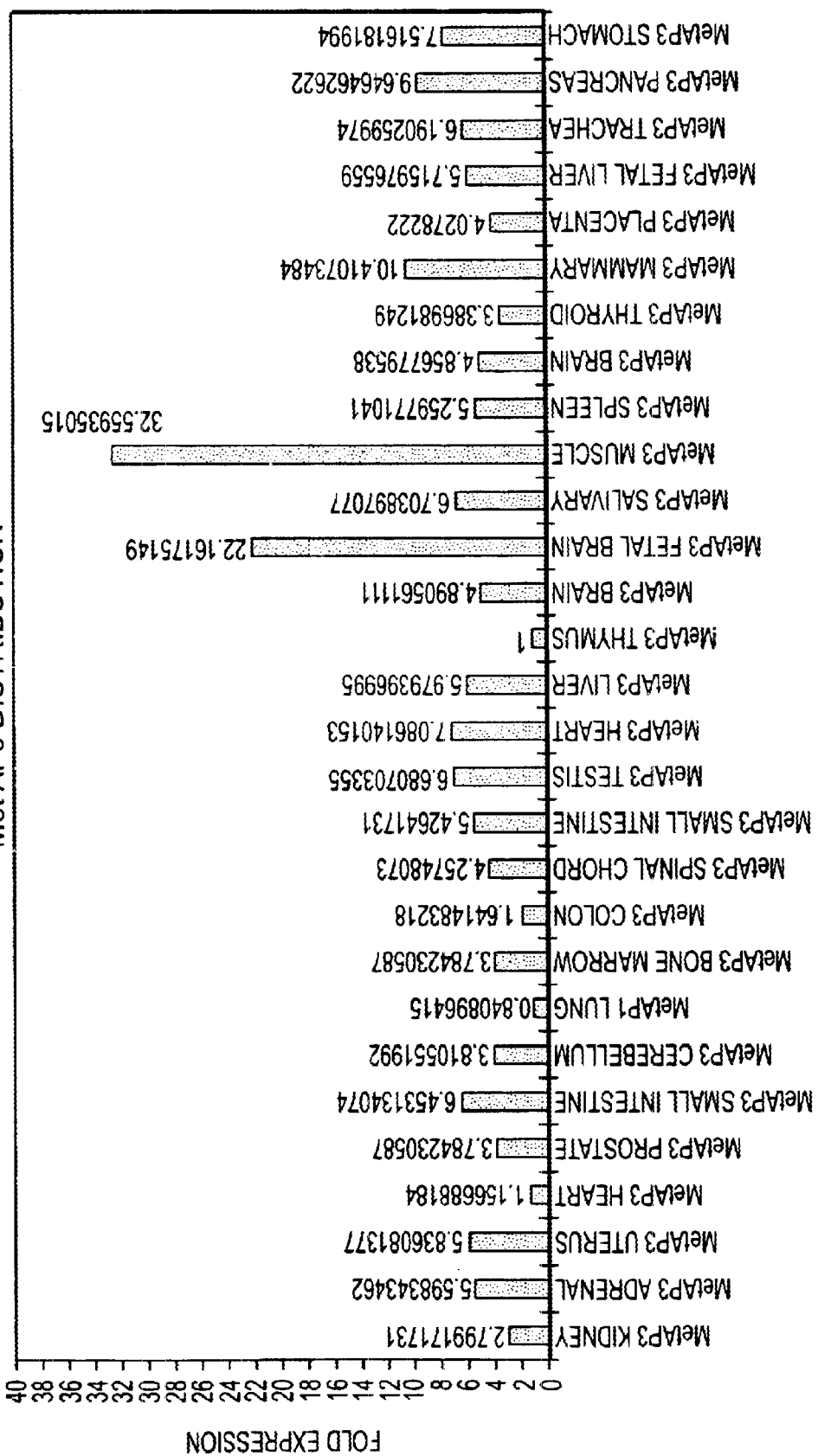
FIG. 11 shows the distribution of MetAP-3 transcripts across various tissues
Figure 16:
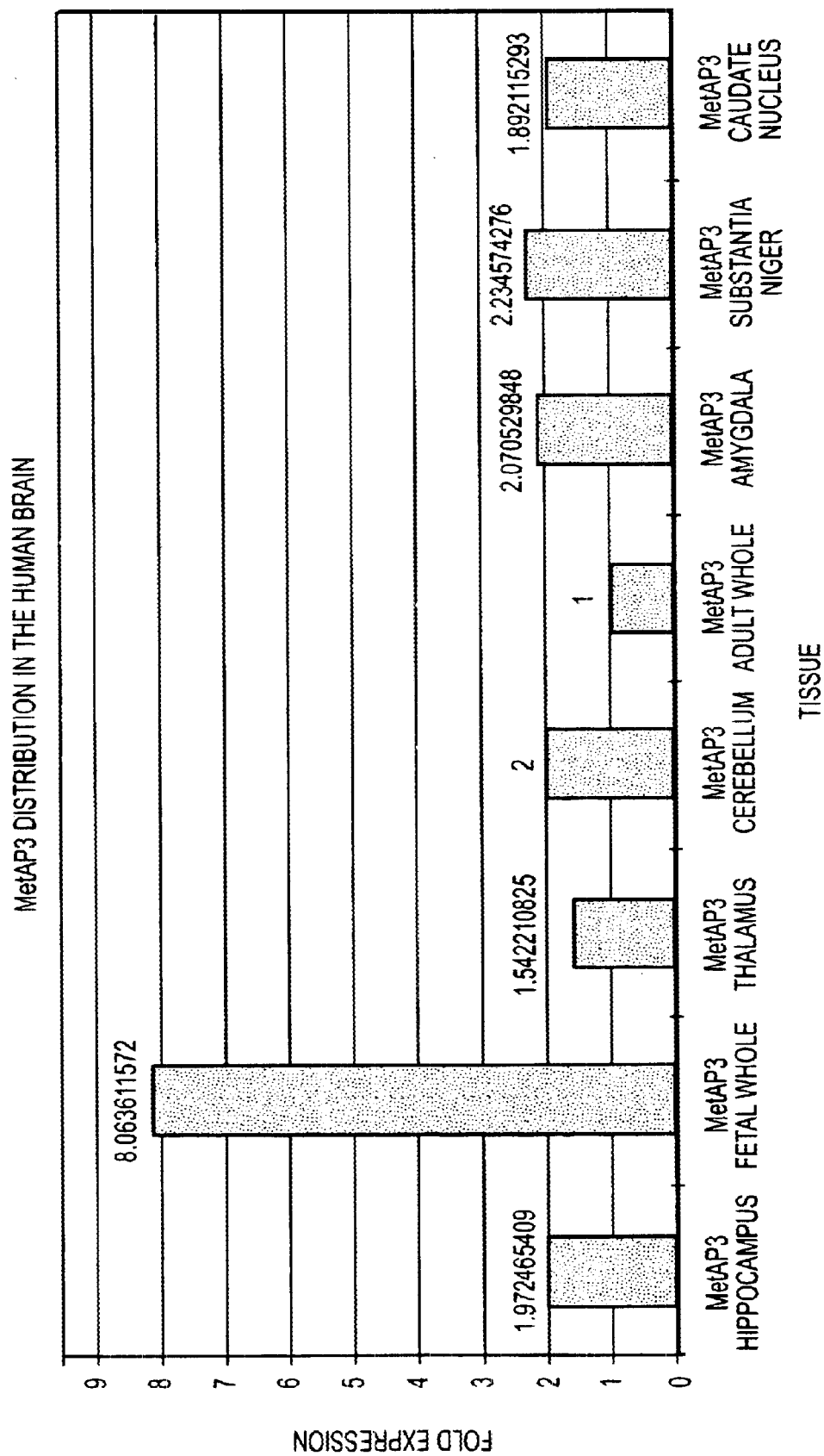
FIG. 16 shows the distribution of MetAP-3 in human brain tissues
Figure 17:
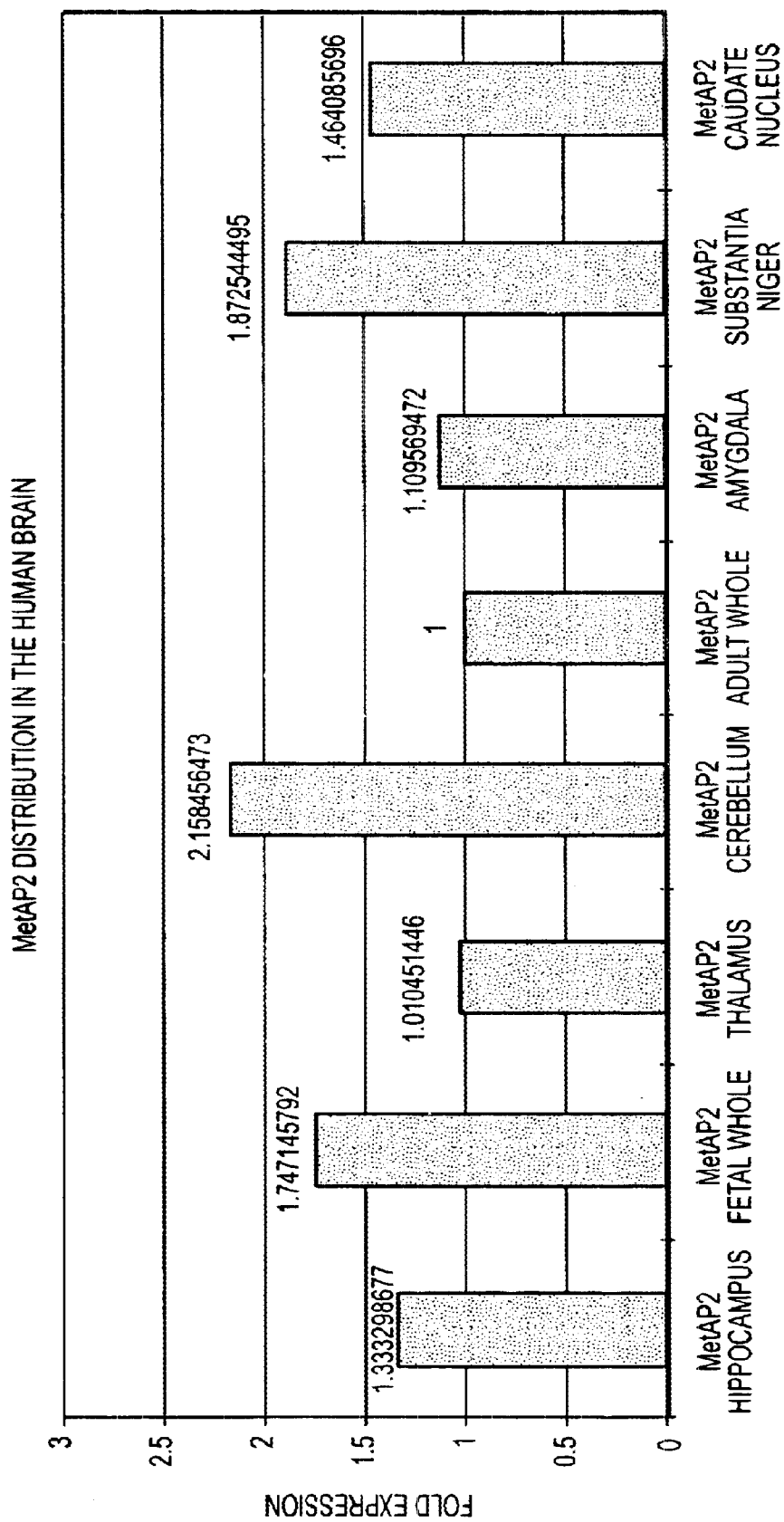
FIG. 17 shows the distribution of MetAP-2 in human brain tissues
Figure 18:
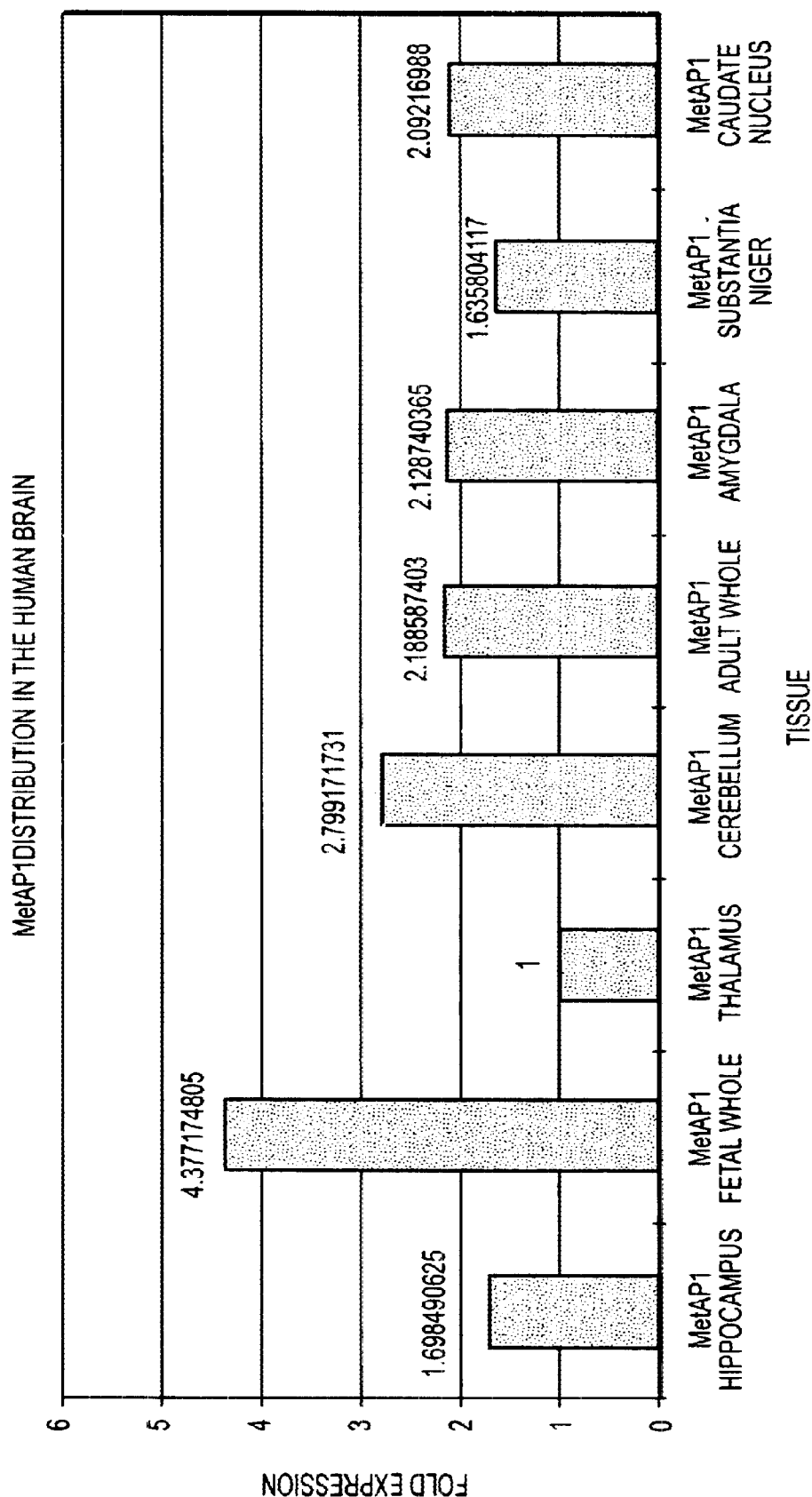
FIG. 18 shows the distribution of MetAP-1 in human brain tissues

As the new protein exhibits a similar primary sequence to MetAP-1 and MetAP-2, it is referred to herein as "MetAP-3." SEQ NO: 8 sets forth the amino acid sequence of human MetAP-3 and SEQ NO: 7 sets forth the nucleic acid sequence encoding of the human MetAP-3 protein. FIG. 2 shows a comparison between the amino acid sequences encoding MetAP-1, MetAP-2, and MetAP-3. FIG. 3 shows the amino acid translation of the full length nucleic acid sequence of MetAP-3.

MetAP-1, MetAP-2 and MetAP-3 exhibit different expression profiles when various tissues were sampled. The expression patterns of MetAP-1, MetAP-2 and MetAP-3 are shown in Examples 2 and 3.

II. Molecules of the Present Invention

The term "angiogenesis" has recognized meaning in the art. The methods of the present invention are particularly relevant in the monitoring of the expression of MetAP-3. The methods of the present invention are also relevant in the monitoring of the expression of MetAP-3 in cancer patients. Molecules of the present invention are capable of being used to diagnose MetAP-3 expression. Molecules of the present invention are also capable of being used to diagnose the level of MetAP-3 expression in cancer patients. Molecules of the present invention can also be used as therapeutic agents and in diagnostic methods.

The molecules of the present invention may be either naturally-occurring or non-naturally occurring. As used herein, a naturally-occurring molecule may be "substantially-pure" or "substantially-purified," if desired, such that one or more molecules that is or may be present in a naturally occurring preparation containing that molecule will have been removed or will be present at a lower concentration than that at which it would normally be found.

The molecules of the present invention will preferably be "biologically active" with respect to either a structural attribute, such as the capacity of a nucleic acid to hybridize to another nucleic acid molecule, or the ability of a protein to be bound by antibody (or to compete with another molecule for such binding). Alternatively, such an attribute may be catalytic, and thus involve the capacity of the agent to mediate a chemical reaction or response.

The molecules of the present invention comprise nucleic acid molecules, proteins, peptides, antibodies, and organic molecules.

A. Nucleic Acid Molecules

A preferred class of agents of the present invention comprise MetAP-3 nucleic acid molecules. Such molecules may be DNA or RNA.

In one embodiment, such nucleic acid molecules will encode all or a fragment of MetAP-3 protein, preferably human MetAP-3. These nucleic acids optionally contain a "promoter" or flanking gene sequences. As used herein, the term "promoter" is used in an expansive sense to refer to the regulatory sequence(s) that control mRNA production. Such sequences include RNA polymerase binding sites, enhancers, etc. All such MetAP-3 molecules may be used in a diagnostic or therapeutic context.

Fragments of MetAP-3 nucleic acid molecules may encode significant portion(s) of, or most of, the MetAP-3 protein. Preferably, a fragment MetAP-3 nucleic acid molecule is identical or complementary to at least about 12 contiguous nucleotides in SEQ NO: 5. More preferably it comprises at least about 25 nucleotides in SEQ NO: 5. Even more preferably it comprises at least about 50 nucleotides in SEQ NO: 5. Most preferably, it comprises at least about 100 nucleotides in SEQ NO: 5. Additionally, MetAP-3 nucleic acid molecules and fragment MetAP-3 nucleic acid molecules can possess about 70% to about 95% sequence identity over a region of 12, or about 50 to about 100 contiguous nucleotides of SEQ NO: 5 or their complements.

In a preferred embodiment, a fragment MetAP-3 nucleic acid molecule comprises at least one nucleotide that is not found in a corresponding position in MetAP-3. In another preferred embodiment, the fragment MetAP-3 protein exhibits MetAP-3 enzymatic activity.

MetAP-3 nucleic acid molecules and fragment MetAP-3 nucleic acid molecules can specifically hybridize with other nucleic acid molecules. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another tinder conventional "high-stringency" conditions. Conventional stringency conditions are described by Sambrook, et al., *Molecular Cloning*, A Laboratory Manual, 2nd Ed., Cold Spring Harbor Press, Cold Spring Harbor, N.Y. (1989), and by Haymes, et al. *Nucleic Acid Hybridization, A Practical Approach*, IRL Press, Washington, D.C., 1985). Departures from complete complementarity are therefore permissible, as long as such departures do not completely preclude the capacity of the molecules to form a double-stranded structure.

Appropriate stringency conditions which promote DNA hybridization are, for example, 6×sodium saline citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a moderately low stringency of about 2×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to a nucleic acid molecule having SEQ NO: 5 or its complement under moderately stringent conditions, for example at about 2×SSC and about 40° C. about 50° C.

In a particularly preferred embodiment, a nucleic acid of the present invention will specifically hybridize to SEQ NO: 5 or its complement under high stringency conditions, such as about 0.2×SSC and about 45° C. to about 65° C. In one aspect of the present invention, a nucleic acid molecule of the present invention will comprise SEQ NO: 5 or its complement.

Fragment nucleic acid molecules can be determined and selected such that, under specified conditions, such as high stringency, they can be used to specifically hybridize to MetAP-3 sequences and not, for example, to MetAP-1 or MetAP-2 sequences. Furthermore, specific sequences that hybridize to MetAP-3 and not to MetAP-1 or MetAP-2 can be deduced from the sequences using algorithms which are known and available in the art.

In another aspect of the present invention, a nucleic acid molecule of the present invention shares between about 100% and about 70% sequence identity with the nucleic acid sequence set forth in SEQ NO: 7 or its complement. In a further aspect of the present invention, a nucleic acid molecule of the present invention shares between about 100% and about 95% sequence identity with the nucleic acid sequence set forth in SEQ NO: 7 or its complement. In a more preferred aspect of the present invention, a nucleic acid molecule of the present invention shares between about 100% and about 98% sequence identity with SEQ NO: 7 or its complement. In the most preferred aspect of the present invention, a nucleic acid molecule of the present invention shares between about 100% and about 99% sequence identity with SEQ NO: 5 or its complement.

Homologues and polymorphic sequences, especially single polymorphic sequences, of the human nucleic acids of SEQ NO: 7 are also provided. A subset of the nucleic acid molecules of the invention includes hybridization or PCR probes which can be used, for example, to identify mammalian MetAP-3 homologue nucleic acids and genes. These probes can also be used to identify genomic clones of MetAP-3, especially human genomic clones, or to identify genomic regions flanking the MetAP-3 gene.

The degeneracy of the genetic code, which allows different nucleic acid sequences to code for the same protein or peptide, is known in the literature. (U.S. Pat. No. 4,757,006). As used herein, a nucleic acid molecule is degenerate of another nucleic acid molecule when the nucleic acid molecules encode for the same amino acid sequences, but comprise different nucleotide sequences. An aspect of the present invention is that the nucleic acid molecules of the present invention include nucleic acid molecules that are degenerate of SEQ NO: 7 and its complement.

Apart from their other uses, such as those described below, the nucleic acid molecules of the present invention can be employed to obtain other MetAP-3 molecules. Nucleic acid molecules and fragments thereof of the present invention may be employed to obtain other nucleic acid molecules from humans. Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules, or fragments thereof, to screen cDNA or genomic libraries obtained from humans or to search databases of sequence information. Methods for forming such libraries and searching databases are well known in the art.

Nucleic acid molecules and fragments thereof of the present invention may also be employed to obtain nucleic acid homologues. Such homologues include the nucleic acid molecule of other organisms (e.g., monkey, mouse, rat, dog, cat) including the nucleic acid molecules that encode, in whole or in part, protein homologues of other species or other organisms, and sequences of genetic elements such as promoters and transcriptional regulatory elements from other species or organisms. Such molecules can be readily obtained by using the above-described nucleic acid molecules or fragments thereof to screen cDNA or genomic libraries obtained from such species. Methods for forming such libraries are well known in the art. Such homologue molecules may differ in their nucleotide sequences from those found SEQ NO: 5 or complement thereof. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci. (U.S.A.)* 83:4143–4146 (1986); Goodchild et al., *Proc. Natl. Acad. Sci. (U.S.A.)* 85:5507–5511 (1988); Wickstrom et al., *Proc. Natl. Acad. Sci. (U.S.A.)* 85:1028–1032 (1988); Holt et al., *Molec. Cell. Biol.* 8:963–973.(1988); Gerwirtz et al., *Science* 242:1303–1306 (1988); Anfossi et al., *Proc. Natl. Acad. Sci. (U.S.A.)* 86:3379–3383 (1989); Becker et al., *EMBO J.* 8:3685–3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263–273 (1986); Erlich et al., European Patent 50,424; European Patent 84,796, European Patent 258,017, European Patent 237,362; Mullis, European Patent 201,184; Mullis et al., U.S. Pat. No. 4,683,202; Erlich, U.S. Pat. No. 4,582,788; and Saiki, R. et al., U.S. Pat. No. 4,683,194) to amplify and obtain any desired nucleic acid molecule or fragment.

The MetAP-3 promoter sequence(s) and MetAP-3 flanking sequences can also be obtained using the SEQ NO: 7 sequence provided herein. In one embodiment, such sequences are obtained by incubating oligonucleotide probes of MetAP-3 oligonucleotides with members of genomic human libraries and recovering clones that hybridize to the probes. In a second embodiment, methods of "chromosome walking," or 3' or 5' RACE may be used (Frohman, M. A. et al., *Proc. Natl. Acad. Sci. (U.S.A.)* 85:8998–9002 (1988); Ohara, O. et al., *Proc. Natl. Acad. Sci. (U.S.A.)* 86:5673–5677 (1989)) to obtain such sequences.

B. Proteins and Peptides

A second class of preferred agents comprises MetAP-3 protein, shorter polypeptides, or peptide fragments, fusion proteins, and analogs. MetAP-3 protein may be produced via chemical synthesis, or more preferably, by expressing MetAP-3-encoding cDNA in a suitable bacterial or eukaryotic host. Most preferably, the subsequence of such cDNA that encodes MetAP-3 may be used for this purpose (SEQ NO: 5). Suitable methods for expression are described by Sambrook et al., (In: *Molecular Cloning, a Laboratory Manual, 2nd Edition*, Cold Spring Harbor Press, Cold Spring Harbor, N.Y. (1989)), or similar texts.

A "MetAP-3 fragment" is a peptide or polypeptide whose amino acid sequence comprises a subset of the amino acid sequence of MetAP-3 protein. Preferably a fragment MetAP-3 molecule is identical or complementary to at least one region which corresponds to a contiguous 10 amino acids of SEQ NO: 8; more preferably, at least one region which corresponds to a contiguous 50 amino acids of SEQ NO: 8; even more preferably, at least one region which responds to a contiguous 100 amino acids of SEQ NO: 8. A MetAP-3 protein or fragment thereof that comprises one or more additional non-MetAP-3 peptide regions or amino acids is a "MetAP-3 fusion" protein. Such molecules may be derivatized to contain carbohydrate or other moieties (such as keyhole limpet hemocyanin, etc.). As in the case of MetAP-3 protein, the fragments and fusions of the present invention are preferably produced via recombinant means.

Additionally, variant MetAP-3 proteins or fragments can be generated by known mutagenesis techniques so that one or more amino acids can be substituted, deleted, or added and the methionine aminopeptidase activity retained. Mutations that avoid or employ conservative substitutions within the known functional region, the C-terminal aminopeptidase domain, the residues that coordinate the cobalt ions, or domains possessing the same position in the amino acid chain as the aminopeptidase domain are preferred. Mutations that avoid changing amino acids at the known methionine aminopeptidase enzymatic active sites are also preferred. Methods to generate banks of mutant proteins, such as molecular evolution or DNA shuffling or the like, can be used. Assays for the methionine aminopeptidase activity that can identify these variant MetAP-3 molecules are also known. Such assays may involve an in vitro peptide substrate analysis (Freitas et al., *Int. J. Biochem.* 17:1285–1291 (1985), Xuo et al., *Mol. Gen. Genet.* 246:247–253 (1995), and Kendall and Bradshaw, *J. Biol. Chem.* 267:20667–10673 (1992)).

The analogs of the MetAP-3 molecules comprise MetAP-3 proteins, fragments or fusions in which non-essential, or non-relevant, amino acid residues have been added, replaced, or deleted. An example of such an analog is the MetAP-3 protein of non-human species, such as primates, mice, rats, dogs, cats, etc. Such analogs can readily be obtained by any of a variety of methods. Most preferably, as indicated above, the disclosed SEQ NO: 5 will be used to define a pair of primers that may be used to isolate the MetAP-3-encoding nucleic acid molecules from any desired species. Such molecules can be expressed to yield MetAP-3 analogs by recombinant means.

C. Antibodies Reactive Against MetAP-3

One aspect of the present invention concerns antibodies, single-chain antigen binding molecules, or other proteins that specifically bind to MetAP-3 protein and its analogs, fusions or fragments. Such antibodies are "anti-MetAP-3 antibodies," and may be used, for example to measure MetAP-3 protein. As used herein, an antibody or peptide is said to "specifically bind" to MetAP-3 if such binding is not competitively inhibited by the presence of non-MetAP-3 molecules.

Nucleic acid molecules that encode all or part of the MetAP-3 protein can be expressed, via recombinant means, to yield MetAP-3 protein or peptides that can in turn be used to elicit antibodies that are capable of binding MetAP-3. Such antibodies may be used in immunodiagnostic assays. Such MetAP-3-encoding molecules, or their fragments may be a "fusion" molecule (i.e. a part of a larger nucleic acid molecule) such that, upon expression, a fusion protein is produced.

The antibodies that specifically bind MetAP-3 proteins and protein fragments may be polyclonal or monoclonal, and may comprise intact immunoglobulins, of antigen binding portions of immunoglobulins (such as (F(ab'), F(ab')$_2$) fragments, or single-chain immunoglobulins generated, for example, via recombinant means. It is understood that practitioners are familiar with the standard resource materials which describe specific conditions and procedures for the construction, manipulation and isolation of antibodies (see, for example, Harlow and Lane, *In Antibodies: A Laboratory Manual*, Cold Spring Harbor Press, Cold Spring Harbor, N.Y. (1988)).

Murine monoclonal antibodies are particularly preferred. BALB/c mice are preferred for this purpose, however, equivalent strains may also be used. The animals are preferably immunized with approximately 25 µg of purified MetAP-3 protein (or fragment thereof) that has been emulsified with a suitable adjuvant (such as TiterMax adjuvant (Vaxcel, Norcross, Ga.)). Immunization is preferably conducted at two intramuscular sites, one intraperitoneal site, and one subcutaneous site at the base of the tail. An additional i.v. injection of approximately 25 µg of antigen is preferably given in normal saline three weeks later. After approximately 11 days following the second injection, the mice may be bled and the blood screened for the presence of anti-MetAP-3 antibodies. Preferably, a direct binding ELISA is employed for this purpose.

Most preferably, the mouse having the highest antibody titer is given a third i.v. injection of approximately 25 µg of MetAP-3 protein or fragment. The splenic leukocytes from this animal may be recovered 3 days later, and are then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthine-aminopterin-thymine) selection for about one week. The resulting clones may then be screened for their capacity to produce monoclonal antibodies ("mAbs") to MetAP-3 protein, preferably by direct ELISA.

In one embodiment, anti-MetAP-3 monoclonal antibodies are isolated using MetAP-3 fusions, or conjugates, as immunogens. Thus, for example, a group of mice can be immunized using a MetAP-3 fusion protein emulsified in Freund's complete adjuvant (approximately 50 µg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding MetAP-3 at 1:5,000 dilution can also be obtained using this method.

In a preferred procedure for obtaining monoclonal antibodies, the spleens of the above-described immunized mice are removed, disrupted, and immune splenocytes are isolated over a Ficoll gradient. The isolated splenocytes are fused, using polyethylene glycol with BALB/c-derived HGPRT (hypoxanthine guanine phosphoribosyl transferase)-deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2–3 weeks. On average, out of every $10^6$ spleen cells subjected to fusion yields a viable hybridoma. A typical spleen yields 5–10×$10^7$ spleen cells.

Hybridoma cells that arise from such incubation are preferably screened for their capacity to produce an immunoglobulin that binds to MetAP-3 protein. An indirect ELISA may be used for this purpose. In brief, the supernatants of hybridomas are incubated in microtiter wells that contain immobilized MetAP-3 protein. After washing, the titer of bound immunoglobulin can be determined using, for example, a goat anti-mouse antibody conjugated to horseradish peroxidase. After additional washing, the amount of immobilized enzyme is determined (for example, through the use of a chromogenic substrate). Such screening is performed as quickly as possible after the identification of the hybridoma in order to ensure that a desired clone is not overgrown by non-secreting neighbors. Preferably, the fusion plates are screened several times since the rates of hybridoma growth vary. In a preferred embodiment, a different antigenic form of MetAP-3 may be used to screen the hybridoma. Thus, for example, the splenocytes may be immunized with one MetAP-3 immunogen, but the resulting hybridomas can be screened using a different MetAP-3 immunogen.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as fluorescent group, a radioisotope or an enzyme).

The ability to produce antibodies that bind MetAP-3 molecules permits the identification of mimetic compounds of MetAP-3. A "mimetic compound" of MetAP-3 is a compound that is not MetAP-3 or a fragment of MetAP-3, but which nonetheless exhibits an ability to specifically bind to anti-MetAP-3 antibodies. Such molecules can be used to elicit anti-MetAP-3 antibodies, and thus, may be used to assist diagnosis of MetAP-3 related disorders.

III. Uses of the Molecules of the Invention

An aspect of the present invention provides plasmid DNA vectors for use in the expression of the MetAP-3 protein. These vectors contain the DNA sequences described above which code for the polypeptides of the invention. Appropriate vectors which can transform eukaroytic cells, including mammalian cells and microorganisms capable of expressing the MetAP-3 protein include expression vectors comprising nucleotide sequences coding for the MetAP-3 protein joined to transcriptional and translational regulatory sequences which are selected according to the host cells used.

Vectors incorporating modified sequences as described above are included in the present invention and are useful in the production of the MetAP-3 polypeptides. The vector employed in the method also contains selected regulatory sequences in operative association with the DNA coding sequences of the invention which are capable of directing the replication and expression thereof in selected host cells.

Transfer of a nucleic acid that encodes for a protein can result in overexpression of that protein in a transformed cell. One or more of the proteins or fragments thereof encoded by nucleic acid molecules of the present invention may be overexpressed in a transformed cell. Particularly, any of the MetAP-3 proteins or fragments thereof may be overexpressed in a transformed cell. Such overexpression may be the result of transient or stable transfer of the exogenous genetic material. "Exogenous genetic material" is any genetic material, whether naturally occurring or otherwise, from any source that is capable of being inserted into any organism.

A construct or vector may include a promoter to express the protein or protein fragment of choice. Some promoters that can be used in the present invention may include the interleukin-1 alpha promoter (Mori and Prager, *Leuk. Lymphoma* 26:421–433 (1997)), CMV promoter (Tong et al., *Anticancer Res.* 18:719–725 (1998); Norman et al., *Vaccine* 15:801–803 (1997)); RSV promoter (Elshami et al., *Cancer Gene Ther.* 4:213–221 (1997); Baldwin et al., *Gene Ther.* 4:1142–1149 (1997)); SV40 promoter (Harms and Splitter, *Hum. Gene Ther.* 6:1291–1297 (1995)), CD11c integrin gene promoter (Corbi and Lopez-Rodriguez, *Leuk. Lymphoma* 25:415–425 (1997),), GM-CSF promoter (Shannon et al., *Crit. Rev. Immunol.* 17:301–323 (1997)), interleukin-5R alpha promoter (Sun et al., *Curr. Top. Microbiol. Immunol* 211:173–187 (1996)), interleukin-2; promoter (Serfing et al., *Biochim. Biophys. Acta* 1263:181–200 (1995); O'Neill et al., *Transplant Proc.* 23:2862–2866 (1991)), c-fos promoter (Janknecht, *Immunobiology* 193:137–142 (1995); Janknecht et al., *Carcinogenesis* 16:443–450 (1995); Takai et al., *Princess Takamatsu Symp.* 22:197–204 (1991)), h-ras promoter (Rachal et al., *EXS* 64:330–342 (1993)), and DMD gene promoter (Ray et al., *Adv. Exp. Med. Biol.* 280:107–111 (1990)).

Promoters suitable for expression of the MetAP-3 protein or fragment thereof of the present invention in bacteria have been described by Hawley and McClure, *Nucleic Acids Res.* 11:2237–2255 (1983), and Harley and Reynolds, *Nucleic Acids Res.* 15:2343–2361 (1987). Such promoters include, for example, the recA promoter (Fernandez de Henestrosa et al., *FEMS Microbiol. Lett.* 147 :209–213 (1997); Nussbaumer et al., *FEMS Microbiol. Lett.* 118 :57–63 (1994); Weisemann et al., *Biochimie* 73: 457–470 (1991)), the Ptac promoter (Hasan et al., *Gene* 56:141–151 (1987); Marsh, *Nucleic Acids Res.* 14:3603 (1986)); and a Ptac-recA hybrid promoter.

It is preferred that the particular promoter selected is capable of causing sufficient expression to result in the production of an effective amount of the MetAP-3 protein or fragment thereof to cause the desired phenotype.

Constructs or vectors may also include with the coding region of interest a nucleic acid sequence that acts, in whole or in part, to terminate transcription of that region.

Translational enhancers may also be incorporated as part of the vector DNA. DNA construct's could contain one or more 5' non-translated leader sequences that may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence.

A vector or construct may also include a screenable marker. Screenable markers may be used to monitor expression. Exemplary screenable markers include β-glucuronidase (GUS) encoded by the uidA/gusA gene (Jefferson, *Plant Mol. Biol. Rep.* 5: 387–405 (1987); Jefferson et al., *EMBO J.* 6: 3901–3907 (1987)); β-lactamase (Sutcliffe et al., *Proc. Natl. Acad. Sci. (U.S.A.)* 75: 3737–3741 (1978)), luciferase (Clontech, Palo Alto, Calif., USA) (Ow et al., *Science* 234: 856–859 (1986)); β-galactosidase (Clontech, Palo Alto, Calif., USA); GST (Stratagene); Protein A (Calbiochem); and blue and green fluorescent proteins and similar proteins (Clontech, Palo Alto, Calif., USA).

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected by catalytic reactions. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell membrane (such as proteins which include a leader sequence). Other possible selectable and/or screenable marker genes are apparent to those of skill in the art.

As another aspect of the present invention, there is provided a method for producing the MetAP-3 protein. Suitable cells or cell lines may be bacterial cells. For example, the various strains of *E. coli* are well-known as host cells in the field of biotechnology. Examples of such strains include *E. coli* strains JM101 (Yanish-Perron et al. *Gene* 33:103–119 (1985)) and MON105 (Obukowicz et al., *Applied Environmental Microbiology* 58:1511–1523 (1992)). Also included in the present invention is the expression of the MetAP-3 protein or fragment thereof utilizing a chromosomal expression vector for *E. coli* based on the bacteriophage Mu (Weinberg et al., *Gene* 126:25–33 (1993)). Various strains of *B. subtilis* may also be employed in this method. Many strains of yeast cells known to those skilled in the art are also available as host cells for expression of the polypeptides of the present invention.

When expressed in the *E. coli* cytoplasm, the gene encoding the MetAP-3 protein or fragment thereof of the present invention may also be constructed such that the 5' end of the gene codons are added to encode $Met^{-2}$-$Ala^{-1}$- or $Met^{-1}$ at the N-terminus of the protein. The N termini of proteins made in the cytoplasm of *E. coli* are affected by post-translational processing by methionine aminopeptidase (Bassat et al., *J. Bacteriol.* 169:751–757 (1987)) and possibly by other peptidases so that upon expression the methionine is cleaved off the N-terminus. The MetAP-3 protein of the present invention may be MetAP-3 polypeptides having $Met^{-1}$, $Ala^{-1}$ or $Met^{-2}$-$Ala^{-1}$ at the N-terminus. Other typically small amino acids may also be substituted for alanine. These MetAP-3 polypeptides may also be expressed in *E. coli* by fusing a secretion signal peptide of the N-terminus. This signal peptide can be cleaved from the polypeptide as part of the secretion process.

Under another embodiment, the MetAP-3 protein or fragment thereof of the present invention is expressed in a yeast cell, preferably *Saccharomyces cerevisiae*. The MetAP-3 protein or fragment thereof of the present invention can be expressed in *S. cerevisiae* by fusing it to the N-terminus of the URA3, CYC1 or ARG3 genes (Guarente and Ptashne, *Proc. Natl. Acad. Sci. (U.S.A.)* 78:2199–2203 (1981); Rose et al., *Proc. Natl. Acad. Sci. (U.S.A.)* 78:2460–2464 (1981); and Crabeel et al., *EMBO J.* 2:205–212 (1983)). Alternatively, the MetAP-3 protein or fragment thereof of the present invention can be fused to either the PGK or TRP1 genes (Tuite et al., *EMBO J.* 1:603–608 (1982); and Dobson et al., *Nucleic Acids. Res.* 11:2287–2302 (1983)). More preferably, the MetAP-3 protein or fragment thereof of the present invention is expressed as a mature protein (Hitzeman et al., *Nature* 293:717–722 (1981); Valenzuela et al., *Nature* 298:347–350 (1982); and Derynck et al., *Nucleic Acids Res.* 11:1819–1837 (1983)).

Native and engineered yeast promoters suitable for use in the present invention have been reviewed by Romanos et al., *Yeast* 8:423–488 (1992). Most preferably, the MetAP-3 protein or fragment thereof of the present invention is secreted by the yeast cell (Blobel and Dobberstein, *J. Cell Biol.* 67 :835–851 (1975); Kurjan and Herskowitz, *Cell* 30:933–943 (1982); Bostian et al., *Cell* 36:741–751 (1984); Rothman and Orci, *Nature* 355:409–415 (1992); Julius et al., *Cell* 32:839–852 (1983); and Julius et al., *Cell* 36:309–318 (1984)).

Where desired, insect cells may be utilized as host cells in the method of the present invention. See, e.g., V. A. Luckow, *Protein Eng.* J. L. Cleland., Wiley-Liss, New York, N.Y.: 183–2180 (1996) and references cited therein. In addition, general methods for expression of foreign genes in insect cells using baculovirus vectors are described in: O'Reilly et al., *Baculovirus Expression Vectors: A Laboratory Manual*. New York, W.H. Freeman and Company (1992), and King and Possee, *The Baculovirus Expression System: A. Laboratory Guide*, London, Chapman & Hall, (1992). An expression vector is constructed comprising a baculovirus transfer vector, in which a strong baculovirus promoter (such as the polyhedrin promoter) drives transcription of a eukaryotic secretion signal peptide coding region, which is translationally joined to the coding region for the MetAP-3 protein. For example, the plasmid pVL1393 (Invitrogen Corp., San Diego, Calif., U.S.A.) can be used. After construction of the vector carrying the gene encoding the MetAP-3 protein, two micrograms of this DNA is co-transfected with one microgram of baculovirus DNA into Spodoptera frugiperda insect cells, strain Sf9. Alternatively, recombinant baculoviruses can be created using a baculovirus "shuttle vector system (Luckow et al., J. Virol. 67: 4566–4579 (1993)), now marketed as the Bac-To-Bac™ Expression System (Life Technologies, Inc. Rockville, Md.). Pure recombinant baculoviruses carrying the MetAP-3 protein is used to infect cells cultured for example, in Excell 401 serum-free medium (JRH Biosciences, Lenexa, Kans.) or Sf900-II (Life Technologies, Inc.). The MetAP-3 protein secreted into the medium can be recovered by standard biochemical approaches. Supernatants from mammalian or insect cells expressing the MetAP-3 proteins can be first concentrated using a variety of commercial concentration units.

Mammalian cells can also be used to express the nucleic acid molecules of the present invention. Preferably, the nucleic acid molecules of the present invention are cloned into a suitable retroviral vector (see, e.g., Dunbar et al., Blood 85 :3048–3057 (1995); Baum et al., J. Hematother. 5: 323–329 (1996); Bregni et al., Blood 80:1418–1422 (1992); Boris-Lawrie and Temin, Curr. Opin. Genet. Dev. 3:102–109 (1993); Boris-Lawrie and Temin, Annal. New York Acad. Sci. 716:59–71 (1994); Miller, Current Top. Microbiol. Immunol. 158:1–24 (1992)), adenovirus vector (Berkner, BioTechniques 6:616–629 (1988); Berkner, Current Top. Microbiol. Immunol. 158:39–66 (1992); Brody and Crystal, Annal. New York Acad. Sci. 716:90–103 (1994); Baldwin et al., Gene Ther. 4:1142–1149 (1997)), RSV, MuSV, SSV, MuLV (Baum et al., J. Hematother. 5: 323–329 (1996)), AAV (Chen et al., Gene Ther. 5:50–58 (1998); Hallek et al., Cytokines Mol. Ther. 2: 69–79 (1996)), AEV, AMV, or CMV (Griffiths et al., Biochem. J. 241: 313–324 (1987)).

Alternatively, direct peptide synthesis can be achieved using solid-phase techniques (In: Solid Phase Peptide Synthesis, WH Freeman Co., San Francisco, Calif., Stewart et al. Eds. (1969), Merrifield, J. Am Chem. Soc. 85:2149–2154 (1963)). Automated synthesis may be achieved, for example, using 421A Peptide Synthesizer (Applied Biosystems/Perkin Elmer, Foster City, Calif.) in accordance with the instructions provided by the manufacturer. Chemical protein synthesis can also be an effective way of obtaining functional proteins directly from sequence data. One such approach is chemical ligation, a chemoselective reaction of unprotected peptide segments (Wilken and Kent, Curr. Opin. Biotechnol. 9:412–426 (1998)).

In another aspect, the invention provides a transformed cell having a nucleic acid molecule which comprises an exogenous promoter region which functions in a cell to cause the production of an mRNA molecule which is linked to a structural nucleic acid molecule, wherein the structural nucleic acid molecule encodes a MetAP-3 gene or fragment thereof. This nucleic acid molecule is linked to a 3' non-translated sequence that functions in a cell to cause termination of transcription and addition of polyadenylated ribonucleotides to a 3' end of the mRNA molecule.

Methods and compositions for transforming a eukaryotic cell, bacteria and other microorganisms are known in the art (see, for example, Sambrook et al., Molecular Cloning: A Laboratory Manual, Second Edition, Cold Spring Harbor Laboratory Press, Cold Spring Harbor, N.Y., (1989)).

Technology for introduction of DNA into cells is well known to those of skill in the art. Four general methods for delivering a gene into cells have been described: (1) chemical methods (Graham and van der Eb, Virology 54:536–539 (1973)); (2) physical methods such as microinjection (Capecchi, Cell 22:479–488 (1980)), electroporation (Wong and Neumann, Biochem. Biophys. Res. Commun. 107:584–587 (1982); Fromm et al., Proc. Natl. Acad. Sci. (U.S.A.) 82 :5824–5828 (1985); U.S. Pat. No. 5,384,253); and the gene gun (Johnston and Tang, Methods Cell Biol. 43:353–365 (1994); (3) viral vectors (Clapp, Clin. Perinatol. 20:155–168 (1993); Lu et al., J. Exp. Med. 178 :2089–2096 (1993); Eglitis and Anderson, Biotechniques, 6:608–614 (1988)); and (4) receptor-mediated mechanisms (Curiel et al., Hum. Gen. Ther. 3:147–154 (1992), Wagner et al., Proc. Natl. Acad. Sci. (U.S.A.) 89:6099–6103 (1992)). Other methods well known in the art can also be used.

Transformation can be achieved using methods based on calcium phosphate precipitation, polyethylene glycol treatment, electroporation, and combinations of these treatments (see for example Potrykus et al., Mol. Gen. Genet. 205:193–200 (1986); Lorz et al., Mol. Gen. Genet. 199:178 (1985); Fromm et al., Nature 319:791 (1986); Uchimiya et al., Mol. Gen. Genet. 204:204 (1986); Marcotte et al., Nature 335:454–457 (1988)).

Assays for gene expression based on the transient expression of cloned nucleic acid constructs have been developed by introducing the nucleic acid molecules into cells by polyethylene glycol treatment, electroporation, or particle bombardment (Marcotte et al., Nature 335: 454–457 (1988); McCarty et al., Cell 66: 895–905 (1991); Hattori et al., Genes Dev. 6: 609–618 (1992); Goffet al., EMBO J. 9: 2517–2522 (1990)). Transient expression systems may be used to functionally dissect gene constructs.

In one embodiment, the MetAP-3 molecules of the present invention are used to determine whether an individual has a mutation affecting the level (i.e., the concentration of MetAP-3 mRNA or protein in a sample, etc.) or pattern (i.e., the kinetics of expression, rate of decomposition, stability profile, etc.) of the MetAP-3 expression (collectively, the "MetAP-3 response" of a cell or bodily fluid) (for example, a mutation in the MetAP-3 gene, or in a regulatory region(s) or other gene(s) that control or affect the expression of MetAP-3), and being predictive of individuals who would be predisposed to, for example tumor angiogenesis, and other disorders. As used herein, the MetAP-3 response manifested by a cell or bodily fluid is said to be "altered" if it differs from the MetAP-3 response of cells or of bodily fluids of normal individuals. Such alteration may be manifested by either abnormally increased or abnormally diminished MetAP-3 response. To determine whether a MetAP-3 response is altered, the MetAP-3 response manifested by the cell or bodily fluid of the patient is compared with that of a similar cell sample (or bodily fluid sample) of normal individuals. As will be appreciated, it is not necessary to re-determine the MetAP-3 response of the cell sample (or bodily fluid sample) of normal individuals each time such a comparison is made; rather, the MetAP-3 response of a particular individual may be compared with previously obtained values of normal individuals.

In one sub-embodiment, such an analysis is conducted by determining the presence and/or identity of polymorphism (s) in the MetAP-3 gene or its flanking regions which are associated with a disorder.

Any of a variety of molecules can be used to identify such polymorphism(s). In one embodiment, the MetAP-3 cDNA sequence (or a sub-sequence thereof) may be employed as a marker nucleic acid molecule to identify such polymorphism (s). Alternatively, such polymorphisms can be detected through the use of a marker nucleic acid molecule or a marker protein that is genetically linked to (i.e., a polynucleotide that co-segregates with) such polymorphism(s). In a preferred aspect of this embodiment, such marker nucleic acid molecules will have the nucleotide sequence of a polynucleotide that is closely genetically linked to such polymorphism(s). Polynucleotide markers that map to such locations are well known and can be employed to identify such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 Mb of the polymorphism(s), and more preferably within 100 kb of the polymorphism(s), and most preferably within 10 kb of the polymorphism(s) can be employed.

The genomes of animals and plants naturally undergo spontaneous mutation in the course of their continuing evolution (Gusella, *Ann. Reu. Biochem.* 55:831–854 (1986)).

A "polymorphism" in the MetAP-3 gene or its flanking regions is a variation or difference in the sequence of the MetAP-3 gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e. the original "allele") whereas other members may have the variant sequence (i.e. the variant "allele"). In the simplest case, only one variant sequence may exist, and the polymorphism is thus said to be di-allelic. In other cases, the species' population may contain multiple alleles, and the polymorphism is termed tri-allelic, etc. A single gene may have multiple different unrelated polymorphisms. For example, it may have a di-allelic polymorphism at one site, and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity and paternity analysis (Weber, U.S. Pat. No. 5,075,217; Armour, et al., *FEBS Lett.* 307:113–115 (1992); Jones, et al., *Eur. J. Haematol.* 39:144–147 (1987); Horn, et al., PCT Application WO 91/14003; Jeffreys, European Patent Application 370,719; Jeffreys, U.S. Pat. No. 5,175,082); Jeffreys. et al., *Amer. J. Hum. Genet.* 39:11–24 (1986); Jeffreys. et al., *Nature* 316:76–79 (1985); Gray, et al., *Proc. R. Acad. Soc. Lond.* 243:241–253 (1991); Moore, et al., *Genomics* 10:654–660 (1991); Jeffreys, et al., *Anim. Genet.* 18:1–15 (1987); Hillel, et al., *Anim. Genet.* 20:145–155 (1989); Hillel, et al., *Genet.* 124:783–789 (1990)).

The detection of polymorphic sites in a sample of DNA may be facilitated through the use of nucleic acid amplification methods. Such methods specifically increase the concentration of polynucleotides that span the polymorphic site, or include that site and sequences located either distally or proximally to it. Such amplified molecules can be readily detected by gel electrophoresis or other means.

The most preferred method of achieving such amplification employs the polymerase chain reaction ("PCR") (Mullis, et al., *Cold Spring Harbor Symp. Quant. Biol.* 51:263–273 (1986); Erlich et al., European Patent Appln. 50,424; European Patent Appln. 84,796, European Patent Application 258,017, European Patent Appln. 237,362; Mullis, European Patent Appln. 201,184; Mullis et al., U.S. Pat. No. 4,683,202; Erlich, U.S. Pat. No. 4,582,788; and Saiki, et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci. (U.S.A.)* 88:189–193 (1991). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

The "Oligonucleotide Ligation Assay" ("OLA") may alternatively be employed (Landegren, et al., *Science* 241: 1077–1080 (1988)). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al. have described a nucleic acid detection assay that combines attributes of PCR and OLA (Nickerson et al., *Proc. Natl. Acad. Sci. (U.S.A.)* 87:8923–8927 (1990). In this method, PCR is used to achieve the exponential amplification of target DNA, which is then detected using OLA. In addition to requiring multiple, and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu et al., *Genomics* 4:560 (1989)), and may be readily adapted to the purposes of the present invention.

Other known nucleic acid amplification procedures, such as allele-specific oligomers, branched, DNA technology, transcription-based amplification systems, or isothermal amplification methods may also be used to amplify and analyze such polymorphisms (Malek et al., U.S. Pat. No. 5,130,238; Davey et at., European Patent Application 329, 822; Schuster et al., U.S. Pat. No. 5,169,766; Miller et al., PCT appln. WO 89/06700; Kwoh et al., *Proc. Natl. Acad. Sci. (U.S.A.)* 86:1173 (1989); Gingeras et al., PCT application WO 88/10315; Walker et al., *Proc. Natl. Acad. Sci. (U.S.A.)* 89:392–396 (1992)). All the foregoing nucleic acid amplification methods could be used.

The identification of a polymorphism in the MetAP-3 gene can be determined in a variety of ways. By correlating the presence or absence of tumor angiogenesis in an individual with the presence or absence of a polymorphism in the MetAP-3 gene or its flanking regions, it is possible to diagnose the predisposition of an asymptomatic patient to tumor angiogenesis or other diseases. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and animal genetic analyses (Glassberg, UK Patent Application 2135774; Skolnick, M. H. et al., *Cytogen. Cell Genet.* 32:58–67 (1982); Botstein, et al., *Ann. J. Hum. Genet.* 32:314–331 (1980); Fischer, et al. (PCT Application WO 90/13668); Uhlen, PCT Application WO 90/11369).

In accordance with this embodiment of the invention, a sample DNA is obtained from a patient's cells. In a preferred embodiment, the DNA sample is obtained from the patient's blood. However, any source of DNA may be used. The DNA is subjected to restriction endonuclease digestion. MetAP-3 is used as a probe in accordance with the above-described RFLP methods.

The polymorphism obtained in this approach can then be cloned to identify the mutation at the coding region which alters the protein's structure, or at the regulatory region of the gene which affects its expression level. Changes involving promoter interactions with other regulatory proteins can be identified by, for example, gel shift.

Several different classes of polymorphisms may be identified through such methods. Examples of such classes include: (1) polymorphisms present in the MetAP-3 cDNA of different individuals; (2) polymorphisms in non-translated MetAP-3 gene sequences, including the promoter or other regulatory regions of the MetAP-3 gene; (3) polymorphisms in genes whose products interact with MetAP-3 regulatory sequences; (4) polymorphisms in gene sequences whose products interact with the MetAP-3 protein, or to which the MetAP-3 protein binds.

In an alternate sub-embodiment, the evaluation is conducted using oligonucleotide "probes" whose sequence is complementary to that, of a portion of MetAP-3 mRNA. Such molecules are then incubated with cell extracts of a patient under conditions sufficient to permit nucleic acid hybridization. For this sub-embodiment, cells of the trabecular meshworks are preferred. The detection of double-stranded probe-mRNA hybrid molecules is indicative of the presence of MetAP-3 mRNA; the amount of such hybrid formed is proportional to the amount of MetAP-3 mRNA. Thus, such probes may be used to ascertain the level and extent of MetAP-3 mRNA production in a patient's cells. Such nucleic acid hybridization may be conducted under quantitative conditions (thereby providing a numerical value of the amount of MetAP-3 mRNA present). Alternatively, the assay may be conducted as a qualitative assay that indicates either that MetAP-3 mRNA is present, or that its level exceeds a user set, predefined value.

In a second embodiment, the previously described "anti-MetAP-3 antibodies" are employed in an immunodiagnostic assay.

In one sub-embodiment of this aspect of the present invention, one can ascertain the MetAP-3 Response in a biopsy (or a macrophage or other blood cell sample), or other cell sample, or more preferably, in a sample of bodily fluid (especially, blood, serum, plasma, tears, etc.).

The anti-MetAP-3 antibodies of the present invention may thus be used in an immunoassay to assess the presence of MetAP-3. Any of a wide array of immunoassays formats may be used for this purpose (Fackrell, *Clin. Immunoassay* 8:213–219 (1985)), Yolken, *Rev. Infect. Dis.* 4:35 (1982); Collins, In: *Alternative Immunoassays*, John Wiley & Sons, N.Y. (1985); Ngo, et al., In: *Enzyme Mediated Immunoassay*, Plenum Press, N.Y. (1985)).

The simplest immunoassay involves merely incubating an antibody that is capable of binding to a predetermined target molecule with a sample suspected to contain the target molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected of containing the target molecule. Target molecules that have become bound to the immobilized antibody can be detected in any of a variety of ways. For example, the support can be incubated in the presence of a labeled, second antibody that is capable of binding to a second epitope of the target molecule. Immobilization of the labeled antibody on the support thus requires the presence of the target, and is proportional to the concentration of the target in the sample. In an alternative assay, the target is incubated with the sample and with a known amount of labeled target. The presence of target molecule in the sample competes with the labeled target molecules for antibody binding sites. Thus, the amount of labeled target molecules that are able to bind the antibody is inversely proportional to the concentration of target molecule in the sample.

In general, immunoassay formats employ either radioactive labels ("RIAs") or enzyme labels ("ELISAs"). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology*, by Work, et al., North Holland Publishing Company, N.Y. (1978), with particular reference to the chapter entitled "An Introduction to Radioimmune Assay and Related Techniques" by Chard. ELISAs have the advantage that they can be conducted using inexpensive equipment, and with a myriad of different enzymes, such that a large number of detection strategies—colorimetric, pH, gas evolution, etc.—can be used to quantitate the assay.

In addition, the enzyme reagents have relatively long shelf-lives, and lack the risk of radiation contamination that attends to RIA use. ELISAS are described in *ELISA and Other Solid Phase Immunoassays* (Kemeny, et al., Eds.), John Wiley & Sons, N.Y. (1988).

Anti- MetAP-3 antibodies or MetAP-3 binding molecules may be administered to a patient, and their capacity to bind to MetAP-3 in vivo may be determined by ocular examination. Significantly, since such a diagnostic test is relatively rapid, immune responses that require significant time, such as the potential eliciting of anti-[anti-MetAP-3] antibodies, or the complexing of such antibodies with anti-MetAP-3 antibodies, is not important. In a preferred embodiment, the antibody will be fluorescently labeled, and will be provided to a patient by injection into the patient's circulatory system.

In another aspect of the present invention, a MetAP-3 protein or fragment thereof can be used in assays for screening test substances for the ability to modulate or maintain MetAP-3 activity. For example, a specific inhibitor of MetAP-3 can be identified using an assay comprising a MetAP-3 protein, fragment, fusion protein, or a cell containing a MetAP-3 protein, fragment, or fusion protein, adding a test compound or composition, and comparing MetAP-1 and MetAP-2 activity to a control. By comparing the effect of a compound or composition on both a MetAP-3 protein and other methionine aminopeptidase proteins, one can identify compounds that specifically effect MetAP-3, or preferentially effect MetAP-3. Thus, specific MetAP-3 inhibitors can be identified using these methods. Conversely, compounds or compositions that specifically or preferentially effect either MetAP-1, MetAP-2, or both can be identified. In similar ways, assays for compounds and compositions that promote, reduce, irreversibly inhibit, or reversibly inhibit methionine aminopeptidase activity in a MetAP-3 protein, fragment, or fusion protein can be screened for. In a sub-embodiment, the test substance is an agonist, antagonist, or small molecule inhibitor of the MetAP-3 protein. In another sub-embodiment, the test substance may bind to MetAP-3 substrate. The test substance may also be an agonist, antagonist, or small molecule inhibitor of MetAP-1 or MetAP-2.

Assays for screening MetAP-3 activity comprise incubating the enzyme with an amount of peptide substrate, stopping the reaction, and quantifying the amount of released methionine. One such assay uses precolumn derivatization and high performance liquid chromatography to measure protease activity (Zuo et al., *Analytical Biochem.* 222:514–516 (1994)).

In another embodiment, the present invention provides a method of using a MetAP-3 protein or fragment thereof in an assay for screening test substances for the ability to modulate or maintain MetAP-3 activity comprising contacting the MetAP enzyme to a peptide substrate, incubating this reaction, then stopping the reaction and determining the amount of released methionine. This assay would be repeated for the other MetAP isozymes to compare activities.

Compositions which modulate or maintain MetAP-3 activity can be tested using cellular assays, such as endothelial cell assays (Rhim et al., *Carcinogenesis* 19:673–81 (1998); Zimrin et al., *Biochem. Biophys. Res. Commun.* 213:630–8 (1995); Madri and Pratt, *J. Histochem. Cytochem.* 34:85–91 (1986)); the chick chorioallantoic membrane assay (CAM) (Ribatti et al., *Int. J. Dev. Biol.* 40:1189–97 (1996); Ribatti et al., *J. Vasc. Res.* 34:455–63 (1997)); or in assays using tumor or other tissues (Montesano et al., *Cell. Biol. Int. Rep.* 9:869–75 (1985); Moore et al., *Microvasc. Res.* 56:145–53 (1998)). Animal models of angiogenesis also can be used to evaluate such compositions, including the mouse tumor-induced angiogenesis model (Robertson et al., *Cancer Res.* 51:1339–44 (1991), Carmeliet et al., *Cardiovasc. Res.* 39:8–33 (1998)); the rabbit corneal micropocket model (Ryu and Albert, *Invest Ophthalmol Vis. Sci.* 18:831–41 (1979)); and the rat subcutaneous air sac model (SAS) (Lichtenberg et al., *Pharmacol. Toxicol.* 84:43–40 (1999)). Further, models utilizing human tumor xenografts, such as a variety of tumors xenografted into SCID, nu/nu, or Balb/c mice (Rofstad, *Br. J. Cancer* 70:804–12 (1995); Rofstad, *Mol. Med. Today* 2:394–403 (1996); Lichtenbeld et al., *Int. J. Cancer* 77:455–9 (1998); and Marvin et al., *Eur. J. Pediatr. Surg.* 8:295–8 (1998); Pot-Deprun and Chouroulinkov, C R *Acad Sci Hebd Seances Acad Sci* 280:685–8 (1975)); the Leydig (testicular) tumor implant in rat (Carron et al., *Cancer Res.* 58(9):1930–5 (1998)) can be used to evaluate a compound's ability to modulate or maintain MetAP-3 activity.

IV. Pharmaceutical Compositions

The agents of the present invention can be formulated according to known methods to prepare pharmacologically acceptable compositions, whereby these materials, or their functional derivatives, having the desired degree of purity, are combined in admixture with a physiologically acceptable carrier, excipient, or stabilizer. Such materials are non-toxic to recipients at the dosages and concentrations employed. The active component of such compositions may MetAP-3 protein, MetAP-3 fusion proteins or fragments of MetAP-3 protein or analogs or mimetics of such molecules. Where nucleic acid molecules are employed, such molecules may be sense, antisense or triplex oligonucleotides of the MetAP-3 cDNA or gene.

A composition is said to be "pharmacologically acceptable" if its administration can be tolerated by a recipient patient. An agent is physiologically significant if its presence results in a detectable change in the physiology of a recipient patient.

Suitable vehicles and their formulation, inclusive of other human proteins, e.g., human serum albumin, are described, for example, in Remington's Pharmaceutical Sciences (16th ed., Osol, Ed., Mack, Easton, Pa. (1980).

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween, Pluronics, or PEG, e.g., Tween 80, in an amount of, for example, 0.04–0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinyl pyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the MetAP-3 molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine sulfate) and the concentration of macromolecules as well as the methods of incorporation in order to control release.

Sustained release formulations may also be prepared, and include the formation of microcapsular particles and implantable articles. For preparing sustained-release compositions, the MetAP-3 molecule(s) of the composition is preferably incorporated into a biodegradable matrix or microcapsule. A suitable material for this purpose is a polylactide, although other polymers of poly-(a-hydroxycarboxylic acids), such as poly-D-(-)-3-hydroxybutyric acid (EP 133,988A), can be used. Other biodegradable polymers include poly(lactones), poly (orthoesters), polyamino acids, hydrogels, or poly (orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Patent No. 1176565, Sidman, U. et al., *Biopolymers* 22:547 (1983), and Langer, R. et al., *Chem. Tech.* 12:98 (1982).

Alternatively, instead of incorporating the MetAP-3 molecule(s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

In an alternative embodiment, liposome formulations and methods that permit intracellular uptake of the molecule will be employed. Suitable methods are known in the art; see, for example, Chicz, et al. PCT Application WO 94/04557, Jaysena, et al. (PCT Application WO 93/12234, Yarosh, U.S. Pat. No. 5,190,762, Callahan, et al. U.S. Pat. No. 5,270,052 and Gonzalezro, PCT Application WO 91/05771.

The pharmaceutical compositions of the present invention may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the molecules.

Having now generally described the invention, the same will be more readily understood through reference to the following examples which are provided by way of illustration, and are not intended to be limiting of the present invention, unless specified.

DETAILED DESCRIPTION OF THE INVENTION

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

General Methods

General methods of cloning, expressing, and characterizing proteins are found in T. Maniatis, et al., *Molecular Cloning, A Laboratory Manual*, Cold Spring Harbor Laboratory, 1982, and references cited therein, incorporated herein by reference; and in J. Sambrook, et al., *Molecular Cloning, A Laboratory Manual*, $2^{nd}$ edition, Cold Spring Harbor Laboratory, 1989, and references cited therein, incorporated herein by reference. General and specific conditions and procedures for the construction, manipulation and isolation of antibodies are well known in the art (see, for example, Harlow and Lane, *In Antibodies: A Laboratory Manual*, Cold Spring Harbor Press, Cold Spring Harbor, N.Y. (1988)).

Unless noted otherwise, all specialty chemicals were obtained from Sigma, Co. (St. Louis, Mo.). Restriction endonucleases and T4 DNA ligase were obtained from Life Technologies, Inc. (Rockville, Md.), New England Biolabs (Beverly, Mass.) or Boehringer Mannheim (Indianapolis, Ind.) or Promega (Madison, Wis.).

Transformation of E. coli Strains

*E. coli* strains such as DH5 alpha and DH10B (Life Technologies, Rockville, Md.), and TG1 (Amersham Corp., Arlington Heights, Ill.) are routinely used for transformation of ligation reactions and are the hosts used to prepare plasmid DNA for transfecting mammalian cells. *E. coli* strains, such as JM101 (Yanisch-Perron et al., *Gene*, 33: 103–119, 1985) and MON105 (Obukowicz, et al., *Appl. and Envir. Micr.*, 58: 1511–1523., 1992) can be used for expressing the proteins of the present invention in the cytoplasm or periplasmic space.

DH10B and DH5alpha subcloning efficiency cells are purchased as competent cells and are ready for transformation using the manufacturer's protocol. Other *E. coli* strains are rendered competent to take up DNA using a $CaCl_2$ method. Typically, 20 to 50 mL of cells are grown in LB medium (1% Bacto-tryptone, 0.5% Bacto-yeast extract, 150 mM NaCl) to a density of approximately 1.0 absorbance unit at 600 nanometers (OD600) as measured by a Baush & Lomb Spectronic spectrophotometer (Rochester, N.Y.). The cells are collected by centrifugation and resuspended in one-fifth culture volume of $CaCl_2$ solution [50 mM $CaCl_2$, 10 mM Tris-Cl ((10 mM 2-amino-2-(hydroxymethyl) 1,3-propanediol hydrochloride, pH7.4] and are held at 4° C. for 30 minutes. The cells are again collected by centrifugation and resuspended in one-tenth culture volume of $CaCl_2$ solution. Ligated DNA is added to 0.2 mL of these cells, and the samples are held at 4° C. for 30–60 minutes. The samples are shifted to 42° C. for two minutes and 1.0 mL of LB is added prior to shaking the samples at 37° C. for one hour. Cells from these samples are spread on plates (LB medium plus 1.5% Bacto-agar) containing either ampicillin (100 micrograms/mL, ug/mL) when selecting for ampicillinresistant transformants, or spectinomycin. (75 ug/mL) when selecting for spectinomycin-resistant transformants. The plates are incubated overnight at 37° C.

Colonies are picked and inoculated into LB plus appropriate antibiotic (100 ug/mL ampicillin or 75 ug/mL spectinomycin) and are grown at 37° C. while shaking.

DNA Isolation and Characterization

Plasmid DNA can be isolated by a number of different methods and using commercially available kits known to those skilled in the art. Plasmid DNA is isolated using the Promega Wizard™ Miniprep kit (Madison, Wis.), the Qiagen QIAwell Plasmid isolation kits (Chatsworth, Calif.) or Qiagen Plasmid Midi or Mini kit. These kits follow the same general procedure for plasmid DNA isolation. Briefly, cells are pelleted by centrifugation (5000×g), the plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted. After screening for the colonies with the plasmid of interest, the E. coli cells are inoculated into 50–100 ml of LB plus appropriate antibiotic for overnight growth at 37° C. in an air incubator while shaking. The purified plasmid DNA is used for DNA sequencing, further restriction enzyme digestion, additional subcloning of DNA fragments and transfection into E. coli, mammalian cells, or other cell types.

DNA Sequencing Protocol

DNA samples were prepared containing 500 ng of template DNA and 100 ng of primer of choice in thin-walled 0.2 mL PCR tubes that have been brought to 12 uL with Millipore milli-Q (mQ)-quality water. 2 uL of 2 mM Mg.$^{++}$ was added to each tube. Tubes were denatured for 5 minutes at 96 degrees in a Perkin-Elmer System 9700 thermal cycler. After denaturation, the tubes were chilled to a temperature of 4 degrees Celsius by the thermal cycler. 6 uL of ABI Prism Big Dye Terminator Cycle Sequencing Ready Reaction Kit was added to each tube. The samples were returned to the thermal cycler and cycle-sequenced using the following program: (1) 96° C. for 30 (2) 50° C. for 5 sec; (3) 60° C. for 4 min, followed by step (1) for 24 additional cycles and then held at 4° C. Cycle sequencing was complete after about 2.5 hours. Samples were purified through a Millipore MAHV N45 50 Multiscreen-HV filtration plate which had been filled with 25 uL Sephadex G-50 superfine resin and 300 uL mQ water. Before loading samples onto filtration plates, the plate was prespun in a centrifuge at 750×G for 2 min to remove excess water. The samples were loaded onto the resin and the plate spun again at 750×G for 4 min. The purified sample was collected into a 96-well plate that was placed directly underneath the Sephadex-filled plate during the spin. The liquid in the 96-well plate was dried at room temperature in a Speed Vac. After 45–60 min the DNA was dried and pelleted at the bottom of the plate. Samples were resuspended in 3 uL of a formamide/blue Dextran loading dye and were heated for 2 minutes (see p.33 of Perkin-Elmer Big Dye manual for loading buffer recipe). Samples were loaded onto a 48 cm well-to-read length 4.5% acrylamide gel and were sequenced for 7 hr using run module Seq Run 48E-1200 and dye set DT (BD Set Any-Primer). The Perkin-Elmer Data Collection and Sequence Analysis programs assign bases to the data collected.

EXAMPLE 1

Cloning of a Partial cDNA Encoding MetAP3

Methionine aminopeptidase type 3, MetAP3, was originally discovered as a partial clone in the Incyte database, ID 2937276. The Incyte clone was sequenced and used to design oligonucleotide primers. These primers were used in PCR reactions with template cDNA from various tissues (brain, heart, muscle, and Baby Hamster Kidney HS-5). HS-5 cDNA gave the best signal.

The forward (sense strand) oligonucleotide, MAP3-For1 (SEQ ID NO: 23) was biotinylated and used as a probe to enrich the DNA population for the MetAP3 gene by the GeneTrapper protocol. An apparent full length clone (full length coding region) was isolated from a HS5 library, designated MetAP3-GT9D, 3106bp. Upon further analysis it appeared that the original clone possibly contained an incomplete coding region.

The Incyte database was searched for new MetAP3 clones with more upstream sequence. Incyte clone 2480296 was discovered which aligned with the original MetAP3-GT9D clone, but revealed the presence of a 50 basepair insert in the MetAP3-GT9D clone. With the insert removed, a larger open reading frame, (ORF), in frame with the original ORF, was observed. The Incyte clone, 2480296, was missing the AT of the apparent ATG start codon present in the MetAP3-GT9D clone.

EXAMPLE 2

Cloning of a Full-length cDNA Clone Encoding MetAP3

GeneTrapper was performed again using a brain cDNA library and the biotinylated MAP3-For1 oligonucleotide (SEQ ID NO: 23). A new MetAP3 clone was isolated, MetAP3-HZ2 which did not possess the 50 bp insert, but was also missing the entire ATG start codon. This new clone is also lacking some of the untranslated 3' sequence. It has been fully sequenced at 1532 bp. Oligonucleotides were designed to amplify just the coding region of this new MetAP3. The oligonucleotides, designated MAP3 FOR+ADAPT+ATG (SEQ ID NO: 24) and MAP3 REV-NotI (SEQ ID NO: 25), were used to incorporate restriction sites and also to rebuild the ATG. The MetAP3 coding region, 1008 bp, was amplified by polymerase chain reaction. The DNA of MetAP3-HZ2 served as template for the PCR reaction. The resulting product was verified to be the correct size by visualization on a 1% agarose, 1×TAE gel. The PCR product was trimmed by restriction enzyme digestion with EcoRI and NotI and gel-purified. The vectors pFASTBAC-1 and pFASTBAC-HTa (Life Technologies, Inc., Rockville, Md.) were prepared for ligation by restriction enzyme digestion with EcoRI and NotI and gel purification of the resulting linearized vector. pFASTBAC-1 and pFASTBAC-HTa were individually ligated with the prepared coding region of MetAP3-HZ2. The HT series of vectors encode histidine tags that facilitate of fusion proteins on nickel columns. E. coli strain DH10B was transformed with the ligation product. Resulting colonies were screened by restriction enzyme analysis, EcoRI—NotI, for constructs containing the correct insert size, 1008 bp. Positives, by size screening, were analyzed by sequence analysis at their 5' and 3' ends using vector-specific T7 and SP6 oligonucleotide primers which flank the insert site. Inserts with correct flanking sequences were fully sequenced using gene-specific oligonucleotides. A summary of the oligonucleotides used and the plasmids constructed are shown below.

MAP3-For1: TGGACGAATGTGGTAAAAAG (SEQ ID NO: 23)

MAP3 FOR+ADAPT+ATG: CTAGAATTCATGGCG-GCGCCCAGTGGCGTC (SEQ ID NO: 24)

MAP3 REV-NotI: TGCGGCCGCTCAGGCCT-CATGGGGTAG (SEQ ID NO: 25)

MAP3 FOR2: ACAATCAGCCACATAAC (SEQ ID NO: 26)

MAP3 FOR3: TTCTCTTCACCACTCAATC (SEQ ID NO: 27)

MAP3 FOR4: GTTTCTCTTTCCCTTGC (SEQ ID NO: 28)

MAP3 FOR5: GCCACATTCAGCCTTCAAGGC (SEQ ID NO: 29)

MAP3 REV1: ATCCCTCCGTGATGATTGGC (SEQ ID NO: 30)

MAP3 REV2: GCAAGGGAAAGAGAAAC (SEQ ID NO: 31)

MAP3 REV1.2: AGCCCCTGCTCTGCAAGCTGCA (SEQ ID NO: 32)

MAP3 REV3: TCCATAGCCTAGAGGTGAGGG (SEQ ID NO: 33)

MAP3 REV4: AAGGCCAGCTGAACCCT (SEQ ID NO: 34)

Plasmids (phage F1 endonuclease) and *E. coli* Exonuclease III (Exo III). Hybrids between the biotinylated oligonucleotide and ssDNA are formed in solution and then captured on streptavidin-coated paramagnetic beads. A magnet is used to retrieve the paramagnetic beads from the solution, leaving nonhybridized ssDNA behind. Subsequently, the captured ssDNA target is released from the biotinylated oligonucleotide that remains attached to the para-magnetic beads. After release, the desired cDNA clone is further enriched by using a non-biotinylated target oligonucleotide to specifically prime conversion of the recovered ssDNA target to dsDNA. Following transformation and plating, typically, 20% to 100% of the colonies represent the cDNA clone of interest.

PAGE Purification of Oligonucleotides:

Oligonucleotides contaminated by significant amounts of aborted synthesis products (e.g., n−1, n−2, n−3) will yield a high percentage of background colonies if used for cDNA capture and repair. To avoid this problem, gene-specific oligonucleotides purified by gel purification on a denaturing acrylamide preparative gel (PAGE purification) were purchased from Life Technologies. The PAGE-purified oligonucleotide was diluted to 100 $\mu$M with TE buffer [10 mM Tris-HCl (pH 8.0), 1 mM EDTA). Approximately 2 to 5 OD ($A_{260}$) of oligonucleotide (33 ug=1 OD) was used and the total volume brought to 100 ul with TE buffer. 100 ul of phenol/chloroform/isoamyl alcohol (25:24:1), was added, vortexed thoroughly, and centrifuged at room temperature for 5 min at 14,000×g to separate the phases. About 90 $\mu$l of the upper, aqueous layer was removed transferred to a fresh 1.5-ml microcentrifuge tube. 45 $\mu$l of 7.5 M NH$_4$OAc was added, followed by 350 $\mu$l of absolute ethanol (−20° C.). The mixture was vortexed thoroughly, stored on dry ice for 10 min, and centrifuged at 4° C. for 10 min at 14,000×g. The supernatant was removed carefully and the pellet overlayed with 100 $\mu$l of 70% ethanol (−20° C.), centrifuged for 2 min at 14,000×g and the supernatant removed. The oligonucleotide was dried at room temperature for 10 min, or until residual ethanol has been evaporated, and dissolved in 40 $\mu$l of TE buffer. The oligonucleotide concentration was determined by measuring OD$_{260}$. The oligonucleotide concentration should be greater than 0.5 $\mu$g/$\mu$l.

| Plasmid | SEQ ID NO. | Marker | Description | Source |
|---|---|---|---|---|
| pFastBac1 | | Amp$^R$ Gent$^R$ | Baculovirus donor plasmid containing multiple cloning site downstream of an AcNPV polyhedrin promoter within a mini-Tn7 transposable element capable of being transposed to a baculovirus shuttle vector | Life Technologies Inc. (Rockville, MD) |
| pMON56500 | | Amp$^R$ Gent$^R$ | pFastBac1 NotI/EcoRI + MetAP2 PCR fragment EcoRI/NotI encoding untagged MetAP2 | This work |
| pMON56502 | | Amp$^R$ Gent$^R$ | pFastBac1 NotI/EcoRI + MetAP3 PCR fragment EcoRI/NotI encoding untagged MetAP3 | This work |
| pMON56503 | | Amp$^R$ Gent$^R$ | pFastBacHTa NotI/EcoRI + MetAP3 PCR fragment EcoRI/NotI encoding His-tagged MetAP3 | This work |
| pMON57800 | | Amp$^R$ Gent$^R$ | pFastBac1 NotI/EcoRI + MetAP1-HZ PCR fragment EcoRI/NotI encoding untagged MetAP1 | This work |
| pMON57801 | | Amp$^{R,}$ Gent$^R$ | pFastBacHTa NotI/EcoRI + MetAP1-HZ PCR fragment EcoRI/NotI encoding His-tagged MetAP-1 | This work |

EXAMPLE 3

Isolation of MetAP cDNAs Using a GeneTrapper Selection System

The GeneTrapper cDNA Positive Selection System (Catalog No.10356–046) marketed by Life Technologies, Inc. (Rockville, Md.) was used to identify clones encoding methionine aminopeptidase types 1, 2, and 3 with minor changes in the protocol noted below. The GeneTrapper cDNA Positive Selection System facilitates the rapid (1 to 2 days) isolation of cDNA clones from DNA prepared from a cDNA library (representing 10$^{12}$ DNA molecules). In this system, an oligonucleotide, complementary to a segment of the target cDNA, is biotinylated at the 3'-end with biotin-14-dCTP using terminal deoxynucleotidyl transferase (TdT). Simultaneously, a complex population of ds phagemid DNA containing cDNA inserts (10$^6$ to 10$^7$ individual members) is converted to ssDNA using Gene II Biotinylation Reaction Oligonucleotides were biotinylated using the following protocol:

| Component | Amount |
|---|---|
| 5X TdT Buffer | 5 μl |
| oligonucleotide | 3 μg |
| Biotin-14-dCTP | 5 μl |
| autoclaved, distilled water | sufficient to bring the volume to 23 μl |
| TdT | 2 μl |

The components were added to a 1.5-ml microcentrifuge tube, vortexed gently and centrifuge for 2 s at 14,000×g. The tube was incubated for 1 h at 30° C. After 1 h, 1 μl of Glycogen (20 μg/μl), 26 μl of 1 M Tris-HCl (pH 7.5), and 120 μl of ethanol were added to the oligonucleotide biotinylation reaction. The tube was vortexed and stored on dry ice for 10 min, then centrifuged at 4° C. for 30 min at 14,000×g. The supernatant was carefully and immediately removed from the microcentrifuge tubes and 200 μl of 70% ethanol (−20° C.) layered over the pellet before centrifuging at 4° C. for 2 min at 14,000×g. The ethanol wash was carefully removed from the microcentrifuge tubes. The ethanol wash was repeated once and the pellets dried at room temperature for 10 min or until completely dry. The biotinylated oligonucleotide was dissolved in 20 μl TE buffer. To determine the labeling efficiency and the concentration of the labeled oligonucleotide, 4 μl was removed for gel analysis and the remainder stored at −20° C.

Analysis of the Oligonucleotide Biotinylation Reaction Products

4 μl of formamide stop buffer was added to the 4 μl of biotinylated oligonucleotide. The tube was vortexed and centrifuged for 2 s at 14,000×g to collect the contents of the tube. The unbiotinylated oligonucleotide was diluted to 50 ng/ml, so that 4 μl contains 200 ng. 4 μl of the dilution was then mixed with 4 μl of formamide stop buffer. Samples were loaded with flat pipette tips onto a pre-poured 15% TBE-7 M Urea acrylamide/bisacrylamide gel (Catalog No. EC6885, NOVEX, San Diego, Calif.). The samples were separated by electrophoresis at 100 V for 1.5 h or until the blue dye migrates to the middle of the gel. The gel was stained in ethidium bromide solution (0.5 μg/ml) for 15 min. The gel was transferred to clear plastic wrap and photographed using transmitted ultraviolet light. The biotinylated products in each lane containing the desired oligonucleotide were compared with samples of titrated, unbiotinylated oligonucleotide in adjacent lanes. More than 80% of the oligonucleotides should be biotinylated, corresponding to 1–6 (predominantly 3–4) biotin residues per oligonucleotide.

GeneTrapper® Protocol for Semi-solid Amplification of Plasmid cDNA Libraries

Semi-solid amplification of primary cDNA transformants minimizes representational biases that can occur during the expansion of plasmid cDNA libraries (Kriegler, M. (1990) Gene Transfer and Expression: A Laboratory Manual. Stockton Press, New York, N.Y.). Ordinarily unstable clones are stabilized however when the amplification is performed at 30° C. (Hanahan, D., Jessee, J., and Bloom, F. R. (1991) Plasmid Transformation of *Escherichia coli* and Other Bacteria. Methods Enzymol. 204:63–113.).

A large stir bar and 1.35 g SeaPrep agarose (Catalog No. 50302, FMC Bioproducts, Rockland, Me.) are placed into each of four 500 ml autoclavable bottles and 450 ml of 2X LB added to each bottle. The bottles of 2X LB agarose are autoclaved for 30 minutes, cooled in a 37° C. water bath for ~2 hours until media reaches 37° C. and Ampicillin added to a concentration of 200 ug/ml. $4 \times 10^5 - 6 \times 10^5$ primary cDNA. transformants (colonies from original pSPORT1 brain library) are added to each bottle, and mixed thoroughly on a stir plate for 2 min. (The actual inoculation was calculated to be $5.4 \times 10^5$ primary human brain cDNA transformants.) The caps are tightened and the bottles are placed in an ice water bath (0° C.) such that the level of water in the bath is at the same level as the upper level of media in the bottle for 1 hour. The bottles are then removed from the ice bath, the caps loosened, and the bottles incubated at 30° C. without disturbance for 61.5 hours (40–45 hours recommended) in a gravity flow incubator. The contents of bottles were poured into centrifuge bottles and centrifuged at 8,000 rpm for 20 min at room temperature. The supernatent is discarded and the cells resuspended in a total volume of 50 ml 2X LB/12.5% Glycerol (175 ml 2X LB, 25 ml Glycerol (100%)). Two 100 μl aliquots were removed for plating, further analysis, and colony estimate. Cells can be filtered through sterile cheesecloth to remove agarose clumps if present. Final titer $3.9 \times 10^6$ cfu per ul stock. The cells were subdivided into 100 ul, 1 ml, and ~10 ml aliquots and stored at −70° C. The frozen cells can be used to prepare DNA for GeneTrapper experiments or can be further amplified in liquid at 30° C. to obtain DNA. $2.5 \times 10^9$ cells per 100 ml growth medium are used for further expansion of library.

Preparation of dsDNA from a Plasmid cDNA Library 100 ml of Terrific Broth containing 100 ug/ml ampicillin were inoculated with $2.5 \times 10^9$ cells from an amplified library in a 1-L side-baffled flask and the cells grown the cells to saturation at 30° C. Cell density is measured at $A_{590}$. Cells are diluted 1:10 to 1:20 when appropriate to ensure that the observed $A_{590}$ value is between 0.2 and 0.8. No more than 500 $OD_{590}$ units are processed at a given time. The sample is divided into two 50-ml centrifuge tubes and centrifuged at 4,800×g for 15 min at 4° C. The supernatant is poured off and the cell pellets resuspend in a total volume of 10 ml of buffer I with RNase (15 mM Tris-HCl (pH 8.0), 10 mM EDTA, RNase A (100 μg/ml), RNase T1 (1,200 units/ml)). 10 ml of freshly-prepared Buffer II (0.2 M NaOH, 1% SDS) was added to the resuspended cells, inverted gently to mix and incubated for 5 min at room temperature. 10 ml of cold 7.5 M $NH_4OAc$ was added to the cell mixture, gently inverted to mix and incubated on ice for 10 min. The sample was centrifuged at 3,000×g for 15 min at 4° C. and the supernatant poured through coffee filter into a fresh 50-ml centrifuge tube. The white flocculant material was avoided. An equal volume of cold isopropanol (−20° C.) was added, mixed well, and centrifuged at 3,000×g for 15 min at 4° C. The supernatant was discarded and the pellet resuspended in 1 ml of buffer I with RNase and transferred to a microcentrifuge tube. The solution was clarified by centrifugation at 4° C. for 1 min at 14,000×g and the supernatant transferred to a fresh microcentrifuge tube. The tube was incubated at 37° C. for 30 min, and at 65° C. for 5 min. The sample was then divided into two equal parts (~500 μl each) in 1.5-ml microcentrifuge tubes. An equal volume of phenol:chloroform:isoamyl alcohol (25:24:1) was added to each sample, vortexed, and centrifuged at room temperature for 5 min at 14,000×g. 450 μl of the upper aqueous phase was transferred to fresh microcentrifuge tubes. The phenol:chloroform:isoamyl alcohol extraction was repeated at least 3 times. An equal volume of isopropanol (−20° C.) was added to each tube and centrifuged at 4° C. for 15 min at 14,000×g. The supernatant was discarded. 500 μl of 70% ethanol was carefully added to each tube, and centrifuged at 4° C. for 5 min at 14,000×g. The supernatant was discarded and the pellet dried at room temperature for 10 min. The two pellets were dissolved in a total volume of 200 μl TE buffer. The concentration of the ds plasmid DNA library concentration should be ~1 μg/μl. The dsDNA is stored at −20° C.

Generation of ssDNA With Gene II and Exo III

For each hybridization, add the following to a 1.5-ml microcentrifuge tube at room temperature:

| Component | Amount |
| --- | --- |
| 10X Gene II Buffer | 4 μl |
| ds phagemid cDNA (~1 μg/μl) | 5 μg |
| autoclaved, distilled water | sufficient to bring the volume to 38 μl |

2 μl of Gene II was added to each tube, vortexed, and centrifuged at room temperature for 2 s at 14,000×g to collect the contents to the bottom of the tube, before incubating at 30° C. in a water bath for 25 min. The mixture is incubated at 65° C. for 5 min and immediately chilled on ice for 1 min. 2 μl of the mixture is transferred to a microcentrifuge tube containing 8 μl of TE buffer and 2 μl of gel loading dye. These samples are saved on ice for subsequent gel analysis. 4 μl of Exo III are added to the remaining 38 μl in each tube, vortexed, and centrifuged at room temperature for 2 s at 14,000×g. The samples are incubated at 37° C. for 60 min. An equal volume (40 μl) of phenol:chloroform:isoamyl alcohol (25:24:1) is added to each tube, vortexed thoroughly, and centrifuged at room temperature for 5 min at 14,000×g to separate the phases. 36 μl of the upper aqueous phase are transferred to a fresh 1.5-ml microcentrifuge tube. The ssDNA can be stored at 4° C. for several days. 2 μl of each sample are transferred to a microcentrifuge tube containing 8 μl of TE buffer and 2 μl of gel loading dye and stored on ice. The samples are analyzed by separated by electrophoresis at 1.5 h at 80 V, or until the blue dye migrates 3–4 cm, on a 0.8% agarose gel containing 0.5 μg/ml ethidium bromide in 1×TAE buffer. 250 ng of the original ds phagemid DNA and 1 μg of 1 Kb DNA Ladder are loaded into separate lanes as a control and a molecular weight marker, respectively.

Analysis of Gene II and Exo III Digestion Products

The Gene II and Gene II-Exo III-treated samples are compared to the undigested ds phagemid DNA. More than 50% of the supercoiled DNA should be nicked by the Gene II protein and migrate as open-circle DNA (the slowly migrating band). The nicked form of ds phagemid DNA generated by Gene II treatment should be completely converted to the ssDNA after the Exo III digestion (migrates faster than supercoiled). If the dsDNA is converted to ssDNA proceed with cDNA Capture Hybridization.

Oligonucleotide Hybridization

The biotinylated oligonucleotide (e.g., MAP3-For1 (SEQ ID NO: 23)) was diluted to 20 ng/μl (1:1 dilution) in TE buffer. The 4×Hybridization Buffer was incubated at 37° C. for 2 min, mixed well, and added to the remaining 34 μl of Gene II/Exo III-treated DNA. The DNA sample was mixed by pipetting up and down, denatured in a 95° C. water bath for 1 min and chilled immediately on ice for 1 min. 1 μl of diluted biotinylated oligonucleotide (MAP3-For1 (SEQ ID NO: 23)) (20 ng) was added to the denatured DNA and mixed by pipetting up and down with a pipette setting of 25 μl. The tube was incubated in a water bath or air incubator for 1 h at 37° C.

Streptavidin Bead Preparation

Streptavidin paramagnetic beads were prepared twenty min before the hybridization was complete. The beads were gently mixed by pipetting until the beads at the bottom were completely resuspended and 45 μl of the mixed beads transferred to the bottom of a microcentrifuge tube for each reaction. The tubes were inserted into the magnet and let sit for 2 min. The supernatant was carefully removed from the tubes present in the magnetic tube holder and 100 μl of TE buffer immediately added to the beads. The tube was removed from the magnet and the beads gently resuspend by finger tapping or vortexing at the lowest setting. The tube was reinserted into the magnet for 2 min, and the supernatant removed again. The beads were resuspended in 30 μl of TE buffer and the tubes placed into a microcentrifuge tube rack.

cDNA Capture

The hybridization mixture was removed from a 37° C. water bath and centrifuged at room temperature for 2 s at 14,000×g. The prepared paramagnetic beads were pipetted into the mixture and gently mixed by pipetting. The suspension was incubated for 30 min at room temperature and gently mixed frequently (every 2 to 3 min) by finger tapping or gently vortexing at the lowest setting for 10 s to resuspend the beads. The tubes were reinserted into the magnet. After 2 min, the supernatant was removed and discarded. 100 μl of Wash Buffer was added to the beads and resuspended by finger tapping or gently vortexing at the lowest setting. The wash step was repeated two additional times. 100 μl of Wash Buffer was added to the beads and the beads resuspended gently by pipetting up and down. The solution was transferred to a clean tube. The tubes were inserted into the magnet for 5 min. The supernatent was remove and discarded. 100 μl of Wash Buffer was added to each tube and gently tapped or vortexed. The tubes were inserted into the magnet again for 5 min. The supernatent was removed and discarded and 20 ul of freshly-prepared 1×Elution buffer was added to the beads and mixed well by pipetting. The beads were incubated at room temperature for 5 min, tapping the beads for about 10 s every minute. The tube was inserted into the magnet for 5 min. The supernatant (containing the captured cDNA clone) was transferred and saved in a fresh tube. The beads were resuspended in 15 μl of TE buffer. The tube was inserted into the magnet for 5 min and the supernatent combined with the supernatent from the previous step. The tube containing the combined supernatants was inserted into the magnet for 10 min to remove any remaining paramagnetic beads and the supernatant transferred to a fresh microcentrifuge tube. To the supernatant (~35 μl), add 1 μl of Glycogen, 18 μl of 7.5 M NH₄OAc, and 135 μl of ethanol (−20° C.). The sample was mixed well and store on ice for 10 min or at 4° C. overnight. The sample was centrifuged at 4° C. for 30 min at 14,000×g. The supernatant was carefully removed from the small pellets and 100 μl of 70% ethanol added to each tube. The tubes were centrifuged at room temperature for 2 min at 14,000×g. The ethanol was removed and the pellets dried at room temperature for about 10 min. The pellets were dissolved in 5 μl of TE buffer and stored at 4° C.

Repair of Captured cDNA

A DNA primer/repair mix was prepared for each capture reaction using reagents in the following proportions:

| Component | Amount |
| --- | --- |
| captured DNA | 5 μl |
| autoclaved, distilled water | 11 μl |
| 50 ng oligonucleotide (MAP3-F1 not biotinylated) | 1 μl |

-continued

| Component | Amount |
|---|---|
| 10 mM dNTP Mix | 0.5 µl |
| 10X Repair Buffer | 2 µl |
| Repair Enzyme | 0.5 µl |
| final volume | 20 µl |

The sample was mixed by pipetting and centrifuged at room temperature for 2 s at 14,000×g. The sample was incubated for a single cycle in a DNA thermal cycler: 90° C. denature step for 1 min, 55° C. annealing step for 30 s, 70° C. extension step for 15 min. The tubes were removed and centrifuged at room temperature for 2 s at 14,000×g. The repaired DNA is stored –20° C. until needed.

Transformation of Captured/Repaired DNA With ULTRAMAX DH5a-FT Cells

Frozen competent ULTRAMAX DH5a-FT *E. coli* cells were thawed on wet ice, mixed, and 100 ul aliquots dispensed into chilled polypropylene test tubes. 5 ul of each DNA sample were added to the cells, gently mixed with the cells, and incubated on ice for 30 min. The cells were heat-shocked for 45 s in a 42° C. water bath without shaking, and placed on ice for 2 min. 0.9 ml of room temperature S.O.C medium was added to each tube. The tube were shaken at 225 rpm (37° C.) for 1 h. 250 µl of the transformed cell mixture were plated on LB agar plates containing 100 µg/ml ampicillin. The plates were incubated overnight at 37° C.

Colony Hybridization to Identify Clones Containing for Full Length MetAp-3

Digoxigenin-labeled oligonucleotides were used as probes to screen recombinant bacterial libraries for specific DNA sequences. Briefly, bacterial colonies were transferred to a nylon membrane. Colonies were lysed by alkaline treatment and the denatured DNA was immobilized on the membrane. Proteinase K treatment was used to digest interfering proteins. Hybridization is carried out using a digoxigenin-labeled DNA, RNA, or oligonucleotide probe and calorimetric or chemiluminescent immunoassays are used to facilitate detection of hybridization products.

DIG-labeled probes were generated using PCR DIG Probe Synthesis Kit, Catalog #1636–090, Roche Molecular Biochemicals/Boehringer Mannheim, Indianapolis, Ind. Upstream and downstream gene-specific primers (GSP-F, GSP-R) at a concentration of 1–10 uM, and template DNAs diluted 1:100 (1–50 ng) are not provided in the kit. The following components to a sterile microcentrifuge tube placed on ice.

| Reagents | Volume | Final Concentration |
|---|---|---|
| H₂O | variable | |
| PCR buffer without MgCl₂ (Vial 3 from kit) | 10 µl | 1 × (10 mM Tris-HCl, 50 mM KCl) |
| PCR DIG Probe Synthesis Mix (Vial 2 from kit) | 10 µl | 200 µM dNTP |
| Upstream Primer @ 10 µM | 2 µl | 0.2 µM of each primer |
| Downstream Primer @ 10 µM | 2 µl | |

-continued

| Reagents | Volume | Final Concentration |
|---|---|---|
| Taq DNA Polymerase @ 5U/µl (Vial 1 from kit) | 1.5 µl | 7.5 U/100 µl |
| Template DNA @ 1:100 | 2 µl | |
| (Previous MAP3) | | |
| Total Volume | 100 µl | |

The reagents were mixed and centrifuged briefly to collect the sample at the bottom of the tube. The DNA was then amplified in a DNA thermal cycler using the following program: (1) denature at 94° C. for 2 min before the first cycle; (2) for 30 cycles (denature at 94° C. for 30 sec; anneal at 55° C. for 30 sec; extend at 72° C. for 1 min); and (3) complete the cycles with a single cycle at 72° C. for 7 min. An aliquot of each reaction mixture (10 µl) was analyzed by agarose gel electrophoresis to ensure that a specific band was amplified and was suitable as a probe for subsequent hybridization procedures.

Required Solutions:

| Solution | Description |
|---|---|
| Denaturation solution 1 | 0.5 N NaOH, 1.5 m NaCl |
| Neutralization solution 2 | 1.0 M Tris-HCl, pH 7.5; 1.5 M NaCl |
| 20 × SSC buffer | 3 M NaCl, 300 mM sodium citrate, pH 7.0 |
| 2 × SSC buffer | 0.3 mM NaCl, 30 mM sodium citrate, pH 7.0 |
| Proteinase K | 2 mg/ml Proteinase K in 2 × SSC buffer dilute Proteinase K (>600 U/ml, 14–22 mg/ml;1 to 10 in 2 × SSC) |
| Prehybridization solution | DIG Easy Hyb |
| Hybridization solution | DIG-labeled probe, diluted in DIG Easy Hyb |
| 2 × Wash solution | 2 × SSC, containing 0.1% SDS |
| × Wash solution | 0.5 × SSC, containing 0.1% SDS |

Two layers of Whatman 3MM filter paper are used for each different solution: denaturation solution, neutralization solution, and 2×SSC. Colonies on agarose plates were cooled to 4° C. for approx. 30 min. A membrane disc (ø 82 mm) was placed onto the surface of each plate for about 1 min and the orientation of each membrane was appropriately marked. The membrane disc was carefully removed with tweezers and blotted briefly (colonies side up) on dry Whatman 3MM paper. The membrane discs (colonies side up) were placed on the prepared filter paper soaked with denaturation solution and incubated for 15 min. The membrane was blotted briefly on Whatman 3MM paper and placed (colonies side up) on the prepared filter paper soaked with neutralization solution for 15 min. The membrane was blotted briefly on Whatman 3MM paper and placed on filter paper soaked with 2×SSC for 10 min. The DNA was crosslinked to the membrane with TV-light or by baking at 80° C. for 2 hours.

Proteinase K Treatment

Membranes were placed in a clean sealable dish containing 0.5 ml of 2 mg/ml Proteinase K on each membrane disc (0.5 ml for the ø 82 mm discs). The solution was distributed evenly, and incubated for 1 h at 37° C. Cellular and agar debris on the membranes were removed by wiping with paper towels soaked with 2×SSC.

Hybridization

Up to 3 membrane discs (ø 82 mm) were placed in a roller bottle, containing 60 ml DIG Easy Hyb solution prewarmed to 42° C. The samples were prehybridized for 1 h in a hybridization oven at 42° C. The labeled probe (90 ul) was denatured (double-stranded probes only) by boiling for 10 min at 95–100° C. and rapidly cool on ice. The denatured probe was mixed with 20 ml DIG Easy Hyb solution per each roller bottle, prewarmed to hybridization temperature. The prehybridization solution was removed and discarded. The hybridization solution was added to the membranes and incubated overnight at 42° C. in hybridization oven. At the end of the hybridization, the hybridization solution was poured into a tube that can withstand freezing and boiling (e.g., a 50 ml polypropylene tube).

Stringency Washes:

The membranes were washed twice for 5 min in ample 2×SSC, 0.1% SDS min at room temperature with gentle agitation. The membranes were then transferred to 0.5×SSC, 0.1% SDS and washed twice for 15 min at 68° C. with gentle agitation.

Detection of DIG-labeled Nucleic Acids:

A DIG Luminescent Detection Kit (Catalog No. 1363 514) and a DIG Wash and Block Buffer Set (Cat. No. 1585762), Roche Molecular Biochemicals/Boehringer Mannheim, Ind., was used for the chemiluminescent detection of digoxigenin-labeled nucleic acids. Briefly, membranes are treated with Blocking Reagent to prevent non-specific attraction of antibody to the membrane. Then, membranes are incubated with a dilution of Anti-Digoxigenin, Fab fragments, which are conjugated to alkaline phosphatase. In the third step, the membrane carrying the hybridized probe and bound antibody conjugate is reacted with a chemiluminescent substrate and exposed to X-ray film to record the chemiluminescent signal.

| Reagent | Description |
| --- | --- |
| Washing buffer (Bottle 1; dilute 1:10 with H$_2$O) | 100 mM maleic acid, 150 mM NaCl; pH 7.5 (+20° C.); 0.3% (v/v) Tween ® 20 |
| Maleic acid buffer (Bottle 2; dilute 1:10 with H$_2$0) | 100 mM maleic acid, 150 mM NaCl; pH 7.5 (+20° C.) |
| Blocking solution (Bottle 3; dilute 1:10 with 1 × Maleic acid buffer) | 1% (w/v) Blocking reagent for nucleic acid hybridization dissolved in Maleic acid buffer. Blocking solution is cloudy and should not be filtered. It is stable for at least two weeks when stored at +4° C., but must then be brought to room temperature before use. |
| Detection buffer (Bottle 4; dilute 1:10 with H$_2$O) | 100 mM Tris-HCl, 100 mM NaCl; pH 9.5 (+20° C.) |

Detection:

All incubations were performed at room temperature in clean plastic trays. After the hybridization and post-hybridization stringency washes, the membrane was equilibrated in washing buffer for 1 min. The membrane was first blocked by gently agitating it in blocking solution for 30–60 min. Longer blocking times are acceptable. The blocking solution was discarded and the membrane incubated for 30 min in antibody solution containing a 1:10,000 dilution of Anti-Digoxigenin-AP antibody. The antibody solution was discarded and the membrane washed twice, 15 min per wash, in washing buffer. The washing buffer was poured off and the membrane equilibrated in detection buffer for 2 min. The membrane was placed between two sheets of acetate (plastic page protectors). Approximately 0.5 ml (per cm$^2$) of the chemiluminescent substrate, CSPD, was placed on top of the membrane, the top sheet replaced, and any bubbles removed. The filter was incubated for 5 min. The semi-dry membranes were sealed in a plastic bag and exposed Lumi-Film standard X-ray film.

Colony Selection:

Positive colonies were selected by aligning the autoradiograph to the original LB+Amp plates from which the membranes lifts were generated. Colonies were picked with a sterile Pipet tip and used to inoculate small volumes of culture broth (3 ml LB+Amp 100 ug/ml) that were incubated overnight at 37° C. with shaking. Plasmid DNA was isolated from 1.5 ml cultures using Promega Wizard Plus Miniprep DNA Purification kits, Cat No. A7500, Promega Corporation, Madison, Wis. Plasmid DNAs were screened by restriction analysis and/or DNA sequencing using vector specific oligonucleotide primers.

EXAMPLE 4

Tissue Distribution of Methionine Aminopeptidases 1, 2, and 3 by TaqMan Analysis Taqman is a PCR-based assay which achieves great specificity and sensitivity by introducing a dual-labeled fluorogenic probe. The assay allows the detection of target messages using two oligonucleatides and a DNA probe. The probe contains a fluorescent reporter ant the 5' end and a fluorescent quencher at the 3' end. The fluorescent reporter is released during the exponential phase of PCR by the 5'–3' nuclease activity of Taq polymerase. An initial RT step is followed by 40 PCR cycles. Fluorescence is measured real-time during the extension phase of each PCR cycle.

TaqMan Primer/probe Design and Optimization

TaqMan primers and probes were designed using Primer Express Software (P.E. Biosystems, Foster City, Calif.) based on the nucleotide sequences of MetAP1, 2, and 3. Forward and reverse primers are unlabeled and oligonucleotide probes are labeled with FAM (reporter dye) at the 5' end and with TAMRA (quencher dye) at the 3' end.

MetAP1 hmap1F1: 5'-AAGCGGTCTGCTCAGTTTGAG-3' (SEQ ID NO: 38)

hmap1R1: 5'-GGCCGTGCACTGTCAAGT-3' (SEQ ID NO: 39)

hmap1P1: 5'-ACACCCTCCTGGTCACAGACACTGGC-3' (SEQ ID NO: 40)

MetAP2 hmap2F1: 5'-GACCCTCCCTCAGTTCCAATATG-3' (SEQ ID NO: 41)

hmap2R1: 5'-GTGGGTGGGTATTCGCATTC-3' (SEQ ID NO: 42)

hmap2P2: 5'-ACCTGTATCCTAATGGTGTATTTCCCAAAGGACA-3' (SEQ ID NO: 43)

MetAP3 hmap3F1: 5'-GGCATCATGCAAACGACAGT-3' (SEQ ID NO: 44)

hmap3R1: 5'-ACTGCGCCGACCTTTGATT-3' (SEQ ID NO: 45)

hmap3P1: 5'-AGAGCCAATCATCACGGAGGGATCC-3' (SEQ ID NO: 46)

MetAP2 Alternate Set map2bF: 5'-TTGGAAGACTGTTCACGCAAGT-3' (SEQ ID NO: 47)

map2bR: 5'-GTCACCGGCATTGGGAGTAT-3' (SEQ ID NO: 48)

map2bP: 5'-TGGATGTTCTCTCAATAATTGTGCTGCCCAT-3' (SEQ ID NO: 49)

MetAP3 Alternate Sets mp3bF: 5'-AACGTGCTCTGTCATGGTATTCC-3' (SEQ ID NO: 50)

mp3bR: 5'-AGCCATTGTAATAGACTGTGACATCAA-3' (SEQ ID NO: 51)

mp3bP: 5'-ACAGTCGACCTCTTCAGGATGGAGATATTATCAAC-3' (SEQ ID NO: 52)

mp3cF: 5'-CATGGAGACACCTCTGAAACATTT-3' (SEQ ID NO: 53)

mp3cR: 5'-CCTGGCAACCTCCACTAACTTT-3' (SEQ ID NO: 54)

mp3cP: 5'-CACATTCGTCCTCATTGCCCACCA-3' (SEQ ID NO: 55)

All TaqMan primers and probes were synthesized by P.E. Biosystems (Foster City, Calif.). Primers were supplied lyophilized and reconstituted with RNase-free water (Sigma Company, St. Louis, Mo.). Primers were supplied already reconstituted at 100 μM. All TaqMan reactions were performed in a 25 μl volume using One-Step RT-PCR kits, PCR Core kits, MuLV reverse transcriptase and RNase inhibitor from P.E. Biosystems (Foster City, Calif.). Reactions were performed according to manufacturer's instructions and analyzed using the ABI 7700 Sequence Detector System and Sequence Detection Software from P.E. Biosystems.

HUVEC total RNA was isolated using the ABI 6700 High-Throughput Sample Preparation workstation according to manufacturer's instructions. The RNA was then DNase treated to remove trace amounts of contaminating genomic DNA by incubating with RNase-free DNase (Promega, Madison, Wis. or Roche Molecular Biochemicals, Indianapolis, Ind. or Life Technologies, Gaithersburg, Md.) for at least 15 minutes at 37° C. DNase was then removed by purification over RNeasy minispin columns according to manufacturer's instructions for RNA cleanup (Qiagen, Valencia, Calif.). RNA samples were quantitated by reading the absorbance at 260 nm on a Beckman D-40 Spectrophotometer (Irvine, Calif.).

Specificity for the primers/probe sets was determined using MetAP1, 2, 3 cDNAs which had been cloned into plasmids. The following combinations were tested in TaqMan PCR reactions to demonstrate that the primer/probe sets worked and were specific for the cDNA they were designed for. Results are indicated as either "+" for positive reaction or "−" for little/negligible reaction.

| cDNA in plasmid | MetAP1 primer/ probe | MetAP2 primer/ probe | MetAP3 primer/ probe | MetAP3b primer/ probe | MetAP3c primer/ probe |
|---|---|---|---|---|---|
| MetAP1 | + | − | − | − | − |
| MetAP2 | − | + | − | − | − |
| MetAP3 | − | − | + | + | + |

The MetAP2b primer/probe set did not work well and was never tested for specificity. It was never used in subsequent assays.

Once specificity was demonstrated, the primer/probe sets were tested against HUVEC (human umbilical vein endothelial cells) total RNA to determine optimal assay conditions. Standard curves were set up using 200 ng, 40 ng, 8 ng, 1.6 ng and 0.32 ng HUVEC total RNA. One-step RT-PCR reactions were performed using forward and reverse primers (500 nM each final concentration) and probe (100 nM final concentration). These conditions were determined to be optimal for MetAP1, MetAP2 and MetAP3b and MetAP3c primer/probe sets. The MetAP3 primer/probe set was not as optimal as the others and was not used for further assays. MetAP3c was chosen for all assays looking at MetAP3 expression levels.

Tissue Analysis Using TaqMan Technology

Human total brain RNA was obtained from Clontech (Palo Alto, Calif.) and DNase treated as described in Materials and Methods. Roughly 200 ng total RNA was used in duplicate TaqMan reactions to determine the relative message levels of MetAP1, 2, and 3 in human brain samples. A TaqMan primer/probe set for human cyclophilin was used as an endogenous control to normalize for slight differences in the amounts of RNA assayed. Human cyclophilin is a housekeeping gene which was chosen as an endogenous control because message levels of that gene do not vary among tissue sources within a species or with differential treatment. The sequences of the human cyclophilin message primers and probes are as follows:

hcycmesF: 5'-CCCACCGTGTTCTTCGACAT-3' (SEQ ID NO: 53)

hcycmesR: 5'-TTTCTGCTGTCTTTGGGACCTT-3' (SEQ ID NO: 54)

hcycmesP: 5'-CGCGTCTCCTTTGAGCTGTTTGCA-3' (SEQ ID NO: 55)

The results indicated that 3–4 fold more MetAP1 RNA than MetAP3 RNA was present in human brain samples. About 5–6 fold more MetAP2 RNA than MetAP3 RNA was present in human brain samples.

Relative expression levels of MetAP1,2,3 were also determined from polyA+ purified RNA from human brain and HUVEC cells (polyA+ RNA obtained from Cindy Woods). 50 ng polyA+ RNA was used in the assay and human cyclophilin was used as a normalizer. Results indicate that in the human brain polyA+ RNA there is roughly the same amount of MetAP1 as MetAP3 but 8-fold more MetAP2 than MetAP3. In HUVEC polyA+ RNA, there is almost 6-fold more MetAP1 than MetAP3 and almost 10-fold more MetAP2 than MetAP3.

At this point in the project, further sequencing on the MetAP3 cDNA indicated that the original sequence used for TaqMan primer/probe design had one nucleotide difference in the region where the MetAP3c probe annealed. A new MetAP3c probe was reordered to be used in TaqMan reactions with the MetAP3c forward and reverse primer. The sequence and name of that probe is below:

revmp3cP: 5'-CACATTCGTCCACATTGCCCACCA-3' (SEQ ID NO: 56)

This new probe will be used in all subsequent TaqMan reactions to determine MetAP3 expression levels.

Several tumor samples were also analyzed for MetAP1, 2,3 expression levels. The following polyA+ RNA samples were obtained from BioChain Institute, Inc. (San Leandro, Calif.):

3 colon cancer samples from different individuals 1 colon cancer sample and 1 adjacent normal colon sample from same individual 1 normal breast sample 1 breast cancer sample and 1 breast cancer from lymph node sample from same individual 1 metastatic colon cancer sample and 1 adjacent normal liver sample from same individual 20 ng polyA+ RNA was used per TaqMan reaction and human cyclophilin was used as an endogenous control. To analyze the data, MetAP1 was chosen as a calibrator and relative expression levels of MetAP1 were set to 1." Levels of MetAP2 and MetAP3 were compared to the expression levels of MetAP1 in each tissue. Results indicate that in all tissues (both normal and tumor) levels of MetAP2 ranged from 4–18 fold, higher than levels of MetAP1. Levels of MetAP1 were roughly equivalent to levels of MetAP3. No significant differences were observed in normal vs. tumor samples.

A summary of the results are displayed in FIGS. 8–18.

Thermocycler: ABI 6700 Taqman robot.

Tagman Thermocycling Conditions:
    48° C. 30'
    95° C. 10'
    95° C. 15"
    60° C. 60"
    Repeat 40 cycles
    25° C. 2'

MetAP Tissue: Distribution:
    Primer/Probe Set for MetAP3:
        mp3cF, mp3cR, revmp3cp
    Primer/Probe Set for Human Cyclophilin:
        mp3cF, mp3cR, revmp3cp
    RNA: Total RNA from Clontech
        Panels 1–5 with 6 tissues per panel
    Reagents:
        2X Mastermix
            AmpliTaq Gold
            dNTPs with dUTP
            ROX passive reference
            PCR buffer
        40X Mastermix
            MLV reverse transcriptase
            Rnase Inhibitor

| Reaction: | Volume |
| --- | --- |
| Total RNA (16.7 ng/uL) | 6.0 uL |
| 2X Mastermix | 12.5 uL |
| 40X Mastermix | 0.675 uL |
| Probe (10 pmol/uL) | 0.25 uL |
| F Primer (100 uM) | 0.125 uL |
| R Primer (100 uM) | 0.125 uL |
| H$_2$O | 5.3 uL |
| Total | 25 uL |

MetAP3 Distribution in human brain:
    Primer/Probe Set for MetAP3:
        mp3cF, mp3cR, revmp3cp
    Primer/Probe Set for Human Cyclophilin
        hcymesF, hcymesR, hcymesP
    RNA: Poly(A)+ RNA from Clontech
    Reagents:
        2X Mastermix
            AmpliTaq Gold
            dNTPs with dUTP
            ROX passive reference
            PCR buffer
        40X Mastermix
            MLV reverse transcriptase
            Rnase Inhibitor

| Reaction | Volume |
| --- | --- |
| Poly(A) RNA (2.5 ng/uL) | 8.0 uL |
| 2X Mastermix | 12.5 uL |
| 40X Mastermix | 0.675 uL |
| Probe (10 pmol/uL) | 0.25 uL |
| F Primer (100 uM) | 0.125 uL |
| R Primer (100 uM) | 0.125 uL |
| H$_2$O | 3.375 uL |
|  | 25 uL |

Calculating Fold Expression:
    Avg CT (PCR cycle): average of the CTs for replicates
    dCT: (Avg CT of Target—Avg. CT of control)
    ddCT: (dCT of Target—dCT of Calibrator)
    Relative Expression: $(1+E)^{ddCT}$ where E is the efficiency of amplification, assumed to be one.

EXAMPLE 5

High Throughput Methionine Aminopeptidase-2 (MetAP-2) Assay

A recombinant baculovirus stock harboring the human MAP2 gene which was capable of expressing the HA-tagged human MetAP2 in cultured insect cells (Sf21) was obtained from Y-H. Chang, St. Louis University. Large (40 liter) bioreactors were used to scale up expression of the recombinant protein. The resulting cell paste which was clarified and solubilized for purification as described below.

The enzyme was partially purified according to the procedure of Li and Chang (*Biochem. Biophys. Res. Comm.* 227: 152–159, 1996). 16 g of cell paste was solubilized in 20 mM HEPES, 0.5 mM CoCl$_2$, 10% glycerol, pH 7.4. The resultant solution was centrifuged at 10,000×g for 10 min and subsequently filtered through a 0.45 µm filter to clarify. This solution was eluted from an S-sepharose column in the presence of a linear KCl gradient. The fumagillin sensitive MetAP activity was pooled and used for enzyme analysis. This solution was approximately 30% pure by SDS-PAGE.

$^{14}$C-Met-Gly-Met-Met-Lys(biotin) was prepared by American Radiolabeled Chemicals Inc., St. Louis, Mo. 63146. The cold peptide was synthesized by American Peptide Co., Sunnyvale, Calif. 94086. Sufficient peptide was added to the reaction to result in a 0.1 mM final concentration. The starting enzyme assay contained 50–60,000 cpm per reaction.

The avidin capture beads were prepared by reacting avidin with Bio-Rad Affi-Gel® 10 Gel (Cat. 153–1000). The ImmunoPure® Avidin (#21128B) was purchased from Pierce. 500 mL of resin slurry was washed three times with excess cold Millipore water (18.2 megohm). The washed resin was slurried with 1 liter of cold 20 mM HEPES, 0.01% sodium azide, pH 7.5 buffer containing 5 g of ImmunoPure® Avidin. This solution was mixed continuously at 4° C. for 48 hrs. The beads were then allowed to settle and the supernatant was decanted. The avidin coated affi-gel was resuspended in 1 M glycine ethyl ester (Sigma #G-8001) pH 8.0 for two hours. The supernatant was decanted and the beads were washed three times with excess cold 20 mM HEPES, 0.01%. sodium azide, pH 7.5 buffer. The avidin gel was finally suspended in 20 mM HEPES, 0.01% sodium azide, pH 7.5 buffer containing 2% Triton X-100 at a 2.6:1 ratio of buffer to the gel. This solution was stirred continuously during an enzyme experiment.

A typical MetAP reaction contains 0.1 mM Met-Gly-Met-Met-Lys(biotin), 50–60,000 CPM $^{14}$C-Methionine-Gly-Met-Met-Lys(biotin), 0.2–0.5 µg of partially purified MetAP-2. The reaction buffer contains 20 mM HEPES, 0.5 mM CoCl$_2$, 10% glycerol, pH 7.4. The reaction is initiated by the addition of substrate. The assay is mixed and allowed to stand, covered at room temperature for 30 min. MetAP-2 turnover is stopped by the addition of 150 µL of the avidin-affigel resin slurry. The slurry is thoroughly mixed with the reaction and allowed to settle for 10 min. 50 µL of the resultant supernatant containing the free $^{14}$C-methionine is transferred to a TopCount plate and 200 µL of Scint 40 is added. The results are then counted on a Packard TopCount counter.

MetAP1 and MetAP3 are assayed using the same procedure.

EXAMPLE 6

Generation of Polyclonal Antibodies Recognizing Methionine Aminopeptidase Type 1, 2, and 3

Polyclonal antibodies against MetAP 1, 2, and 3 were generated by synthesizing peptides that correspond to amino acids 11–135 of AMPM_*E. coli*. An N terminal cysteine was used to facilitate conjugation to KLH. Peptides corresponding to amino acids 216–226 of AMPM_*E. coli*, near the active site of this molecule, were synthesized and expected to block the activity the corresponding MetAP.

```
MetAP1 peptide antigen

Asn Glu Thr Phe Phe Val Gly Glu Val Asp Asp Gly Ala Arg Lys Leu
 1               5                  10                  15
Val Gln Thr Thr (SEQ ID NO: 57)
            20
MetAP2 peptide antigen Cys Ala Phe Thr Val Thr Phe Asn Pro Lys Tyr Asp Thr Leu Leu Lys
 1               5                  10                  15
Ala Val Lys Asp (SEQ ID NO: 58)
            20
MetAP3 peptide antigen Ser Glu Thr Phe Leu Val Gly Asn Glu Asp Glu Ala Gly Lys Lys Leu
 1               5                  10                  15
Val Glu Val Ala (SEQ ID NO: 59)
            20
MetAP1 blocking peptide antigen Gly Trp Gln Asp Glu Thr Trp Pro Asp Gly Trp Thr Ala Val Thr Arg
 1               5                  10                  15
Asp Gly Lys Arg (SEQ ID NO: 60)
            20
MetAP2 blocking peptide antigen Cys Ser His Tyr Met Lys Asn Phe Asp Val Gly His Val Pro Ile Arg
 1               5                  10                  15
Leu Pro Arg Thr (SEQ ID NO: 61)
            20
MetAP3 blocking peptide antigen Gly Ser Pro Glu Phe Lys Val Leu Glu Asp Ala Trp Thr Val Val Ser
 1               5                  10                  15
Leu Asp Asn Gln (SEQ ID NO: 62)
            20
```

Polyclonal rabbit anti-MetAP1, 2, and 3 antibodies were prepared by Covance using standard injection protocols supplied by the service provider.

REFERENCES

Each of the references below is specifically incorporated herein in their entirety. In addition, these references can be relied upon to make and use aspects of the invention.

Anfossi et al., Proc. Natl. Acad. Sci. (U.S.A.) 86:3379–3383 (1989)
Arfin et al. Proc. Natl. Acad. Sci. (U.S.A.) 92:7714–7718 (1995)
Armour, et al., FEBS Lett. 307:113–115 (1992)
Baldwin et al., Gene Ther. 4:1142–1149 (1997)
Barany, Proc. Natl. Acad. Sci. (U.S.A.) 88:189–193 (1991)
Bassat et al., J. Bacteriol. 169:751–757 (1987)
Baum et al., J. Hematother. 5: 323–329 (1996)
Becker et al., EMBO J. 8:3685–3691 (1989)
Ben-Bassat et al., J. Bacteriol. 169:751–757 (1987)
Berkner, BioTechniques 6:616–629 (1988)
Berkner, Current Top. Microbiol. Immunol. 158:39–66 (1992)
Blobel and Dobberstein, J. Cell Biol. 67:835–851 (1975)
Boris-Lawrie and Temin, Annal. New York Acad. Sci. 716:59–71 (1994)
Boris-Lawrie and Temin, Curr. Opin. Genet. Dev. 3:102–109 (1993)

Bostian et al., Cell 36:741–751 (1984)
Botstein et al., Ann. J. Hum. Genet. 32:314–331 (1980)
Bregni et al., Blood 80:1418–1422 (1992)
Brody and Crystal, Annal. New York Acad. Sci. 716:90–103 (1994)
Capecchi, Cell. 22:479–488 (1980)
Chen et al., Gene Ther. 5:50–58 (1998)
Clapp, Clin. Perinatol. 20:155–168 (1993)
Collins, In: Alternative Immunoassays, John Wiley & Sons, N.Y. (1985)
Corbi and Lopez-Rodriguez, Leuk. Lymphoma 25:415–425 (1997)
Crabeel et al., EMBO J. 2:205–212 (1983)
Curiel et al., Hum. Gen. Ther. 3:147–154 (1992)
Current Protocols in Molecular Biology, John Wiley & Sons, N.Y. (1989)
Datta et al., Proc. Natl. Acad. Sci. USA 85: 3324–2238 1(1988)
Derynck et al., Nucleic Acids Res. 11:1819–1837 (1983)
Dobson et al., Nucleic Acids. Res. 11:2287–2302 (1983)
Dunbar et al., Blood 85:3048–3057 (1995)
Eglitis and Anderson, Biotechniques, 6:608–614 (1988)
ELISA and Other Solid Phase Immunoassays (Kemeny, et al., Eds.), John Wiley & Sons, N.Y. (1988)
Elshami et al., Cancer Gene Ther. 4:213–221 (1997)
Fackrell, Clin. Immunoassay 8:213–219 (1985)
Fernandez de Henestrosa et al., FEMS Microbiol. Lett. 147:209–213 (1997)
Frohman, M. A. et al., Proc. Natl. Acad. Sci. (U.S.A.) 85:8998–9002 (1988)
Fromm et al., Nature 319:791 (1986)
Fromm et al., Proc. Natl. Acad. Sci. (U.S.A.) 82:5824–5828 (1985)
Gerwirtz et al., Science 242:1303–1306 (1988)
Goff et al., EMBO J. 9: 2517–2522 (1990)
Goodchild et al., Proc. Natl. Acad. Sci. (U.S.A.) 85:5507–5511 (1988)
Graham and van der Eb, Virology 54:536–539 (1973)
Gray et al., Proc. R. Acad. Soc. Lond. 243:241–253 (1991)
Griffith et al. Chem. Biol. 4:461–471 (1997)
Griffiths et al., Biochem. J. 241: 313–324 (1987)
Guarente and Ptashne, Proc. Natl. Acad. Sci. (U.S.A.) 78:2199–2203 (1981)
Gusella, Ann. Rev. Biochem. 55:831–854 (1986)
Hallek et al., Cytokines Mol. Ther. 2: 69–79 (1996)
Harley and Reynolds, Nucleic Acids Res. 15:2343–2361 (1987)
Harlow and Lane, In Antibodies: A Laboratory Manual, Cold Spring Harbor Press, Cold Spring Harbor, N.Y. (1988)
Harms and Splitter, Hum. Gene Ther. 6:1291–1297 (1995)
Hasan et al., Gene 56:141–151 (1987)
Hattori et al., Genes Dev. 6: 609–618 (1992)
Hawley and McClure, Nucleic Acids Res. 11:2237–2255 (1983)
Haymes, et al. Nucleic Acid Hybridization, A Practical Approach, IRL Press, Washington, D.C. (1985)
Hillel et al., Anim. Genet. 20:145–155 (1989)
Hillel et al., Genet. 124:783–789 (1990)
Hitzeman et al., Nature 293:717–722 (1981)
Holt et al., Molec. Cell. Biol. 8:963–973 (1988)
Ingber et al. Nature 348:555–557, (1990)
Janknecht et al., Carcinogenesis 16:443–450 (1995)
Janknecht Immunobiology 193:137–142 (1995)
Jefferson et al., EMBO J. 6: 3901–3907 (1987)
Jefferson Plant Mol. Biol. Rep. 5: 387–405 (1987)
Jeffreys et al., Anim. Genet. 18:1–15 (1987)
Jeffreys et al., Amer. J. Hum. Genet. 39:11–24 (1986)
Jeffreys et al., Nature 316:76–79 (1985)
Johnston and Tang, Methods Cell Biol. 43:353–365 (1994)
Jones et al., Eur. J. Haematol. 39:144–147 (1987)
Julius et al., Cell 32:839–852 (1983)
Julius et al., Cell 36:309–318 (1984)
Kendall and Bradshaw, J. Biol. Chem. 267:20667–20673 (1992)
King and Possee, The Baculovirus Expression System: A Laboratory Guide, London, Chapman & Hall
Kurjan and Herskowitz, Cell 30:933–943 (1982)
Kusaka et al., Biochem. Biophys. Res. Commun. 174:1070–1076 (1991)
Kwoh et al., Proc. Natl. Acad. Sci. (U.S.A.) 86:1113 (1989)
Laboratory Techniques and Biochemistry in Molecular Biology, by Work, et al., North Holland Publishing Company, N.Y. (1978)
Landegren et al., Science 241:1077–1080 (1988)
Langer R. et al., Chem. Tech. 12:98 (1982)
Li and Chang, Biochem. Biophys. Res. Comm. 227: 152–159 (1989)
Lorz et al., Mol. Gen. Genet. 199:178 (1985)
Lu et al., J. Exp. Med. 178:2089–2096 (1993)
Luckow et al., J. Virol. 67: 4566–4579 (1993)
Luckow Protein Eng. J. L. Cleland., Wiley-Liss, New York, N.Y.: 183–2180 (1996)
Marcotte et al., Nature 335:454–457 (1988)
Marsh, Nucleic Acids Res. 14:3603 (1986)
McCarty et al., Cell 66: 895–905 (1991)
McCowen et al., Science 113:202–203 (1951)
Miller Current Top. Microbiol. Immunol. 158:1–24 (1992)
Miller et al., Proc. Natl. Acad. Sci. (U.S.A.) 91:2473–2477 (1987)
Moore et al., Genomics 10:654–660 (1991)
Mori and Prager, Leuk. Lymphoma 26:421–433 (1997)
Mullis et al., Cold Spring Harbor Symp. Quant. Biol. 51:263–273 (1986)
Ngo et al., In: Enzyme Mediated Immunoassay, Plenum Press, N.Y. (1985)
Nickerson et al., Proc. Natl. Acad. Sci. (U.S.A.) 87:8923–8927 (1990)
Norman et al., Vaccine 15:801–803 (1997)
Nussbaumer et al., FEMS Microbiol. Lett. 118:57–63 (1994)
O'Neill et al., Transplant Proc. 23:2862–2866 (1991)
Obukowicz et al., Applied Environmental Microbiology 58:1511–1523 (1992)
Ohara et al., Proc. Natl. Acad. Sci. (U.S.A.) 86:5673–5677 (1989)
O'Reilly et al., Baculovirus Expression Vectors: A Laboratory Manual. New York, W.H. Freeman and Company (1992)
Ow et al., Science 234: 856–859 (1986)
Peseckis et al., J. Biol. Chem. 267:5107–5114 (1993)
Potrykus et al., Mol. Gen. Genet. 205:193–200 (1986)
Rachal et al., EXS 64:330–342 (1993)
Ray et al., Adv. Exp. Med. Biol. 280:107–111 (1990)
Remington's Pharmaceutical Sciences, 16th ed., Osol, Ed., Mack, Easton Pa. (1980)
Roderick and Matthews, Biochemistry 32:3907–3912 (1993)
Romanos et al., Yeast 8:423–488 (1992)
Rose et al., Proc. Natl. Acad. Sci. (U.S.A.) 78:2460–2464 (1981)
Rothman and Orci, Nature 355:409–415 (1992)
Sambrook et al., Molecular Cloning, A Laboratory Manual, 2nd Ed., Cold Spring Harbor Press, Cold Spring Harbor, N.Y. (1989)

Serfing et al., Biochim. Biophys. Acta 1263:181–200 (1995)
Shannon et al., Crit. Rev. Immunol. 17:301–323 (1997)
Sidman U. et al., Biopolymers 22:547 (1983)
Sin et al. Proc. Natl. Acad. Sci. (U.S.A.) 94:6099–6103 (1997)
Skolnick, M. H. et al., Cytogen. Cell Genet. 32:58–67 (1982)
Suh et al., Gene 169:17–23 (1996)
Sun et al., Curr. Top. Microbiol. Immunol 211:173–187 (1996)
Sutcliffe et al., Proc. Natl. Acad. Sci. (U.S.A.) 75: 3737–3741 (1978)
Takai et al., Princess Takamatsu Symp. 22:197–204 (1991)
Tong et al., Anticancer Res. 18:719–725 (1998)
Tuite et al., EMBO J. 1:603–608 (1982)
Uchimiya et al., Mol. Gen. Genet. 204:204 (1986)
Valenzuela et al., Nature 298:347–350 (1982)
Wagner et al., Proc. Natl. Acad. Sci. (U.S.A.) 89:6099–6103 (1992)
Walker et al., Proc. Natl. Acad. Sci. (U.S.A.) 89:392–396 (1992)
Weinberg et al., Gene 126:25–33 (1993)
Weisemann et al., Biochimie 73: 457–470 (1991)
Wickstrom et al., Proc. Natl. Acad. Sci. (U.S.A.) 85:1028–1032 (1988)
Wong and Neumann Biochem. Biophys. Res. Commun. 107:584–587 (1982)
Wu et al., J. Biol. Chem. 268:10796–10781 (1993)
Wu, et al., Genomics 4:560 (1989)
Yanish-Perron et al. Gene 33:103–119 (1985)
Yolken Rev. Infect. Dis. 4:35 (1982)
Zamechik et al., Proc. Natl. Acad. Sci. (U.S.A.) 83:4143–4146 (1986)

TABLES

TABLE 1

CLUSTAL W (1.74) multiple sequence alignment

```
MAP-3_insertion    ----------------------------------------------------------
MAP-3_fl           -----------------------------------------------------MAAPS
AMP1_HUMAN         ------------------ALFQRAGSMAAVETRV-CETDGCS--SEAKLQCPTCIKL
AMP1_YEAST         -----------------MSTATTTVTTSDQASHPTKIYCSGLQCGRETSSQMKCPVCLKQ
AMP2_SYNY3         ----------------------------------------------------------
AMP2_SYNY3         ----------------------------------------------------------
AMPM_ECOLI         ----------------------------------------------------------
AMPM_HAEIN         ----------------------------------------------------------
AMP3_SYNY3         ----------------------------------------------------------
AMPM_BACSU         ----------------------------------------------------------
AMP2_MOUSE         MAGVEQAASFGGHLNGDLDPDDREEGTSSTAEEAAKKKRRKKKKGKGAVSAVQQELDKES
AMP2_RAT           MAGVEEASSFGGHLNRDLDPDDREEGTSSTAEEAAKKKRRKKKKGKGAVSAGQQELDKES
AMP2_HUMAN         MAGVEEVAASGSHLNGDLDPDDREEGAASTAEEAAKKKRRKKKKSKGPSAAGEQEPDKES
AMP2_YEAST         ---------------------------------------------------MTDAEIEN
AMPM_METJA         ----------------------------------------------------------
AMPM_SULSO         ----------------------------------------------------------
AMPM_METFE         ----------------------------------------------------------
AMPM_HELPY         ----------------------------------------------------------
MAP-3_insertion    ----------------------------------------------------------
MAP-3_fl           GVHLLVRRGSHRIFSSPLNHIYLHKQSSSQ------------QRRNFFFRRQRDISHSIV
AMP1_HUMAN         GIQGSYFCSQECFKGSWATHKLLHKKAKDEKAKREVSSWTVEGDINTDPWAGYRYTGKLR
AMP1_YEAST         GIV-SIFCDTSCYENNYKAHKALHN-AKDG----------LEG--AYDPFPKFKYSGKVK
AMP1_SYNY3         ----------------------------------------------------------
AMP2_SYNY3         ----------------------------------------------------------
AMPM_ECOLI         ----------------------------------------------------------
AMPM_HAEIN         ----------------------------------------------------------
AMP3_SYNY3         ---------------------------------------------MPRIFPWKLWRKSR
AMPM_BACSU         ----------------------------------------------------------
AMP2_MOUSE         GALVDEVAKQLESQALEEKERDDDDEDGDGDADGATGKKKKKKKKKRGPKVQTDPPSVPI
AMP2_RAT           GTSVDEVAKQLERQALEEKEKDDDDEDGDGDGDGAAGKKKKKKKKKKRGPRVQTPPDSVPI
AMP2_HUMAN         GASVDEVARQLERSALEDKERDEDDEDGDGDGDATGKKKKKKKKKRGPKVQTDPPSVPI
AMP2_YEAST         SPASDLKELNLENEGVEQQDQAKADESDPVESK----KKKNKKKKKKSNVKK------I
AMPM_METJA         ----------------------------------------------------------
AMPM_SULSO         ----------------------------------------------------------
AMPM_METFE         ----------------------------------------------------------
AMPM_HELPY         ----------------------------------------------------------
MAP-3_insertion    ----------------------------------------------------------
MAP-3_fl           LPAAVSSAHPVPKHIKKPDYVTT-------GIVPDWGDSIEVKNEDQIQGLHQACQLARH
AMP1_HUMAN         PHYPLMPTRPVPSYIQRPDYADHPLGMSESEQALKGTSQIKLLSSEDIEGMRLVCRLARE
AMP1_YEAST         ASYPLTPRRYVPEDIPKPDWAAN--GLPVSEQRNDRLNNIPIYKKDQIKKIRKACMLGRE
AMP1_SYNY3         --------------------------------MGDTITLLSRREIEKMRQAGQLAAA
AMP2_SYNY3         -----------------MNHQNLLSITRNLVHPPISSGLVLLSARELDKMRRVGQLAAN
AMPM_ECOLI         ------------------------------------MAISIKTPEDIEKMRVAGRLAAE
AMPM_HAEIN         ------------------------------------MAIPIRTEKEIVKLREACKLASD
AMP3_SYNY3         PAWPRFLGTHPMNLLSQLFAPPSPVPSPTPKAKKRSRRGVQIKTPAEIAIMRQAGAIAAQ
AMPM_BACSU         -------------------------------------MIICKTPRELGIMREAGRIVAL
AMP2_MOUSE         CDLYPNGVFPKGQECEYPPTQDGRTAAMRTTSEEKKALDQASE--EIWNDFREAAEAHRQ
AMP2_RAT           CDLYPNGVFPKGQECEYPPTQDGRTAAWRTTSEEKKALDQASE--EIWNDFREAAEAHRQ
AMP2_HUMAN         CDLYPNGVFPKGQECEYPPTQDGRTAAWRTTSEEKKALDQASE--EIWNDFREAAEAHRQ
AMP2_YEAST         ELLFPDGKYPEGAWMDY--HQDFN--LQRTTDEESRYLKRDLERAEHWNDVRKGAEIHRR
AMPM_METJA         -----------------------------------------MEIEGYEKIIEAGKIASK
AMPM_SULSO         -----------------------------------------MTEDELNKLLLAGKIAAK
AMPM_METFE         ---------------------------------------------MEKFKKAGKIASK
AMPM_HELPY         -----------------------------------MAISIKSPKEIKAIRKAGELTAQ
MAP-3_insertion    -----------MTTEEIDALVHREIISHN-----AYPSPLGYG--GFP---KSVCTSVN
```

TABLE 1-continued

```
CLUSTAL W (1.74) multiple sequence alignment

MAP-3_fl        VLLLAGKSLKVDMTTEEIDALVHREIISHN-----AYPSPLGYG--GFP---KSVCTSVN
AMP1_HUMAN      VLDVAAGMIKPGVTTEEIDHAVHLACIARN-----CYPSPLNYY--NFP---KSCCTSVN
AMP1_YEAST      VLDIAAAHVRPGITTDELDEIVHNETIKRG-----AYPSPLNYY--NFP---KSLCTSVN
AMP1_SYNY3      LLDHLAPMVQPGITTLELNDEAEKWTKAHG-----AISAPLGYN--GFP---KSICTSIN
AMP2_SYNY3      LLNHLESMVQPGVSTQALNDEATRWMEDHG-----AISATLGYAPPGYPPFTGAICTSIN
AMPM-ECOLI      VLEMIEPYVKPGVSTGELDRICNDYIVNEQH----AVSACLGYH--GYP---KSVCISIN
AMPM_HAEIN      VLVMIEPYKKAGVTTGELDRICHEYMVNEQK----VIPACLNYH--GFP---KATCISIN
AMP3_SYNY3      VLKEIAATVQPGMTTGDLDQLAEERIRSLG-----ATPSFKGYH--GFP---ASICACVN
AMPM_BACSU      THEELKKHIKPGISTKELDQIAERFIKKQG-----AIPSFKGYN--GFR---GSICVSVN
AMP2_MOUSE      VRKYVMSWIKPGMTMIEICEKLEDCSRK-------LIKENGLNAGLAFP-----TGCSLN
AMP2_RAT        VRKYVMSWIKPGMTMIEICEKLEDCSRK-------LIKENGLNAGLAFP-----TGCSLN
AMP2_HUMAN      VRKYVMSWIKPGMTMIEICEKLEDCSRK-------LIKENGLNAGLAFP-----TGCSLN
AMP2_YEAST      VRRAIKDRIVPGMKLMDIADMIENTTRKYTGAENLLAMEDPKSQGIGFP-----TGLSLN
AMPM_METJA      VREEAVKLIIPGVKLLEVAEFVENRIRE-------------LGGEPAFP-----CNISIN
AMPM_SULSO      ARDEVSLDVKASAKVLDICEEVESIIIE-------------NKAFPSFP-----CNISIN
AMPM_METFE      VRKKAIKAVKGEMKILDLAEFIENEIEK-------------MGAKPAFP-----CNISVN
AMPM_HELPY      ALALLEREVRPGVSLLELDKMAEDFIKSSH-----ARPAFKGLY--GFP---NSVCMSLN
                ============.===:==========================:=========..:*

MAP-3_insertion NVLCHGIPD-SR--PLQDGDIINIDVTVYYNGYHGDTSRTFLVGN-----ED-----ECG
MAP-3_fl        NVLCHGIPD-SR--PLQDGDIINIDVTVYYNGYHGDTSETFLVGN-----VD-----ECG
AMP1_HUMAN      EVICHGIPD-RR--PLQEGDIVNVDITLYRNGYHGDLNETFFVGE-----VD-----DGA
AMP1_YEAST      EVICHGVPD-KT--VLKEGDIVNLDVSLYYQGYHADLNETYYVGEN----IS-----KEA
AMP1_SYNY3      EVICHGIPHRKR--VLQAGDIINVDVTPIVDGYHGDCSRTFFVGT-----PS-----PVA
AMP2_SYNY3      EVVCHGIPNPKQ--ILKDGDIINIDVTLRLAGYHGDTSRTFLVGS-----VS-----ATA
AMPM_ECOLI      EVVCHGIPDDAK--LLKDGDIVNIDVTVIKDGFHGDTSKMFIVGKP----T------IMG
AMPM_HAEIN      EVVCHGIPSDDK--VLKNGDIVNIDVTVIKDGYFGDNSKNYIVGGE----TN-----IRS
AMP3_SYNY3      NEVVHGIPRRRK--KIRSGDLLKVDTGAYFQGYHGDSCITIAVGK-----VS-----PQA
AMPM_BACSU      EELVHGIPGSR---VLKDGDIISIDIGAKLNGYHGDSAMTYPVGN-----IS-----DDD
AMP2_MOUSE      NCAAHYTPNAGDTTVLQYDDICKIDFGTHISGRIIDCAFTVTFN-----PKY--------
AMP2_RAT        NCAAHYTPNAGDTTVLQYDDICKIDFGTHISGRIIDCAFTVTFN-----PKY--------
AMP2_HUMAN      NCAAHYTPNAGDTTVLQYDDICKIDFGTHISGRIIDCAFTVTFN-----PKY--------
AMP2_YEAST      HCAAHFTPNAGDKTVLKYEDVNKVDYGVQVNGNIIDSAFTVSFD-----PQY--------
AMPM_METJA      EIAAHYTPKLNDNLEFKDDDVVKLDLGAHVDGYIADTAITVDLS-----NSY--------
AMPM_SULSO      SEAAHYSPTINDEKRIPEGAVVKDLGAHIDGFISDTAITISLD-----SRY--------
AMPM_METFE      EITAHYSPPCNDDRKILPGDLVKIDIGVMVDGFIGDTATTVLVEGYEDLKNYNDELAEKN
AMPM_HELPY      EVVIHGIPTDY---VLQEGDIIGLDLGVEVDGYYGDSALTLPIGA-----IS-----PQD
                ====*==========:====:==:*======*===*======.

MAP-3_insertion KKLVEVARRCRDEAIAACRAGAPFSVIGNTISHITH---------QNGFQVCPHFVGHGI
MAP-3_fl        KKLVEVARRCRDEAIAACRAGAPFSVIGNTISHITH---------QNGFQVCPHFVGHGI
AMP1_HUMAN      RKLVQTTYECLMQAIDAVKPGVRYRELGNIIQKHAQ---------ANGFSVVRSYCGHGI
AMP1_YEAST      LNTTETSRECLKLAIKMCKPGTTFQELGDHIEKRAT---------ENKCSVVRTYCGHGV
AMP1_SYNY3      EKLVKVTEECLRLGIEAVKPGGKIGDIGAAIQSHAE---------AQGFSVVRDFVGHGI
AMP2_SYNY3      RKLVEATQESMMRGIAEIKPGARIGDIGAAIQAYAE---------ASGFSVVRDMVGHGI
AMPM_ECOLI      ERLCRITQESLYLALRMVKPGINLREIGAAIQKFVE---------AEGFSVVREYCGHGI
AMPM_HAEIN      KKLVTAAQEALYVGIRTVKPDIRLNEIGKAVQKYTE---------SQTFSVVREYCGHGV
AMP3_SYNY3      QRLMEVAEGALYAGIEQVKPGNYLMDIAGAIEDYVK---------PTGYTIVEEFTGHGV
AMPM_BACSU      KKLLEVTEESLYKGLQEAKPGERLSNISHAIQTYVE---------NEQFSVVREYVGHGV
AMP2_MOUSE      DILLTAVKDATNTGIKCAGIDVRLCDVGEAIQEVMESYEVEIDGKTYQVKPIRNLNGHSI
AMP2_RAT        DILLKAVKDATNTGIKCAGIDVRLCDVGEAIQEVMESYEVEIDGKTYQVKPIRNLNGHSI
AMP2_HUMAN      DTLLKAVKDATNTGIKCAGIDVRLCDVGEAIQEVMESYEVEIDGKTYQVKPIRNLNGHSI
AMP2_YEAST      DNLLAAVKDATYTGIKEAGIDVRLTDIGEAIQEVMESYEVEINGETYQVKPCRNLCGHSI
AMPM_METJA      KDLVKASEDALYTVIKEINPPMNIGEMGKIIQEVIE---------SYGYKPISNLSGHVM
AMPM_SULSO      QRLLDASKTALEAAITNFKAGLSIGEIGRVIEKVIR---------AQGYKPIRNLGGHLI
AMPM_METFE      KKMIEAAESALENAINTIRDGVEIGKIGEVIENTIN---------KFGFKPISNLTGHTI
AMPM_HELPY      EKLLACSKESLNHAINSIRVGMHFKELSQILESTIT---------ERGFVPLKGFCGHGI
                ========.====:==============:.==:.========================**=:

MAP-3_insertion G-SYFHGHPEIWHHAND-S----DLPMEEGMAFTIEPIITEGSPEFKVLEDAWTVVSLDN
MAP-3_fl        G-SYFHGHPEIWHHAND-S----DLPMEEGMAFTIEPIITEGSPEFKVLEDANTVVSLDN
AMP1_HUMAN      H-KLFHTAPMVPHYAKNKA----VGVMKSGHVFTIEPMICEGGWQDETWPDGWTAVTRDG
AMP1_YEAST      G-EFFHCSPNIPHYAKNRT----PGVMKPGMVFTIEPMINEGTWKDMTWPDDWTSTTQDG
AMP1_SYNY3      S-KIFHTAPQIPHYGKAGK----GKRLRPGMVFTIEPMINEGTWEAVLLDDGWTAITKDG
AMP2_SYNY3      G-RQMHTELQIPHYGKRGS----GLKLRPGMVFTVEPMLNEGTYELTFLADGWTVITKDK
AMPM_ECOLI      G-RGFHEEPQVLHYDSRET----NVVLKPGMTFTIEPMVNAGKKEIRTMKDGWTVKTKDR
AMPM_HAEIN      G-TEFHCEPQVLHYYADDG----GVILKPGMVFTIEPMINAGKKEVRVMGDGWTVKTKDR
AMP3_SYNY3      G-QALHEDPHVFNVRCRDLP---NVKLKPGMTLAIEPIVNAGSRFTRTLGDRWTVVTVDN
AMPM_BACSU      G-QDLHEDPQIPHYGPPNK----GPRLKPGMVLAIEPMVNAGSRYVKTLADNWTVVTVDG
AMP2_MOUSE      GPYRIHAGKTVPIVKGGEA-----TRMEEGEVYAIETFGSTGKGVVHDDMECSHYMKNFD
AMP2_RAT        GPYRIHAGKTVPIVKGGEA-----TRMEEGEVYAIETFGSTGKGVVHDDMECSHYMKNFD
AMP2_HUMAN      GQYRIHAGKTVPIVKGGEA-----TRMEEGEVYAIETFGSTGKGVVHDDMECSHYMKNFD
AMP2_YEAST      APYRIHGGKSVPIVKNGDT-----TKMEEGEHFAIETFGSTGRGYVTAGGEVSHYARSAE
AMPM_METJA      HRYELHTGISIPNVYERTN-----QYIDVGDLVAIEPFATDGFGMVKDGNLGNIYKFLAK
AMPM_SULSO      RRYELHAGVFIPNVYERGL-----GVIQSDVYAIEPFATDGGGEVVEGKSITIYS--LK
AMPM_METFE      DRWVLHSGLSIPNVKGQNS-----HKL---------------------------------
AMPM_HELPY      G-KKPHEEPEIPNYLEKGVKPNSGPKIKEGMVFCLEPMVCQKQGEPKILADKWSVVSVDG
                =====*=====:================:

MAP-3_insertion QR-----SAQFEHTVLITSRGAQILTKLPHEA----------------------------
MAP-3_fl        QR-----SAQFEHTVLITSRGAQILTKLPHEA----------------------------
```

TABLE 1-continued

```
CLUSTAL W (1.74) multiple sequence alignment

AMP1_HUMAN       KR-----SAQFEHTLLVTDTGCEILTRRLDSARPHFMSQF--------------------
AMP1_YEAST       KL-----SAQFEHTLLVTEHGVEILTARNKKS-PGGPRQRIK------------------
AMP1_SYNY3       KL-----SAQFEHTIAVTEDGVEILTLGE-------------------------------
AMP2_SYNY3       KL-----SAQFEHTVVVTEEGVEILTLA--------------------------------
AMPM_ECOLI       SL-----SAQYEHTIVVTDNGCEILTLRKDDTIPAIISHDE-------------------
AMPM_HAEIN       SH-----SAQYEHQLIVTETGCEVMTIRDEEIAEGRISRIMVNV----------------
AMP3_SYNY3       AL-----SAQFEHTVLVTATGYELLTDRRLV-----------------------------
AMPM_BACSU       KK-----CAHFEHTIAITETGFDILTRV--------------------------------
AMP2_MOUSE       VGHVPIRLPRTKHLLNVINENFGTLAFCRRWLDRLGE--SKYLMALKNLCDLGIVDPYPP
AMP2_RAT         VGHVPIRLPRTKHLLNVINENFGTLAFCRRWLDRLGE--SKYLMALKNLCDLGIVDPYPP
AMP2_HUMAN       VGHVPIRLPRTKHLLNVINENFGTLAFCRRWLDRLGE--SKYLMALKNLCDLGIVDPYPP
AMP2_YEAST       DHQVMPTLDSAKNLLKTIDRMFGTLPFCRRYLDRLGQ--EKYLFALNNLVRHGLVQDYPP
AMPM_METJA       RP-IRLPQAR--KLLDVISKNYPYLPFAERWVLKNES----ERLALNSLIRASCIYGYPI
AMPM_SULSO       NPNIKGLSSRENELIDFIYTRFNYLPFSERWLKEFSTNVDELRNNIKNLVKKGALRGYPI
AMPM_METFE       -----------------------------------------------------------0
AMPM_HELPY       LN-----TSHHEHTIAIVGNKAVILTER--------------------------------
MAP-3_insertion  ------------------------------ (SEQ ID NO: 6)
MAP-3_fl         ------------------------------ (SEQ ID NO: 8)
AMP1_HUMAN       ------------------------------ (SEQ ID NO: 2)
AMP1_YEAST       ------------------------------ (SEQ ID NO: 9)
AMP1_SYNY3       ------------------------------ (SEQ ID NO: 10)
AMP2_SYNY3       ------------------------------ (SEQ ID NO: 11)
AMPM_ECOLI       ------------------------------ (SEQ ID NO: 12)
AMPM_HAEIN       ------------------------------ (SEQ ID NO: 13)
AMP3_SYNY3       ------------------------------ (SEQ ID NO: 14)
AMPM_BACSU       ------------------------------ (SEQ ID NO: 15)
AMP2_MOUSE       LCDIKGSYTAQFEHTILLRPTCKEVVSRGDDY (SEQ ID NO: 16)
AMP2_RAT         LCDIKGSYTAQFEHTILLRPTCKEVVSRGDDY (SEQ ID NO: 17)
AMP2_HUMAN       LCDIKGSYTAQFEHTILLRPTCKEVVSRGDDY (SEQ ID NO: 4)
AMP2_YEAST       LNDIPGSYTAQFEHTILLHAHKKEVVSKGDDY (SEQ ID NO: 18)
AMPM_METJA       LKERENGIVGQAEHTILITKNGVEITTK---- (SEQ ID NO: 19)
AMPM_SULSO       LIEIKKGVVSQFEHTVIVKGDSIIVSTKSL-- (SEQ ID NO: 20)
AMPM_METFE       ------------------------------ (SEQ ID NO: 21)
AMPM_HELPY       ------------------------------ (SEQ ID NO: 22)
```

In Table 2, originally located before the Sequence Listing, please change the value in the cell referring to the length of SEQ ID NO: 8, from 388 to 335 amino acids. The correct sequence of SEQ ID NO: 8 is shown in Table 1, in the application filed on Mar. 10, 2000, for the sequence labeled MAP-3_fl. A corrected Sequence Listing, is attached to this Entry Amendment. Please change the name of SEQ ID NO: 23 from "MetAP3-For1" to "MAP3-For1", which is more consistent with the naming scheme used for other oligonucleotides throughout the application and in the Sequence Listing.

TABLE 2

Table of Sequences

| SEQ ID NO | Description | Length | Type |
|---|---|---|---|
| 1 | homo sapiens MetAP1 | 2671 | DNA |
| 2 | homo sapiens MetAP1 | 394 | Protein |
| 3 | homo sapiens MetAP2 | 1908 | DNA |
| 4 | homo sapiens MetAP2 | 478 | Protein |
| 5 | homo sapiens MetAP3 clone GT9D Insert | 3114 | DNA |
| 6 | homo sapiens MetAP3 insert | 217 | Protein |
| 7 | homo sapiens MetAP3HZ2 - full length | 1529 | DNA |
| 8 | homo sapiens MetAP3HZ2 - full length | 335 | Protein |
| 9 | Saccharomyces cerevisiae MetAP1 | 387 | Protein |
| 10 | Synechocystis sp. MetAP1 | 253 | Protein |
| 11 | Synechocystis sp. MetAP2 | 274 | Protein |
| 12 | E. coli MetAP | 264 | Protein |
| 13 | Haemophilus influenzae MetAP | 268 | Protein |
| 14 | Synechocystis sp. MetAP | 305 | Protein |
| 15 | Bacillus subtilus MetAP | 248 | Protein |
| 16 | Mus musculus MetAP2 | 478 | Protein |

TABLE 2-continued

Table of Sequences

| SEQ ID NO | Description | Length | Type |
|---|---|---|---|
| 17 | Rattus MetAP2 | 478 | Protein |
| 18 | Saccharomyces cerevisiae MetAP2 | 421 | Protein |
| 19 | Metanothermus fervidus MetAP | 188 | Protein |
| 20 | Methanothermus jannaschii MetAP | 294 | Protein |
| 21 | Sulfolobus solfataricus MetAP | 301 | Protein |
| 22 | Helicobacter pylori MetAP | 250 | Protein |
| 23 | Homo sapiens MAP3-FOR1 primer | 20 | DNA |
| 24 | homo sapiens MAP3 FOR+ADAPT+ATG primer | 30 | DNA |
| 25 | homo sapiens MAP3 REV-NotI primer | 27 | DNA |
| 26 | homo sapiens MAP3 FOR2 primer | 17 | DNA |
| 27 | homo sapiens MAP3 FOR3 primer | 19 | DNA |
| 28 | homo sapiens MAP3 FOR4 primer | 17 | DNA |
| 29 | homo sapiens MAP3 FOR5 primer | 21 | DNA |
| 30 | homo sapiens MAP3 REV1 primer | 20 | DNA |
| 31 | homo sapiens MAP3 REV2 primer | 17 | DNA |
| 32 | homo sapiens MAP3 REV1.2 primer | 22 | DNA |
| 33 | homo sapiens MAP3 REV3 primer | 21 | DNA |
| 34 | homo sapiens MAP3 REV4 primer | 17 | DNA |
| 35 | homo sapiens hmap1F1 primer | 21 | DNA |
| 36 | homo sapiens hmap1R1 primer | 18 | DNA |
| 37 | hmap1P1 | 26 | DNA |
| 38 | homo sapiens hmap2F1 primer | 23 | DNA |
| 39 | homo sapiens hmap2R1 primer | 20 | DNA |
| 40 | homo sapiens hmap2P2 primer | 34 | DNA |
| 41 | homo sapiens hmap3F1 primer | 20 | DNA |
| 42 | hmap3R1 primer | 19 | DNA |
| 43 | hmap3R1 primer | 25 | DNA |
| 44 | homo sapiens map2bF primer | 22 | DNA |
| 45 | homo sapiens map2bR primer | 20 | DNA |

TABLE 2-continued

Table of Sequences

| SEQ ID NO | Description | Length | Type |
|---|---|---|---|
| 46 | homo sapiens map2bP primer | 31 | DNA |
| 47 | homo sapiens mp3bF primer | 23 | DNA |
| 48 | homo sapiens mp3bR primer | 27 | DNA |
| 49 | Homo sapiens mp3bP primer | 35 | DNA |
| 50 | *Homo sapiens* mp3cF primer | 24 | DNA |
| 51 | *Homo sapiens* mp3cR primer | 22 | DNA |
| 52 | *Homo sapiens* mp3cP primer | 24 | DNA |
| 53 | homo sapiens hcycmesF primer | 20 | DNA |
| 54 | homo sapiens hcycmesR primer | 22 | DNA |

TABLE 2-continued

Table of Sequences

| SEQ ID NO | Description | Length | Type |
|---|---|---|---|
| 55 | homo sapiens hcycmesP primer | 24 | DNA |
| 56 | homo sapiens revmp3cP primer | 24 | DNA |
| 57 | MetAP1 peptide antigen 1 | 20 | Protein |
| 58 | MetAP2 peptide antigen | 20 | Protein |
| 59 | MetAP3 peptide antigen | 20 | Protein |
| 60 | MetAP1 blocking peptide antigen | 20 | Protein |
| 61 | MetAP2 blocking peptide antigen | 20 | Protein |
| 62 | MetAP3 blocking peptide antigen | 20 | Protein |

---

We claim:

1. A purified nucleic acid encoding a protein having a methionine aminopeptidase (MetAP) type 3 (MetAP-3) activity selected from the group consisting of:
   (A) a nucleic acid comprising SEQ ID NO: 7, or its full complement, or a fragment thereof having a length of 300 to 1200 nucleotides;
   (B) a nucleic acid that specifically hybridizes under high stringency conditions to a nucleic acid of (A);
   (C) a nucleic acid encoding a protein having a sequence of SEQ ID NO: 8, or an enzymatically-active fragment of SEQ ID NO: 8 having a length greater than 100 contiguous amino acids;
   (D) a nucleic acid that specifically hybridizes under high stringency conditions to a nucleic of (C); and
   (E) A nucleic acid fragment of SEQ ID NO: 7, wherein said fragment is 300 to 1200 contiguous nucleotides in length and encodes a protein having MetAP3 activity.

2. The purified nucleic acid of claim 1, wherein said nucleic acid encodes a MetAP-3 protein.

3. The purified nucleic acid of claim 1, the nucleic acid encoding a protein having the sequence of SEQ ID NO: 8, or an enzymatically-active fragment of SEQ ID NO: 8 having a length greater than 100 contiguous amino acids, or their full complements.

4. The purified nucleic acid of claim 1, wherein the nucleic acid does not specifically hybridize, under high stringency conditions, to a nucleic acid, or its full complement, encoding a methionine aminopeptidase type 1 (MetAP-1) or methionine aminopeptidase type 2 (MetAP-2) protein.

5. The purified nucleic acid according to claim 1, wherein said nucleic acid specifically hybridizes to a nucleic acid that encodes MetAP-3, or full complement thereof, under high stringency conditions.

6. A purified MetAP-3 nucleic acid, which comprises a sequence that encodes a protein having MetAP3 activity and is identical to at least 300 contiguous nucleotides of SEQ ID NO: 7, or its full complement.

7. A method of producing a protein possessing MetAP-3 activity, comprising introducing a nucleic acid into a cell, the nucleic acid operably-linked to a promoter comprising a nucleic acid selected from the group consisting of:
   (A) a nucleic acid encoding a protein having a sequence of SEQ ID NO: 8 or a fragment of SEQ ID NO: 8 having a length of greater than 100 amino acids; and
   (B) a nucleic acid that specifically hybridizes under high stringency conditions to the full complement of (A).

* * * * *